United States Patent
Lightfoot et al.

(10) Patent No.: US 7,902,337 B2
(45) Date of Patent: Mar. 8, 2011

(54) ISOLATED SOYBEAN CYST NEMATODE AND SOYBEAN SUDDEN DEATH SYNDROME POLYPEPTIDES

(75) Inventors: David A. Lightfoot, Carbondale, IL (US); Khalid Meksem, Carbondale, IL (US)

(73) Assignee: Southern Illinois University, Carbondale, IL (US)

( * ) Notice: Subject to any disclaimer, the term of this patent is extended or adjusted under 35 U.S.C. 154(b) by 0 days.

(21) Appl. No.: 11/704,728

(22) Filed: Feb. 9, 2007

(65) Prior Publication Data

US 2008/0072352 A1 Mar. 20, 2008

Related U.S. Application Data

(62) Division of application No. 09/772,134, filed on Jan. 29, 2001, now abandoned.

(60) Provisional application No. 60/178,811, filed on Jan. 28, 2000.

(51) Int. Cl.
*C07K 14/37* (2006.01)
*C07K 17/00* (2006.01)
*A23J 1/14* (2006.01)

(52) U.S. Cl. .......................... 530/378; 530/350; 530/370

(58) Field of Classification Search .................. None
See application file for complete search history.

(56) References Cited

U.S. PATENT DOCUMENTS

| | | | |
|---|---|---|---|
| 4,196,265 A | 4/1980 | Koprowski et al. | |
| 4,554,101 A | 11/1985 | Hopp | |
| 4,940,935 A | 7/1990 | Riley | |
| 4,945,050 A | 7/1990 | Sanford et al. | |
| 5,036,006 A | 7/1991 | Sanford et al. | |
| 5,100,792 A | 3/1992 | Sanford et al. | |
| 5,188,642 A | 2/1993 | Shah et al. | |
| 5,260,203 A | 11/1993 | Ladner et al. | |
| 5,491,081 A | 2/1996 | Webb | |
| 5,523,311 A | 6/1996 | Schurter et al. | |
| 5,591,616 A | 1/1997 | Hiei et al. | |
| 5,614,395 A | 3/1997 | Ryals et al. | |
| 5,629,158 A | 5/1997 | Uhlen | |
| 5,639,949 A | 6/1997 | Ligon et al. | |
| 5,834,228 A | 11/1998 | Becker et al. | |
| 5,872,011 A | 2/1999 | Burley et al. | |
| 5,948,953 A | 9/1999 | Webb | |
| 5,952,546 A | 9/1999 | Bedbrook et al. | |
| 5,958,624 A | 9/1999 | Frech et al. | |
| 5,986,173 A | 11/1999 | Smeekens et al. | |
| 5,994,526 A | 11/1999 | Meulewaeter et al. | |
| 5,994,527 A | 11/1999 | Strittmatter et al. | |
| RE36,449 E | 12/1999 | Lebrun et al. | |
| 6,096,555 A | 8/2000 | Hermentin et al. | |
| 6,096,944 A | 8/2000 | Vierling et al. | |
| 6,162,967 A | 12/2000 | Webb | |
| 6,300,541 B1 | 10/2001 | Lightfoot et al. | |
| 6,538,175 B1 | 3/2003 | Webb | |
| 7,154,021 B2 | 12/2006 | Hauge et al. | |
| 7,485,770 B2 | 2/2009 | Hauge et al. | |
| 2002/0133852 A1 | 9/2002 | Hauge et al. | |
| 2002/0144310 A1 | 10/2002 | Lightfoot | |
| 2003/0005491 A1 | 1/2003 | Hauge et al. | |
| 2004/0237137 A1* | 11/2004 | Osumi et al. .................. 800/279 |
| 2008/0072352 A1 | 3/2008 | Lightfoot | |

FOREIGN PATENT DOCUMENTS

| | | |
|---|---|---|
| EP | 0 292 435 | 11/1988 |
| EP | 0 332 104 | 9/1989 |
| EP | 0 332 581 | 9/1989 |
| EP | 0 342 296 | 11/1989 |
| EP | 0 392 225 | 10/1990 |
| EP | 0 452 269 | 10/1991 |
| WO | WO 93/07278 | 4/1993 |
| WO | WO 93/21335 | 10/1993 |
| WO | WO 94/00977 | 1/1994 |
| WO | WO 97/47763 | 12/1997 |
| WO | WO 01/51627 | 7/2001 |

OTHER PUBLICATIONS

Bork et al. Genome Research, vol. 10, 2000, pp. 398-400.*
Parker et al. The Plant Cell (1996), vol. 8, pp. 2033-2046.*
Lacombe et al. Science Journal, vol. 292, pp. 1486-1487,( 2001).*
Bell-Johnson et al., "Biotechnology Approaches to Improving Resistance to SCN and SDS: Methods for High Throughput Marker Assisted Selection," Soybean Genetics Newsletter, p. 115-117, (1998).
Brucker et al., "RHG1 alleles from soybean PI 437654 and PI 88788 respond differentially to isolates of *Heterodera glycines* in the greenhouse," Theor. Appl Genet., vol. 111, pp. 44-49 (2005).
Chang et al., "Association of Loci Underlying Field Resistance to Soybean Sudden Death Syndrome (SDS) and Cyst Nematode (SCN) Race 3," Crop Sci., pp. 965-971 (1997).
Concibido et al, "A Decade of QTL Mapping for Cyst Nematode Resistance in Soybean", Crop Science, vol. 44, pp. 1121-1131 (2004).
Concibido et al., "Genome Mapping of Soybean Cyst Namatode Resistance Genes in 'Peking', PI 90763 and PI 88788 Using DNA Markers," Crop Sci., pp. 258-264 (1997).
Concibido et al., "Targeted Comparative Genome Analysis and Qualitative Mapping of a Major Partial-Resistance Gene to the Soynean Cyst Nematode," Theor. Appl. Genet., pp. 234-241, (1996).
Cregan et al., "An Integrated Genetic Linkage Map of the Soybean Genome," Crop Sci., pp. 1464-1490, (1999).
Cregan et al., "Two Simple Sequence Repeat markers to Select for Soybean Cyst Nematode Ressitance Coditioned by the rhg1 Locus," Theor. Appl. Genet., pp. 811-818, (1999).
Duggleby, "Identification of an acetolactate synthase small subunit gene in two eukaryotes," Gene, vol. 190, pp. 245-249 (1997).
Genebank Accession Nos. AY858565-AY858583, Oct. 4, 2005.
Kalinina, "Nanoliter Scale PCR with TaqMan Detection," Nucleic Acids Research, vol. 25 (No. 10), pp. 1999-2004 (1997).
Lee et al., "Homologous Recombination in Plant Cells after Argobacterium-Mediated Transformation", The Plant Cell, vol. 2, pp. 415-425 (May 1990).

(Continued)

*Primary Examiner* — Medina A Ibrahim
(74) *Attorney, Agent, or Firm* — Jenkins, Wilson, Taylor & Hunt, P.A.

(57) ABSTRACT

Soybean cyst nematode and soybean sudden death syndrome resistance genes, soybean cyst nematode and soybean sudden death syndrome resistant plant lines, and methods of breeding and engineering same.

4 Claims, 14 Drawing Sheets

OTHER PUBLICATIONS

Figure 3:
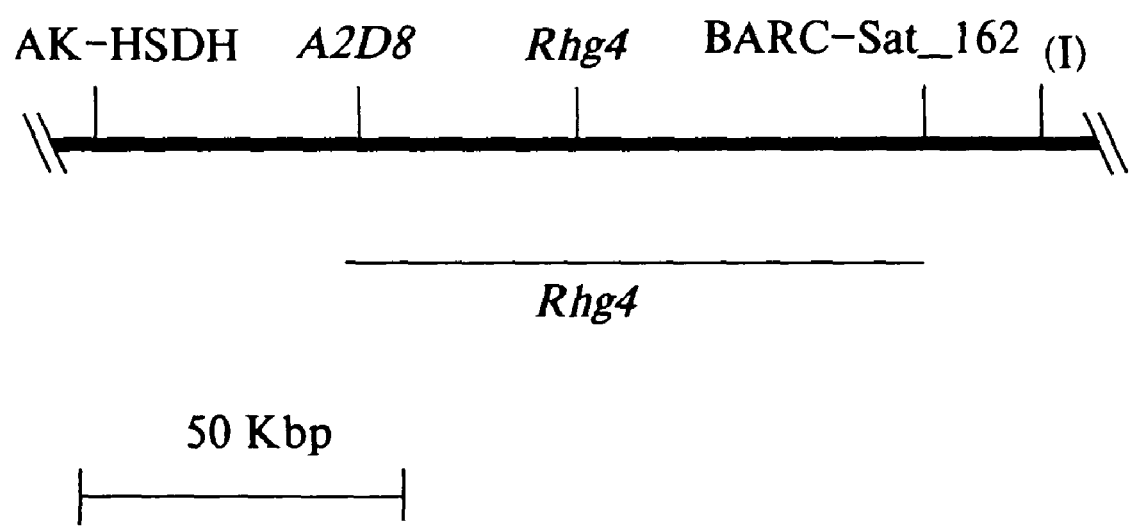

Livak et al., "Oligonucleotides With Fluorescent Dyes at Opposite Ends Provide a Quenched Probe System Useful for Detecting PCR Product and Nucleic Acid Hybridization," PCR Methods and Applications, pp. 357-362 (Dec. 20, 1994).

Livak et al., "Towards dully Automated Genome-Wide Polymorphism Screening," Nature Genetics, pp. 341-342 (1995).

Mahalingam et al., "Cytological Expression of Early Response to Infection by *Heterodera glycines* Ichinohe in Resistant PI 437654 Soybean," Genome, pp. 986-998 (1996).

Mahalingam et al., "DNA Markers for Resistance to *Heterodera glycines* I. Race 3 in Soybean Cultivar Peking," Breeding Science, pp. 435-443 (1995).

Mansur et al., "Generation mean analysis of resistance to race 3 of soybean cyst nematode," Crop Science, vol. 33, No. 6, pp. 1249-1255 (Nov.-Dec. 1993).

Matthews et al., "Molecular Markers Residing Close to the Rhg4 Locus Conferring Resistance to Soybean Cyst Nematode Race 3 on Linkage Group A of Soybean," Theor. Appl. Genet., pp. 1047-1052 (1998).

Meksem et al., "Clustering among loci underlying soybean resistance to *Fusarium solani*, SDS and SCN in near-isogenic lines", Theor. Appl. Genet., vol. 99, pp. 1131-1142 (1999).

Meksem et al., "Conversion of AFLP bands into high-throughput DNA markers," Mol. Genet. Genomics, vol. 265, pp. 207-214 (2001).

Meksem et al., "'Forrest' resistance to the soybean cyst nematode is bigenic: saturation mapping of the *Rhg1 and Rhg4* loci," Theor. Appl. Genet., vol. 103, pp. 701-717 (2001).

Meksem et al., "High-throughput genotyping for a polymorphism linked to soybean cyst nematode resistance gene *Rhg4* by using Taqman™ probes," Molecular Breeding, vol. 7, No. 63, pp. 63-71 (2001).

Meksem et al., "A High-Resolution Map of the Vicinity of the R1 Locus on Chromosome V of Potato Based on RFLP and AFLP Markers," Mol. Gen. Genet., pp. 74-81 (1995).

Meksem et al., "Clustering Among Loci Underlying Soybean Resistance to Fusarium Solani, SDS and SCN in Near-Isogenic Lines," Theor. Appl. Genet., pp. 1131-1142 (1999).

Meksem et al., "Conversion of AFLP Bands into High-Throughput DNA Markers," Mol. Genet. Genomics, vol. 265, pp. 207-214 (2001).

Meksem et al., "High-Throughput Genotyping for a Polymorphism Linked to Soybean Cyst Nematode Resistance Gene Rhg4 by Using Taqman TM Probes," Molecular Breeding, vol. 7, pp. 63-71 (2001).

Meksem et al., "Two Large-Insert Soybean genomic Libraries Constructed in a Binary Vector: Applications in Chromosome Walking and Genome Wide Physical Mapping," Theor. Appl. Genet., pp. 747-755 (2000).

Nasarabadi et al., "Simultaneous Detection of TaqMan Probes Containing Fam and Tamra Reporter Fluorophores," Biotechniques, vol. 27, No. 6, pp. 1116-1118 (1999).

Office Action corresponding to U.S. Appl. No. 09/772,134 dated Feb. 9, 2006.

Office Action corresponding to U.S. Appl. No. 09/772,134 dated Feb. 13, 2004.

Office Action corresponding to U.S. Appl. No. 09/772,134 dated May 7, 2003.

Office Action corresponding to U.S. Appl. No. 09/772,134 dated May 9, 2005.

Office Action corresponding to U.S. Appl. No. 09/772,134 dated Sep. 16, 2002.

Prabhu et al., "Selecting Soybean Cultivars for Dual Resistance to Soybean Cyst Nematode and SUdden Death Subdrome Using Two DNA Markers," Crop Sci., pp. 982-987 (1999).

Rao-Arelli et al., "Soybean Resistance to Soybean Cyst Nematode Race 3 Is Condition by an Additional Dominant Gene," Crop Science, vol. 32, pp. 862-864 (1992).

Staskawicz et al., "Molecular Genetics of Plant Disease Resistance", Science, vol. 268, pp. 661-667 (May 5, 1995).

Venkatesh et al., "Weed Hosts of Soybean Cyst Nematode (*Heterodera glycines*) in Ohio", Weed Technology, vol. 14, pp. 156-160 (2000).

Webb et al., "Genetic Mappling of Soybean Cyst Nematode Race-3 Resistance Loci in the Soybean PI 437.654," Theor. Appl. Genet., pp. 574-581 (1995).

Whitman et al., "The *N* Gene of Tobacco Confers Resistance to Tobacco Mosaic Virus in Transgenic Tomato," Proc. Natl. Acad. Sci. U.S.A., vol. 93, No. 16, pp. 8776-8781 (1996).

Zobrist et al., "Integrated Physical mapping of the Soybean Genome: A Tool for Rapid Identification of Economically Important Genes," Soybean Genetics Newsletter, pp. 1-9, (2000).

Genbank Accession No. AAC64606.1, (2001).
Genbank Accession No. AB010692, (2004).
Genbank Accession No. AC007020, (2002).
Genbank Accession No. AC007063, (2002).
Genbank Accession No. AF286700, (2006).
Genbank Accession No. AF286701, (2006).
Genbank Accession No. CAA74104, (2005).
Genbank Accession No. T00576, (1992).
Genbank Accession No. T46070, (1998).
Genbank Accession No. T47325, (1995).
Genbank Accession No. T47727, (1995).
Genbank Accession No. T47731, (1995).

* cited by examiner $E_{CTA}M_{AGG}113$

CTAF
ALLELE 1: 1    TTAAAGGGATATGTTTTTTCACTAATG-CtGTAAAAATTCACCC--AgATTTTTGCATTTTCtttgaaaaaatgt
ALLELE 2: 1    TTAAAGGGATATGTTTTTTCACTAATGtC-GTAAAAATTCACCCaA-ATTTTTGCATTTT-----------------

CTAR
ALLELE 1: 74   tagatatATCATGTTTTTTACAAGCATTACAATATATTCACTCGTATATTAGGAATTC 133
ALLELE 2: 61   -------ATCATGTTTTTTACAAGCATTACAATATATTCACTCGTATATTAGGAATTC 113

$E_{CCG}M_{AAC}405$

A2D8F
ALLELE1: 1     TTAAAACCTTGCGTGTGATCGGTATTACAGTACGCAGGGCCA----------ATCAACTAAAATA-TcTGCA
ALLELE 2: 1    TTAAAACCTTGCGTGTGATCGGTATTACAGTACGCAGGGCCAtgtgtttgagccaATCAACTAAAATAtT-TGCA A2D8R
ALLELE1: 62    AACGATAATATATAATTATAAGAAAAAGAC-aCACTTTGAGGGCATTTTTGACTTGAGAGAACTCAGGTATCAATCTAA
ALLELE2: 74    AACGATAATATATAATTATAAGAAAAAGACt-CACTTTGAGGGCATTTTTGACTTGAGAGAACTCAGGTATCAATCTAA ALLELE1: 138   AAGCAACGCTGTTCACCTTGAGCTGAAACACCTGAAACCAAACGCGAGAGAGAAATAAAG
ALLELE2: 150   AAGCAACGCTGTTCACCTTGAGCTGAAACACCTGAAACCAAACGCGAGAGAGAAATAAAG MICROSATELLITE
ALLELE1: 214   AACGGAAAcagagAGAGAGAGAAGGAAGGACCTTGTTCAAAGCAACGGGACAACTTTAGAGCCCTGGCGCGCGTGGG
ALLELE2: 226   AACGGAAAC----AGAGAGAGAGAAGGAAGGACCTTGTTCAAAGCAACGGGACAACTTTAGAGCCCTGGCGCGCGTGGG ALLELE1: 291   GGTCAATAAGCGTAACCTGGCTGAGGAGAGCCTCGGCG-tCGTCCTTGCTGAAGCAGAAGGAAGAG-CaCGAGA
ALLELE2: 299   GGTCAATAAGCGTAACCTGGCTGAGGAGAGCCTCGGCGc-CGTCCTTGCTGAAGCAGAAGGAAGAGCC-CGAGA ALLELE1: 365   CCAAGAGAAACTCCTCGGAAGCAACGGGAATTC 397
ALLELE2: 373   CCAAGAGAAACTCCTCGGAAGCAACGGGAATTC 405

FIG. 1a-1

$E_{CGG}M_{AGA}116$
ALLELE 1: 1    GAATTCCGGTTATCTCAGACAACTTTGTTGGTTTGGTTATAGTAAAGACACGATTAT
               |||||| ||||||||||||||||||||||||||||||||||||||||||||||||||
ALLELE 2: 1    GAATTCtGGTTATCTCAGACAACTTTGTTGGTTTGGTTATAGTAAAGACACGATTAT

ALLELE 1: 60   CCAGGCTTTGAGAGGCATAGAATAATTTTTTATATaaAAAAAAAGTCTCTTAA
               |||||||||||||||||||||||||||||||||||  ||||||||||||||||
ALLELE 2: 60   CCAGGCTTTGAGAGGCATAGAATAATTTTTTATAT--AAAAAAAGTCTCTTAA $E_{ATG}M_{CGA}87$
Allele 1: 1    GAATTCATGGTTTCTCTTAT-----GACATTGTGTGCCAAGTAATACTATATAAATTCAGATTTGGGTTT
               ||||||||||||||||||||     |||||||| |||||||||||||||||||||||||||||||||||
Allele 2: 1    GAATTCATGGTTTCTCTTATCttatGACATTGTgTGCCAAGTAATACTATATAAATTCAGATTTGGGTTT Allele 1: 68   CTGATAACCGTGGTCGTTAA 87
               |||||||||||||||||||||
Allele 2: 73   CAGATAACCGTGGTCGTTAA 92

$E_{CCC}M_{ATG}161$
ALLELE1: 1     TTAAATGAAAATCGATCAAATAATAATATATGCTTTTTTTAGTTG-gGTTCAAGT-ACT
               ||||||||||||||||||||||||||||||||||||||||||||| ||||||||| |||
ALLELE2: 1     TTAAATGAAAATCGATCAAATAATAATATATGCTTTTTTTAGTTGt-GTTCAAGTaACT

ALLELE1: 61    TTTTTTTATTGAAAAAAAATCGACCCAAGTTGAAACACATGTTGAGAATTGTTTTGT 116
               |||||||||||||||| |||||||||||||||||||||||||||||||||||||||||
ALLELE2: 62    TTTTTTTTATTGAAAAAAAAATCGACCCAAGTTGAAACACATGTTTGAGAATTGTTTTGT 117

ALLELE1: 117   GCATCCAACGTTTTCTTGTACAATCAGCTGTGAGAGGGGAATTC 161
               ||||||||||||||||||||||||||||||||||||||||||||
ALLELE2: 118   GCATCCAACGTTTTTCTTGTACAATCAGCTGTGAGAGGGGAATTC 162

$E_{CCA}M_{ACC}114$
ALLELE1: 1     GAATTCCCCAGcC-AGATTTGTATCAAACATGTATTGTCCAAATGTTCAAGCATCTTA 59
               ||||||||||| | ||||||||||||||||||||||||||||||||||||||||||||
ALLELE2: 1     GAATTCCCCAG-CtAGATTTGTATCAAACATGTATTGTCCAAAATGTTCAAGCATCTTA 59

ALLELE1: 60    GGGAACTGCTATTCTTACTTCTAAATTTTTATTGACATCCAAAGTGCTTTAA 114
               ||||||||||||||||||||||||||||||||||||||||||||||||||||
ALLELE2: 60    GGGAACTGCTATTCTTACTTCTAAATTTTTATTGACATCCAAAGTGCTTTAA 114

FIG. 1a-2

$E_{ATG}M_{CCA}87$ BAC extension and TaqMan probe and primers

```
Allele 1:  ttatcatccaaaattgaaaacttaatacaaatgcacatttttggagccattcatgtc
           ||||||||||||||||||||||||||||||||||||||||||||||||||||||||
Allele 2:  ttatcatccaaaattgaaaacttaatacaaatgcacatttttggagccattcatgtc
                                                  TMA5-RE Allele 1:  atctcttggtctgagtctctatcattctgtgattgAATTCATGGTTTCTCTTAT----GACATTGTT
           ||||||||||||||||||||||||||||||||||||||||||||||||||||      ||||||||
Allele 2:  atctcttggtctgagtctctatcattctgtgattgAATTCATGGTTTCTCTTATcttatGACATTGTT
                 TMA5F                      TMA5R        TMA5-S Allele 1:  GCCAAGTAATACTACTATATAAATTCAGATTTGGGTTTCTGATAACCGTGGTCGTTAAtactatataatacc
           ||||||||||||||||||||||||||||||||||||||||||||||||||||||||||||||||||||||
Allele 2:  GCCAAGTAATACTACTATATAAATTCAGATTTGGGTTTCAGATAACCGTGGTCGTTAAtactatataatacc
                                                 ATG4BACF
```

FIG. 1b

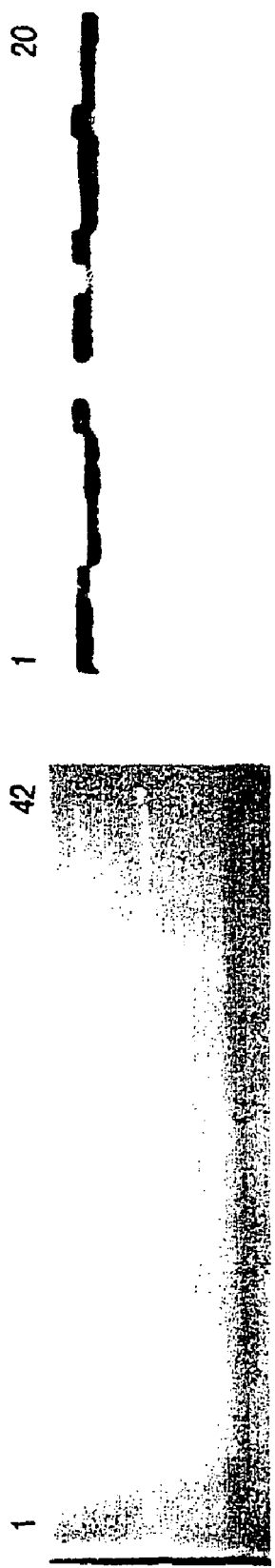
FIG. 2A
FIG. 2B
FIG. 2D
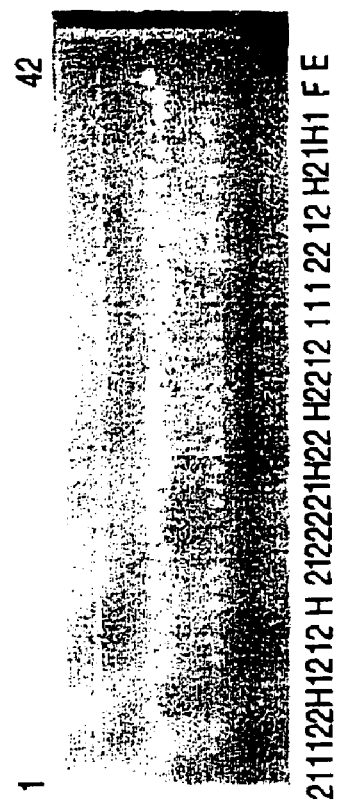
FIG. 2C

FIG. 6A
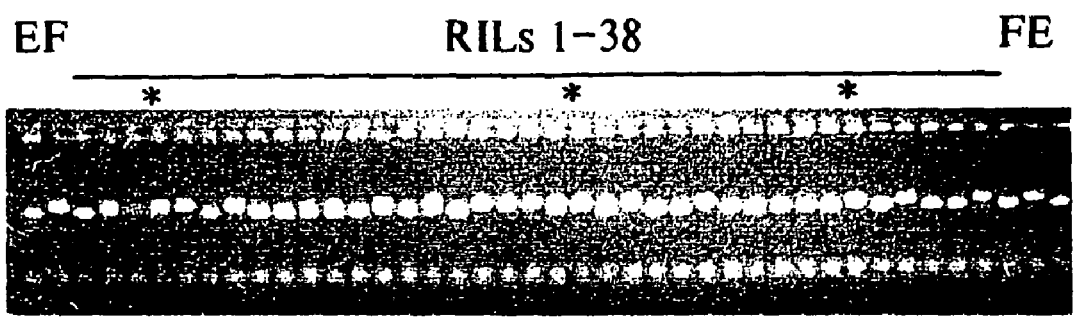
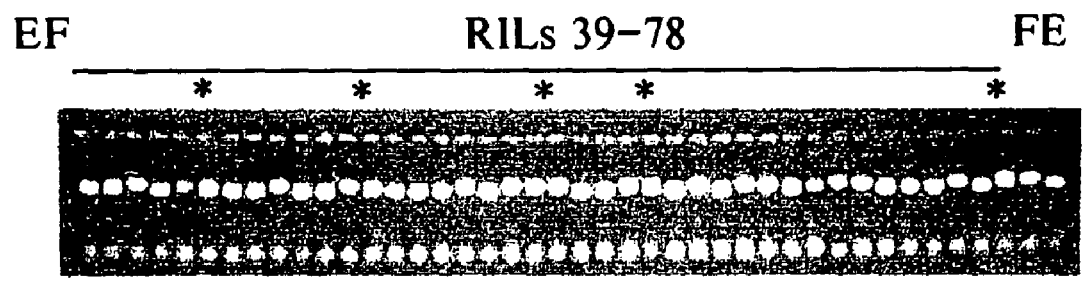
FIG. 6B

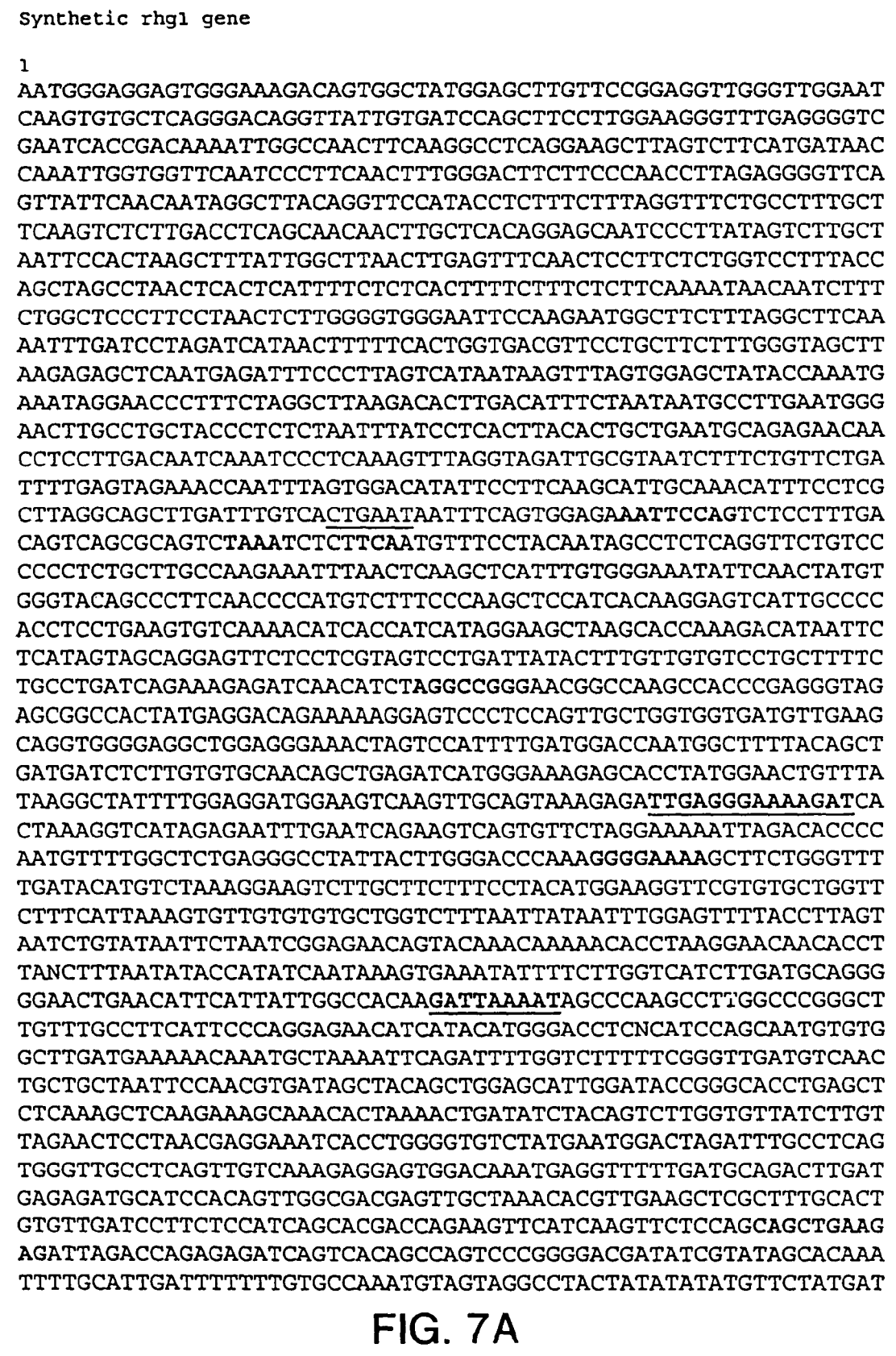

Synthetic rhg1 gene

1
AATGGGAGGAGTGGGAAAGACAGTGGCTATGGAGCTTGTTCCGGAGGTTGGGTTGGAAT
CAAGTGTGCTCAGGGACAGGTTATTGTGATCCAGCTTCCTTGGAAGGGTTTGAGGGGTC
GAATCACCGACAAAATTGGCCAACTTCAAGGCCTCAGGAAGCTTAGTCTTCATGATAAC
CAAATTGGTGGTTCAATCCCTTCAACTTTGGGACTTCTTCCCAACCTTAGAGGGGTTCA
GTTATTCAACAATAGGCTTACAGGTTCCATACCTCTTTCTTTAGGTTTCTGCCTTTGCT
TCAAGTCTCTTGACCTCAGCAACAACTTGCTCACAGGAGCAATCCCTTATAGTCTTGCT
AATTCCACTAAGCTTTATTGGCTTAACTTGAGTTTCAACTCCTTCTCTGGTCCTTTACC
AGCTAGCCTAACTCACTCATTTTCTCTCACTTTTCTTTCTCTTCAAAATAACAATCTTT
CTGGCTCCCTTCCTAACTCTTGGGGTGGAATTCCAAGAATGGCTTCTTTAGGCTTCAA
AATTTGATCCTAGATCATAACTTTTTCACTGGTGACGTTCCTGCTTCTTTGGGTAGCTT
AAGAGAGCTCAATGAGATTTCCCTTAGTCATAATAAGTTTAGTGGAGCTATACCAAATG
AAATAGGAACCCTTTCTAGGCTTAAGACACTTGACATTTCTAATAATGCCTTGAATGGG
AACTTGCCTGCTACCCTCTCTAATTTATCCTCACTTACACTGCTGAATGCAGAGAACAA
CCTCCTTGACAATCAAATCCCTCAAAGTTTAGGTAGATTGCGTAATCTTTCTGTTCTGA
TTTTGAGTAGAAACCAATTTAGTGGACATATTCCTTCAAGCATTGCAAACATTTCCTCG
CTTAGGCAGCTTGATTTGTCACTGAATAATTTCAGTGGAGAAATTCCAGTCTCCTTTGA
CAGTCAGCGCAGTCTAAATCTCTTCAATGTTTCCTACAATAGCCTCTCAGGTTCTGTCC
CCCCTCTGCTTGCCAAGAAATTTAACTCAAGCTCATTTGTGGGAAATATTCAACTATGT
GGGTACAGCCCTTCAACCCCATGTCTTTCCCAAGCTCCATCACAAGGAGTCATTGCCCC
ACCTCCTGAAGTGTCAAAACATCACCATCATAGGAAGCTAAGCACCAAAGACATAATTC
TCATAGTAGCAGGAGTTCTCCTCGTAGTCCTGATTATACTTTGTTGTGTCCTGCTTTTC
TGCCTGATCAGAAAGAGATCAACATCTAGGCCGGGAACGGCCAAGCCACCCGAGGGTAG
AGCGGCCACTATGAGGACAGAAAAAGGAGTCCCTCCAGTTGCTGGTGGTGATGTTGAAG
CAGGTGGGGAGGCTGGAGGGAAACTAGTCCATTTTGATGGACCAATGGCTTTTACAGCT
GATGATCTCTTGTGTGCAACAGCTGAGATCATGGGAAAGAGCACCTATGGAACTGTTTA
TAAGGCTATTTTGGAGGATGGAAGTCAAGTTGCAGTAAAGAGATTGAGGGAAAAGATCA
CTAAAGGTCATAGAGAATTTGAATCAGAAGTCAGTGTTCTAGGAAAAATTAGACACCCC
AATGTTTTGGCTCTGAGGGCCTATTACTTGGGACCCAAAGGGGAAAAGCTTCTGGGTTT
TGATACATGTCTAAAGGAAGTCTTGCTTCTTTCCTACATGGAAGGTTCGTGTGCTGGTT
CTTTCATTAAAGTGTTGTGTGTGCTGGTCTTTAATTATAATTTGGAGTTTTACCTTAGT
AATCTGTATAATTCTAATCGGAGAACAGTACAAACAAAAACACCTAAGGAACAACACCT
TANCTTTAATATACCATATCAATAAAGTGAAATATTTTCTTGGTCATCTTGATGCAGGG
GGAACTGAACATTCATTATTGGCCACAAGATTAAAATAGCCCAAGCCTTGGCCCGGGCT
TGTTTGCCTTCATTCCCAGGAGAACATCATACATGGACCTCNCATCCAGCAATGTGTG
GCTTGATGAAAAACAAATGCTAAAATTCAGATTTTGGTCTTTTTCGGGTTGATGTCAAC
TGCTGCTAATTCCAACGTGATAGCTACAGCTGGAGCATTGGATACCGGGCACCTGAGCT
CTCAAAGCTCAAGAAAGCAAACACTAAAACTGATATCTACAGTCTTGGTGTTATCTTGT
TAGAACTCCTAACGAGGAAATCACCTGGGGTGTCTATGAATGGACTAGATTTGCCTCAG
TGGGTTGCCTCAGTTGTCAAAGAGGAGTGGACAAATGAGGTTTTTGATGCAGACTTGAT
GAGAGATGCATCCACAGTTGGCGACGAGTTGCTAAACACGTTGAAGCTCGCTTTGCACT
GTGTTGATCCTTCTCCATCAGCACGACCAGAAGTTCATCAAGTTCTCCAGCAGCTGAAG
AGATTAGACCAGAGAGATCAGTCACAGCCAGTCCCGGGGACGATATCGTATAGCACAAA
TTTTGCATTGATTTTTTTGTGCCAAATGTAGTAGGCCTACTATATATATGTTCTATGAT

FIG. 7A

```
TCTTTCATTCTTATATTATTTTTGCCTGTTTGAATGCTTGAATTTGTACATACTCATAC
TACAATAAGGTGTAGTTCTGGTTAATTTTACCTCTACCTCAAAGCTGGGGTGTAATTCT
GTTTCCTCCAAGGCACATAATAGTTGAAAATAGTTCTCAGGAGCATTCATTGTTTATTC
TGCAAGATTCTCTTTCACGGCTGCTATCTTCTATGCATGCCCTGCCCATAAATGCATTA
TGAAGAATTGTAACGGCTGTGTTTTGGACTTCTTCAAAAAGTTTATGTTATTGCCAGG
TGTATATATCAACATGTTTTAAAGATTTTCAAACAATCAGGTTTTAGATGTGGGTTTGC
ATGCATGAGATTGGACTAGTGCGCTTGATGTAGTATAAAATATAAATTGTCCAATCAAG
CACCCTCTACATGTCCAAATAATGGGCCTTATGAAACTTAATTTTTAATTACAAACTA
CAGTAATCTTTTGAATAAAGATTTACAAATTACAACNGACATGTGAAGCNGCATCTTT
NATTGNCAATCTTTCAAGTTACTCTATTATTTTCTGCN
```

3105bp

FIG. 7B

Rhg1 Peptide
NGRSGKDSGYGACSGGWVGIKCAQGQVIVIQLPWKGLRGRIT
DKIGQLQGLRKLSLHDNQIGGSIPSTLGLLPNLRGVQLFNNRLG
SIP
LSLGFCPLLQSLDLSNNLLTGAIP
YSLANSTKLYWLNLSFNSFSGPLP
ASLTHSFSLTFLSLQNNNLSGSLPNSWGG
NSKNGFFRLQNLILDHNFFTGDVP
ASLGSLRELNEISLSHNKFSGAIP
NEIGTLSRLKTLDISNNALNGNLP
ATLSNLSSLTLLNAENNLLDNQIP
QSLGRLRNLSVLILSRNQFSGHIP
SSIANISSLRQLDLSLNNFSGEIP
VSFDSQRSLNLSNVSYNSLSGSVP PLLAKKFNSSSFVGNIQLCGYSP
STPCLSQ
APSQGVIAPPPEVSKHHHHR
KLSTKDIILIVAGVLLVVLIILCCVLLFCLIRKRS
TSKAGNGQATEGRAATMRTEKGVPPVAGGDVEAGGEAGGKLVHF
DGPMAFTADDLLCATAEIMGKSTYGTVYKAILEDGSQVAVKRLR
EKITKGHREFESEVSVLGKIRHPNGLALRAYYLGPKGEKLLVFD
YMSKGGLLLFYMEGSCAGSFIKVLCVLVFNYNLEFYLSNLYNSN
RRTVQTKTPKEQHLXFNIPYQ
-SEIFSWSS-CRGN-TFIIGHKMKIXQDLAVACSPSFPETSYMD
LXSSNVCX-NXMLKLQFWSFSVDVNCC-FQRDSYSWSIGIPGT-
ALKAQESKH-N-YLQSWCYLVRTPNEEITWGVYEWTRFASVGCL
SCQRGVDK-GF-CRLDERCIHSWRRVAKHVEARFALC-SFSIS
TTRSSSSSPAAGRD-TREISHSQSHLPGRPLEPYSESY

FIG. 7C

| Sequences producing significant alignments: | Score (bits) | E Value |
|---|---|---|
| pir:T46070 hypothetical protein T18N14.120 - Arabidopsis thaliana | 632 | e-180 |
| pir:T47727 hypothetical protein F18O21.60 - Arabidopsis thaliana | 344 | 1e-95 |
| pir:T04587 hypothetical protein F23E13.70 - Arabidopsis thaliana | 268 | 9e-71 |
| pir:T49038 hypothetical protein T5P19.20 - Arabidopsis thaliana | 257 | 2e-67 |
| pir:T48210 hypothetical protein T20L15.160 - Arabidopsis thaliana | 241 | 1e-62 |
| pir:T05050 protein kinase homolog M3E9.30 - Arabidopsis thaliana | 238 | 2e-61 |
| pir:T18536 receptor-like protein kinase - Ipomoea nil (Japanese... | 236 | 3e-61 |
| pir:T48489 receptor-like protein kinase - Arabidopsis thaliana | 236 | 5e-61 |
| pir:T10515 disease resistance protein Cf-2.2 - currant tomato | 235 | 6e-61 |
| pir:T10504 disease resistance protein Cf-2.1 - currant tomato | 235 | 6e-61 |
| pir:T30553 disease resistance protein Hcr2-5D - tomato | 229 | 4e-59 |
| pir:S27756 receptor-like protein kinase 5 (EC 2.7.1.-) precurso... | 227 | 1e-58 |
| pir:T48499 receptor-like protein kinase-like protein - Arabidop... | 226 | 3e-58 |
| pir:T46033 receptor protein kinase-like protein - Arabidopsis t... | 226 | 4e-58 |
| pir:T05335 hypothetical protein F1C12.190 - Arabidopsis thaliana | 221 | 1e-56 |
| pir:T10636 hypothetical protein T13K14.100 - Arabidopsis thaliana | 219 | 7e-56 |
| pir:T05898 hypothetical protein F6H11.170 - Arabidopsis thaliana | 218 | 1e-55 |
| pir:T45717 receptor-kinase like protein - Arabidopsis thaliana | 212 | 7e-54 |
| pir:T05322 hypothetical protein F18F4.240 - Arabidopsis thaliana | 211 | 1e-53 |
| pir:T10659 probable serine/threonine-specific protein kinase (E... | 211 | 2e-53 |
| pir:T03784 probable receptor protein kinase - rice | 208 | 1e-52 |
| pir:T50851 receptor protein kinase homolog [imported] - soybean | 201 | 1e-50 |
| pir:T45647 receptor protein kinase-like protein - Arabidopsis t... | 199 | 5e-50 |
| pir:T45718 receptor-kinase like protein - Arabidopsis thaliana | 199 | 7e-50 |
| pir:T50850 receptor protein kinase homolog [imported] - soybean | 199 | 7e-50 |
| pir:T45645 receptor kinase-like protein - Arabidopsis thaliana | 196 | 3e-49 |
| pir:T09356 brassinosteroid-insensitive protein BRI1 - Arabidops... | 196 | 3e-49 |
| pir:T00712 protein kinase homolog F22O13.7 - Arabidopsis thaliana | 190 | 2e-47 |
| pir:A57676 protein kinase Xa21 (EC 2.7.1.-), receptor type prec... | 190 | 3e-47 |
| pir:S39476 kinase-like transmembrane protein TMKL1 precursor - ... | 188 | 1e-46 |
| pir:T02154 protein kinase homolog T1F15.2 - Arabidopsis thaliana | 188 | 1e-46 |
| pir:T10725 protein kinase Xa21 (EC 2.7.1.-) A1, receptor type -... | 186 | 5e-46 |
| pir:T05897 protein kinase homolog F6H11.160 - Arabidopsis thaliana | 184 | 1e-45 |
| pir:T04313 protein kinase Xa21 (EC 2.7.1.-), receptor type - rice | 183 | 3e-45 |
| pir:T10727 protein kinase Xa21 (EC 2.7.1.-) D, receptor type - ... | 181 | 2e-44 |

FIG. 7D

```
>pir:T46070  hypothetical protein T18N14.120 - Arabidopsis thaliana
             Length = 836

Score =  632 bits (1613), Expect = e-180
 Identities = 329/550 (59%), Positives = 400/550 (71%), Gaps = 2/550 (0%)
 Frame = +1

Query: 7     RSGKDSGYGACSGGWVGIKCAQGQVIVIQLPWKGLRGRITDKIGQLQGLRKLSLHDNQIG 186
             +S +S       GW GIKC +GQV+ IQLPWKGL G I++KIGQL  LRKLSLH+N I
Sbjct: 72    KSWNNSASSQVCSGWAGIKCLRGQVVAIQLPWKGLGGTISEKIGQLGSLRKLSLHNNVIA 131

Query: 187   GSIPSTLGLLPNLRGVQLFNNRLTGSIPLSLGFCLCFKSLDLSNNLLTGAIPYSLANSTK 366
             GS+P +LG L +LRGV LFNNRL+GSIP+SLG C   ++LDLS+N LTGAIP SL  ST+
Sbjct: 132   GSVPRSLGYLKSLRGVYLFNNRLSGSIPVSLGNCPLLQNLDLSSNQLTGAIPPSLTESTR 191

Query: 367   LYWLNLSFNSFSGPLPASLTHSFSLTFLSLQNNNLSGSLPNSWGGNSKNGFFRLQNLILD 546
             LY LNLSFNS SGPLP S+  S++LTFL LQ+NNLSGS+P+ +      NG   L+ L LD
Sbjct: 192   LYRLNLSFNSLSGPLPVSVARSYTLTFLDLQHNNLSGSIPDFF----VNGSHPLKTLNLD 247

Query: 547   HNFFTGDVPASLGSLRELNEISLSHNKFSGAIPNEIGTLSRLKTLDISNNALNGNLPATL 726
             HN F+G VP SL   L E+S+SHN+ SG+IP E G L  L++LD S N++NG +P +
Sbjct: 248   HNRFSGAVPVSLCKHSLLEEVSISHNQLSGSIPRECGGLPHLQSLDFSYNSINGTIPDSF 307

Query: 727   SNLSSLTLLNAENNLLDNQIPQSLGRLRNLSVLILSRNQFSGHIPSSIANISSLRQLDLS 906
             SNLSSL  LN E+N L  IP ++ RL NL+ L L RN +G IP +I NIS +++LDLS
Sbjct: 308   SNLSSLVSLNLESNHLKGPIPDAIDRLHNLTELNLKRNKINGPIPETIGNISGIKKLDLS 367

Query: 907   LNNFSGEIPVSFDSQRSLNLFNVSYNSLSGSVPPLLAKKFNSSSFVGNIQLCGYSPSTPC 1086
             +NNF+G IP+S    L+ FNVSYN+LSG VPP+L+KKFNSSSF+GNIQLCGYS S PC
Sbjct: 368   ENNFTGPIPLSLVHLAKLSSFNVSYNTLSGPVPPVLSKKFNSSSFLGNIQLCGYSSSNPC 427

Query: 1087  LSQAPSQGVIAPP--PEVSKHHHHRKLSTKDIILIVAGVLLVVLIILCCVLLFCLIRKRS 1260
             +    +   P + + HHHRKLS KD+ILI G LL +L++LCC+LL CLI+KR+
Sbjct: 428   PAPDHHHPLTLSPTSSQEPRKHHHRKLSVKDVILIAIGALLAILLLLCCILLCCLIKKRA 487

Query: 1261  TSRPGTAKPPEGRAATMRTEKGVPPVAGGDVEAGGEAGGKLVHFDGPMAFTADDLLCATA 1440
                      K  +G+    T +EK V    G  AGGE GGKLVHFDGP  FTADDLLCATA
Sbjct: 488   -----ALKQKDGKDKT--SEKTVSAGVAGTASAGGEMGGKLVHFDGPFVFTADDLLCATA 540

Query: 1441  EIMGKSTYGTVYKAILEDGSQVAVKRLREKITKGHREFESEVSVLGKIRHPNVLALRAYY 1620
             EIMGKSTYGT YKA LEDG++VAVKRLREK TKG +EFE EV+ LGKIRH N+LALRAYY
Sbjct: 541   EIMGKSTYGTAYKATLEDGNEVAVKRLREKTTKGVKEFEGEVTALGKIRHQNLLALRAYY 600

Query: 1621  LGPKGEKLLGFD 1656
             LGPKGEKLL FD
Sbjct: 601   LGPKGEKLLVFD 612
```

FIG. 7E

```
Score =  185 bits (464), Expect = 1e-45
Identities = 93/161 (57%), Positives = 122/161 (75%), Gaps = 3/161 (1%)
Frame = +2

Query: 1943 GLVCLHSQENIIHGTSHPAMCGLMKNKC*NS---DFGLFRVDVNCC*FQRDSYSWSIGYR 2113
            GL  LHS EN+IH    +    ++ ++ N+   D+GL R+       + + ++GYR
Sbjct:  647 GLAHLHSNENMIH--ENLTASNILLDEQTNAHIADYGLSRLMTAAAATNVIATAGTLGYR 704

Query: 2114 APELSKLKKANTKTDIYSLGVILLELLTRKSPGVSMNGLDLPQWVASVVKEEWTNEVFDA 2293
            APE SK+K A+ KTD+YSLG+I+LELLT KSPG   NG+DLPQWVAS+VKEEWTNEVFD
Sbjct:  705 APEFSKIKNASAKTDVYSLGIIILELLTGKSPGEPTNGMDLPQWVASIVKEEWTNEVFDL 764

Query: 2294 DLMRDASTVGDELLNTLKLALHCVDPSPSARPEVHQVLQQLKRL 2425
            +LMR+   +VGDELLNTLKLALHCVDPSP+ARPE +QV++QL+ +
Sbjct:  765 ELMRETQSVGDELLNTLKLALHCVDPSPAARPEANQVVEQLEEI 808
```

FIG. 7F

SEQUENCE LISTING

<160> NUMBER OF SEQ ID NOS: 136

<210> SEQ ID NO 1
<211> LENGTH: 87
<212> TYPE: DNA
<213> ORGANISM: Glycine max

<400> SEQUENCE: 1
gaattcatgg tttctcttat gacattgttg ccaagtaata ctactatata aattcagatt      60
tgggtttctg ataaccgtgg tcgttaa                                          87

<210> SEQ ID NO 2
<211> LENGTH: 92
<212> TYPE: DNA
<213> ORGANISM: Glycine max

<400> SEQUENCE: 2
gaattcatgg tttctcttat cttatgacat tgttgccaag taatactact atataaattc      60
agatttgggt ttcagataac cgtggtcgtt aa                                    92

<210> SEQ ID NO 3
<211> LENGTH: 113
<212> TYPE: DNA
<213> ORGANISM: Glycine max

<400> SEQUENCE: 3
gaattcctaa tatacgagtg aatattattg taatgcttgt aaaaaaacat gataaaatgc      60
aaaaatttgg ggtgaatttt tacgacatta gtgaaaaaaa catatccctt taa             113

<210> SEQ ID NO 4
<211> LENGTH: 135
<212> TYPE: DNA
<213> ORGANISM: Glycine max

-continued

```
<400> SEQUENCE: 4 ttaagggat atgttttttt cactaatgct gtaaaattc acccagatt ttgcatttc      60 tttgaaaaaa tgtactagat atatcatgtt tttttacaag cattacaata atattcactc  120
gtatattagg aattc                                                   135

<210> SEQ ID NO 5
<211> LENGTH: 116
<212> TYPE: DNA
<213> ORGANISM: Glycine max

<400> SEQUENCE: 5
gaattccggt tatctcagac aacttttgtt tggtttggtt atagtaaaga cacgattatc   60
caggctttga gaggcataga aataatttt ttatataaaa aaaaagtct ctttaa       116

<210> SEQ ID NO 6
<211> LENGTH: 114
<212> TYPE: DNA
<213> ORGANISM: Glycine max

<400> SEQUENCE: 6
gaatttcggt tatctcagac aacttttgtt tggtttggtt atagtaaaga cacgattatc   60
caggctttga gaggcataga aataattttt ttatataaaa aaaagtctct ttaa        114

<210> SEQ ID NO 7
<211> LENGTH: 409
<212> TYPE: DNA
<213> ORGANISM: Glycine max
<220> FEATURE:
<221> NAME/KEY: misc_feature
<222> LOCATION: (1)..(409)
<223> OTHER INFORMATION: This sequence is derived from Glycine max cv.
      'Forrest'

<400> SEQUENCE: 7
gagtaaaacc ttgcgtgtga tcggtattac agtacgcagg ccaatcaac taaaatatct    60 gcaaacgata atataattat aagaaaaaga cacactttga gggcatttt gacttgagag   120 aactcaggta tcaatctaaa agcaacgctg ttcaccttga gctgaaacac ctggaggaga  180
aagcaaagca aaccaaacgc gagagagaaa taaagaacgg aaacagagag agagagagga  240
aggaccttgt tcaaagcaac ggggacaact ttagagccct ggcgcgcgtg ggggtcaata  300 agcgtaaccct ggctgaggag agcctcggcg tcgtccttgc tgaagcagaa gaggaagagc  360
acgagaccaa gagaaactcc tcggaagcaa cgggaattgg tacgcagtc              409

<210> SEQ ID NO 8
<211> LENGTH: 417
<212> TYPE: DNA
<213> ORGANISM: Glycine max

<400> SEQUENCE: 8
gagtaaaacc ttgcgtgtga tcggtattac agtacgcagg ccatggttt gagccaatca    60 actaaaatat ttgcaaacga taatataatt ataagaaaaa gactcacttt gagggcattt   120
ttgacttgag agaactcagg tatcaatcta aagcaacgc tgttcacctt gagctgaaac   180
acctggagga gaaagcaaag caaaccaaac gcgagagaga ataaagaac ggaaacagag   240 agagaggaag gaccttgttc aaagcaacgg ggacaacttt agagccctgg cgcgcgtggg   300
ggtcaataag cgtaacctgg ctgaggagag cctcggcgcc gtccttgctg aagcagaaga  360
ggaagagccc gagaccaaga gaaactcctc ggaagcaacg ggaattggta cgcagtc     417
```

<210> SEQ ID NO 9
<211> LENGTH: 165
<212> TYPE: DNA
<213> ORGANISM: Glycine max

<400> SEQUENCE: 9
gagtaaatga aaatcgatca aaatcaaata atatatgctt tttttagttg tgttcaagta    60 acttttttt attgaaaaaa tcgacccaag ttgaaacaca tgtttgagaa ttgttttgtg    120
catccaacgt ttttcttgta caatcagctg tgagagggga attgg    165

<210> SEQ ID NO 10
<211> LENGTH: 164
<212> TYPE: DNA
<213> ORGANISM: Glycine max

<400> SEQUENCE: 10
gagtaaatga aaatcgatca aaatcaaata atatatgctt tttttagttg ggttcaagta    60 cttttttta ttgaaaaaat cgacccaagt tgaaacacat gtttgagaat tgttttgtgc    120
atccaacgtt tttcttgtac aatcagctgt gagagggaa ttgg    164

<210> SEQ ID NO 11
<211> LENGTH: 114
<212> TYPE: DNA
<213> ORGANISM: Glycine max

<400> SEQUENCE: 11
gaattcccag ctagatttgt atcaaacatg tattgtccac aaaatgttca agcatcttag    60
ggaactgcta ttcttacttc taaatttttt attgacatcc aaagtgtgct ttaa    114

<210> SEQ ID NO 12
<211> LENGTH: 114
<212> TYPE: DNA
<213> ORGANISM: Glycine max

<400> SEQUENCE: 12
gaattcccag ccagatttgt atcaaacatg tattgtccac aaaatgttca agcatcttag    60
ggaactgcta ttcttacttc taaatttttt attgacatcc aaagtgtgct ttaa    114

<210> SEQ ID NO 13
<211> LENGTH: 3106
<212> TYPE: DNA
<213> ORGANISM: Glycine max
<220> FEATURE:
<221> NAME/KEY: misc_feature
<222> LOCATION: (1832)..(1832)
<223> OTHER INFORMATION: n is a, c, g, or t
<220> FEATURE:
<221> NAME/KEY: misc_feature
<222> LOCATION: (1990)..(1990)
<223> OTHER INFORMATION: n is a, c, g, or t
<220> FEATURE:
<221> NAME/KEY: misc_feature
<222> LOCATION: (3047)..(3047)
<223> OTHER INFORMATION: n is a, c, g, or t
<220> FEATURE:
<221> NAME/KEY: misc_feature
<222> LOCATION: (3060)..(3060)
<223> OTHER INFORMATION: n is a, c, g, or t
<220> FEATURE:
<221> NAME/KEY: misc_feature
<222> LOCATION: (3069)..(3069)
<223> OTHER INFORMATION: n is a, c, g, or t
<220> FEATURE:
<221> NAME/KEY: misc_feature -continued
<220> FEATURE:
<221> NAME/KEY: misc_feature
<222> LOCATION: (3074)..(3074)
<223> OTHER INFORMATION: n is a, c, g, or t
<220> FEATURE:
<221> NAME/KEY: misc_feature
<222> LOCATION: (3106)..(3106)
<223> OTHER INFORMATION: n is a, c, g, or t

<400> SEQUENCE: 13

```
aatgggagga gtgggaaaga cagtggctat ggagcttgtt ccggaggttg ggttggaatc    60
aagtgtgctc agggacaggt tattgtgatc cagcttcctt ggaagggttt gagggg tcga   120
atcaccgaca aaattggcca acttcaaggc ctcaggaagc ttagtcttca tgataaccaa   180
attggtggtt caatcccttc aactttggga cttcttccca accttagagg ggttcagtta   240
ttcaacaata ggcttacagg ttccatacct cttctttag gtttctgcct ttgcttcaag    300
tctcttgacc tcagcaacaa cttgctcaca ggagcaatcc cttatagtct tgctaattcc   360
actaagcttt attggcttaa cttgagtttc aactccttct ctggtccttt accagctagc   420
ctaactcact cattttctct cactttcttt tctcttcaaa ataacaatct ttctggctcc   480
cttcctaact cttggggtgg gaattccaag aatggcttct ttaggcttca aaatttgatc   540
ctagatcata acttttcac tggtgacgtt cctgcttctt tgggtagctt aagagagctc    600
aatgagattt cccttagtca taataagttt agtggagcta taccaaatga aataggaacc   660
ctttctaggc ttaagacact tgacatttct aataatgcct tgaatgggaa cttgcctgct   720
accctctcta atttatcctc acttacactg ctgaatgcag agaacaacct ccttgacaat   780
caaatccctc aaagtttagg tagattgcgt aatctttctg ttctgatttt gagtagaaac   840
caatttagtg gacatattcc ttcaagcatt gcaaacattt cctcgcttag gcagcttgat   900
ttgtcactga ataatttcag tggagaaatt ccagtctcct ttgacagtca gcgcagtcta   960
aatctcttca atgtttccta caatagcctc tcaggttctg tcccccctct gcttgccaag  1020
aaatttaact caagctcatt tgtgggaaat attcaactat gtgggtacag ccccttcaacc 1080
ccatgtcttt cccaagctcc atcacaagga gtcattgccc cacctcctga agtgtcaaaa  1140
catcaccatc ataggaagct aagcaccaaa gacataattc tcatagtagc aggagttctc  1200
ctcgtagtcc tgattatact ttgttgtgtc ctgcttttct gcctgatcag aaagagatca  1260
acatctaggc cgggaacggc caagccaccc gagggtagag cggccactat gaggacagaa  1320
aaaggagtcc ctccagttgc tggtggtgat gttgaagcag gtgggggaggc tggagggaaa  1380
ctagtccatt ttgatggacc aatggctttt acagctgatg atctcttgtg tgcaacagct  1440
gagatcatgg gaaagagcac ctatggaact gtttataagg ctattttgga ggatggaagt  1500
caagttgcag taaagagatt gagggaaaag atcactaaag gtcatagaga atttgaatca  1560
gaagtcagtg ttctaggaaa aattagacac cccaatgttt tggctctgag ggcctattac  1620
ttgggaccca aggggaaaa gcttctgggt tttgatacat gtctaaagga agtcttgctt  1680
ctttcctaca tggaaggttc gtgtgctggt tctttcatta aagtgttgtg tgtgctggtc  1740
tttaattata atttggagtt ttaccttagt aatctgtata attctaatcg gagaacagta  1800
caaacaaaaa cacctaagga acaacacctt anctttaata taccatatca ataaagtgaa  1860
atattttctt ggtcatcttg atgcagggg aactgaacat tcattattgg ccacaagatt   1920
aaaatagccc aagccttggc ccgggcttgt ttgccttcat tccaggagaa acatcataca  1980
tgggacctcn catccagcaa tgtgtggctt gatgaaaaac aaatgctaaa attcagattt  2040
tggtcttttt cgggttgatg tcaactgctg ctaattccaa cgtgatagct acagctggag  2100
cattggatac cgggcaccctg agctctcaaa gctcaagaaa gcaaacacta aaactgatat  2160
```

-continued

```
ctacagtctt ggtgttatct tgttagaact cctaacgagg aaatcacctg gggtgtctat      2220
gaatggacta gatttgcctc agtgggttgc ctcagttgtc aaagaggagt ggacaaatga      2280
ggtttttgat gcagacttga tgagagatgc atccacagtt ggcgacgagt tgctaaacac      2340
gttgaagctc gctttgcact gtgttgatcc ttctccatca gcacgaccag aagttcatca      2400
agttctccag cagctgaaga gattagacca gagagatcag tcacagccag tcccggggac      2460
gatatcgtat agcacaaatt ttgcattgat ttttttgtgc caaatgtagt aggcctacta      2520
tatatatgtt ctatgattct ttcattctta tattatttt gcctgtttga atgcttgaat       2580
ttgtacatac tcatactaca ataaggtgta gttctggtta attttacctc tacctcaaag      2640
ctggggtgta attctgtttc ctccaaggca cataatagtt gaaaatagtt ctcaggagca      2700
ttcattgttt attctgcaag attctctttc acggctgcta tcttctatgc atgccctgcc      2760
cataaatgca ttatgaagaa ttgtaacggc tgtgttttg gacttcttca aaaagtttat       2820
gttattgcca ggtgtatata tcaacatgtt ttaaagattt tcaaacaatc aggttttaga     2880
tgtgggtttg catgcatgag attggactag tgcgcttgat gtagtataaa atataaattg      2940
tccaatcaag caccctctac atgtccaaat aatgggcctt atgaaactta attttttaat     3000
tacaaactac agtaatcttt ttgaataaag atttacaaat tacaacngac atgtgaagcn      3060
gcatctttna ttgncaatct ttcaagttac tctattattt tctgcn                    3106
```

<210> SEQ ID NO 14
<211> LENGTH: 830
<212> TYPE: PRT
<213> ORGANISM: Glycine max
<220> FEATURE:
<221> NAME/KEY: misc_feature
<222> LOCATION: (611)..(611)
<223> OTHER INFORMATION: Xaa can be any naturally occurring amino acid
<220> FEATURE:
<221> NAME/KEY: misc_feature
<222> LOCATION: (618)..(618)
<223> OTHER INFORMATION: Xaa can be any naturally occurring amino acid
<220> FEATURE:
<221> NAME/KEY: misc_feature
<222> LOCATION: (627)..(627)
<223> OTHER INFORMATION: Xaa can be any naturally occurring amino acid
<220> FEATURE:
<221> NAME/KEY: misc_feature
<222> LOCATION: (632)..(632)
<223> OTHER INFORMATION: Xaa can be any naturally occurring amino acid
<220> FEATURE:
<221> NAME/KEY: misc_feature
<222> LOCATION: (643)..(643)
<223> OTHER INFORMATION: Xaa can be any naturally occurring amino acid
<220> FEATURE:
<221> NAME/KEY: misc_feature
<222> LOCATION: (663)..(663)
<223> OTHER INFORMATION: Xaa can be any naturally occurring amino acid
<220> FEATURE:
<221> NAME/KEY: misc_feature
<222> LOCATION: (669)..(670)
<223> OTHER INFORMATION: Xaa can be any naturally occurring amino acid
<220> FEATURE:
<221> NAME/KEY: misc_feature
<222> LOCATION: (672)..(672)
<223> OTHER INFORMATION: Xaa can be any naturally occurring amino acid
<220> FEATURE:
<221> NAME/KEY: misc_feature
<222> LOCATION: (689)..(689)
<223> OTHER INFORMATION: Xaa can be any naturally occurring amino acid
<220> FEATURE:
<221> NAME/KEY: misc_feature
<222> LOCATION: (705)..(705)
<223> OTHER INFORMATION: Xaa can be any naturally occurring amino acid
<220> FEATURE:
<221> NAME/KEY: misc_feature

```
<222> LOCATION: (715)..(715)
<223> OTHER INFORMATION: Xaa can be any naturally occurring amino acid
<220> FEATURE:
<221> NAME/KEY: misc_feature
<222> LOCATION: (717)..(717)
<223> OTHER INFORMATION: Xaa can be any naturally occurring amino acid
<220> FEATURE:
<221> NAME/KEY: misc_feature
<222> LOCATION: (758)..(758)
<223> OTHER INFORMATION: Xaa can be any naturally occurring amino acid
<220> FEATURE:
<221> NAME/KEY: misc_feature
<222> LOCATION: (761)..(761)
<223> OTHER INFORMATION: Xaa can be any naturally occurring amino acid
<220> FEATURE:
<221> NAME/KEY: misc_feature
<222> LOCATION: (787)..(787)
<223> OTHER INFORMATION: Xaa can be any naturally occurring amino acid
<220> FEATURE:
<221> NAME/KEY: misc_feature
<222> LOCATION: (807)..(807)
<223> OTHER INFORMATION: Xaa can be any naturally occurring amino acid

<400> SEQUENCE: 14

Asn Gly Arg Ser Gly Lys Asp Ser Gly Tyr Gly Ala Cys Ser Gly Gly
1               5                   10                  15

Trp Val Gly Ile Lys Cys Ala Gln Gly Gln Val Ile Val Ile Gln Leu
            20                  25                  30

Pro Trp Lys Gly Leu Arg Gly Arg Ile Thr Asp Lys Ile Gly Gln Leu
        35                  40                  45

Gln Gly Leu Arg Lys Leu Ser Leu His Asp Asn Gln Ile Gly Gly Ser
    50                  55                  60

Ile Pro Ser Thr Leu Gly Leu Leu Pro Asn Leu Arg Gly Val Gln Leu
65                  70                  75                  80

Phe Asn Asn Arg Leu Thr Gly Ser Ile Pro Leu Ser Leu Gly Phe Cys
                85                  90                  95

Pro Leu Leu Gln Ser Leu Asp Leu Ser Asn Asn Leu Leu Thr Gly Ala
            100                 105                 110

Ile Pro Tyr Ser Leu Ala Asn Ser Thr Lys Leu Tyr Trp Leu Asn Leu
        115                 120                 125

Ser Phe Asn Ser Phe Ser Gly Pro Leu Pro Ala Ser Leu Thr His Ser
    130                 135                 140

Phe Ser Leu Thr Phe Leu Ser Leu Gln Asn Asn Asn Leu Ser Gly Ser
145                 150                 155                 160

Leu Pro Asn Ser Trp Gly Gly Asn Ser Lys Asn Gly Phe Phe Arg Leu
                165                 170                 175

Gln Asn Leu Ile Leu Asp His Asn Phe Phe Thr Gly Asp Val Pro Ala
            180                 185                 190

Ser Leu Gly Ser Leu Arg Glu Leu Asn Glu Ile Ser Leu Ser His Asn
        195                 200                 205

Lys Phe Ser Gly Ala Ile Pro Asn Glu Ile Gly Thr Leu Ser Arg Leu
    210                 215                 220

Lys Thr Leu Asp Ile Ser Asn Asn Ala Leu Asn Gly Asn Leu Pro Ala
225                 230                 235                 240

Thr Leu Ser Asn Leu Ser Ser Leu Thr Leu Leu Asn Ala Glu Asn Asn
                245                 250                 255

Leu Leu Asp Asn Gln Ile Pro Gln Ser Leu Gly Arg Leu Arg Asn Leu
            260                 265                 270

Ser Val Leu Ile Leu Ser Arg Asn Gln Phe Ser Gly His Ile Pro Ser
        275                 280                 285

Ser Ile Ala Asn Ile Ser Ser Leu Arg Gln Leu Asp Leu Ser Leu Asn
```

```
            290                 295                 300
Asn Phe Ser Gly Glu Ile Pro Val Ser Phe Asp Ser Gln Arg Ser Leu
305                 310                 315                 320

Asn Leu Ser Asn Val Ser Tyr Asn Ser Leu Ser Gly Ser Val Pro Pro
                325                 330                 335

Leu Leu Ala Lys Lys Phe Asn Ser Ser Ser Phe Val Gly Asn Ile Gln
                340                 345                 350

Leu Cys Gly Tyr Ser Pro Ser Thr Pro Cys Leu Ser Gln Ala Pro Ser
                355                 360                 365

Gln Gly Val Ile Ala Pro Pro Glu Val Ser Lys His His His His
370                 375                 380

Arg Lys Leu Ser Thr Lys Asp Ile Ile Leu Ile Val Ala Gly Val Leu
385                 390                 395                 400

Leu Val Val Leu Ile Ile Leu Cys Cys Val Leu Phe Cys Leu Ile
                405                 410                 415

Arg Lys Arg Ser Thr Ser Lys Ala Gly Asn Gly Gln Ala Thr Glu Gly
                420                 425                 430

Arg Ala Ala Thr Met Arg Thr Glu Lys Gly Val Pro Pro Val Ala Gly
                435                 440                 445

Gly Asp Val Glu Ala Gly Glu Ala Gly Gly Lys Leu Val His Phe
450                 455                 460

Asp Gly Pro Met Ala Phe Thr Ala Asp Asp Leu Leu Cys Ala Thr Ala
465                 470                 475                 480

Glu Ile Met Gly Lys Ser Thr Tyr Gly Thr Val Tyr Lys Ala Ile Leu
                485                 490                 495

Glu Asp Gly Ser Gln Val Ala Val Lys Arg Leu Arg Glu Lys Ile Thr
                500                 505                 510

Lys Gly His Arg Glu Phe Glu Ser Glu Val Ser Val Leu Gly Lys Ile
                515                 520                 525

Arg His Pro Asn Gly Leu Ala Leu Arg Ala Tyr Tyr Leu Gly Pro Lys
                530                 535                 540

Gly Glu Lys Leu Leu Val Phe Asp Tyr Met Ser Lys Gly Gly Leu Leu
545                 550                 555                 560

Leu Phe Tyr Met Glu Gly Ser Cys Ala Gly Ser Phe Ile Lys Val Leu
                565                 570                 575

Cys Val Leu Val Phe Asn Tyr Asn Leu Glu Phe Tyr Leu Ser Asn Leu
                580                 585                 590

Tyr Asn Ser Asn Arg Arg Thr Val Gln Thr Lys Thr Pro Lys Glu Gln
                595                 600                 605

His Leu Xaa Phe Asn Ile Pro Tyr Gln Xaa Ser Glu Ile Phe Ser Trp
                610                 615                 620

Ser Ser Xaa Cys Arg Gly Asn Xaa Thr Phe Ile Ile Gly His Lys Met
625                 630                 635                 640

Lys Ile Xaa Gln Asp Leu Ala Val Ala Cys Ser Pro Ser Phe Pro Glu
                645                 650                 655

Thr Ser Tyr Met Asp Leu Xaa Ser Ser Asn Val Cys Xaa Xaa Asn Xaa
                660                 665                 670

Met Leu Lys Leu Gln Phe Trp Ser Phe Ser Val Asp Val Asn Cys Cys
                675                 680                 685

Xaa Phe Gln Arg Asp Ser Tyr Ser Trp Ser Ile Gly Ile Pro Gly Thr
                690                 695                 700

Xaa Ala Leu Lys Ala Gln Glu Ser Lys His Xaa Asn Xaa Tyr Leu Gln
705                 710                 715                 720
```

```
Ser Trp Cys Tyr Leu Val Arg Thr Pro Asn Glu Glu Ile Thr Trp Gly
                725                 730                 735

Val Tyr Glu Trp Thr Arg Phe Ala Ser Val Gly Cys Leu Ser Cys Gln
            740                 745                 750

Arg Gly Val Asp Lys Xaa Gly Phe Xaa Cys Arg Leu Asp Glu Arg Cys
        755                 760                 765

Ile His Ser Trp Arg Arg Val Ala Lys His Val Glu Ala Arg Phe Ala
    770                 775                 780

Leu Cys Xaa Ser Phe Ser Ile Ser Thr Thr Arg Ser Ser Ser Ser Ser
785                 790                 795                 800

Pro Ala Ala Gly Arg Asp Xaa Thr Arg Glu Ile Ser His Ser Gln Ser
                805                 810                 815

His Leu Pro Gly Arg Pro Leu Glu Pro Tyr Ser Glu Ser Tyr
            820                 825                 830

<210> SEQ ID NO 15
<211> LENGTH: 726
<212> TYPE: DNA
<213> ORGANISM: Glycine max
<220> FEATURE:
<221> NAME/KEY: misc_feature
<222> LOCATION: (1)..(726)
<223> OTHER INFORMATION: promoter region

<400> SEQUENCE: 15
gaatacgaat tccattttcg cgacagtagc tcagaatagg ttcatactcc tgccatcttt      60
gaggcggnca atgcaacgtg taagacttca aggtgtctcc atctatcctg ccatgaaagt     120
caagtttcag gacaagtaat gcagaattat ggaaaagcaa tctgactaag acaaaagagc     180
ttcagagatt aacagaaaat agtgagccag aaaaagatt gcgagacaga aattggtcgc      240
caacaaaaag ttgtctcttt tataattttt aattgaaatt ttcttaattt agctaacatg     300
acttcctacg gccacaattg cgtttgcaga cacttaaaaa acttgatgtt gcagcaaaaa     360
tcacgtttta tttattattg atgtcaatta tttaacagtt ttatgttagg tttaataaca     420
gtaggttgat gcaagaggct aaacattaat cagaaattga aaggcagggn tattacttct     480
tatccatata ctgattgagc gggtcctgaa gaatagcggg aaaaacttca agcgccagag     540
acaatagttt tttcttttca aacagcgcct atgcaaattc ttccaatctc aagcttcaat     600
tcctatcgtc tcgaaccgga cttgntctgn ttnacctaaa tccccactcg gcattnatna     660
acttntcccc actttccttt ntctttccta tcgccaccgg tcttctatnc ccgcccgtcg     720 naatct                                                                726

<210> SEQ ID NO 16
<211> LENGTH: 649
<212> TYPE: DNA
<213> ORGANISM: Glycine max
<220> FEATURE:
<221> NAME/KEY: misc_feature
<222> LOCATION: (1)..(649)
<223> OTHER INFORMATION: partial cDNA

<400> SEQUENCE: 16
aggagtggga aagacagtgg ctatggagct tgttccggag gttgggttgg aatcaagtgt      60
gctcagggac aggttattgt gatccagctt ccttggaagg gtttgagggg tcgaatcacc     120
gacaaaattg ccaacttcaa aggcctcagg aagcttagtc ttcatgataa ccaaattggt     180
ggttcaatcc cttcaacttt gggacttctt cccaacctta gggggttcag ttattcaac      240 aataggctta caggttccat acctcttcct ttaggttct gcccttttgct tcagtctctt     300
```

```
gacctcagca acaacttgct cacaggagca atcccttata gtcttgctaa ttccactaag    360
ctttattggc ttaacttgag tttcaactcc ttctctggtc ctttaccagc tagcctaact    420
cactcatttt ctctcacttt tctttctctt caaaataaca atctttctgg ctcccttcct    480
aactcttggg gtgggaattc caagaatggc ttctttaggc ttcaaaattt gatcctagat    540
cataactttt tcactggtga cgttcctgct tctttgggta gcttaagaga gctcaatgag    600
aattccctta agcataataa ggttagggga gctatcccaa atgaaatnt               649
```

<210> SEQ ID NO 17
<211> LENGTH: 558
<212> TYPE: DNA
<213> ORGANISM: Glycine max
<220> FEATURE:
<221> NAME/KEY: misc_feature
<222> LOCATION: (1)..(558)
<223> OTHER INFORMATION: partial cDNA

<400> SEQUENCE: 17

```
aggantgggn aagacantgg ctattttagc tttggtcccg gagggtgggt tggaatcaan     60
tgngctcaag gacaaggtat tgtgaaccaa cttnctttga aaggnttgag ggggcgaaac    120
acccacaaaa atgggcaact tnaaagnctc angaagctta atcttnatga aaaccaaaat    180 gggggggtcaa anccntcaac ttttggactt cttttccaacc ttagagggg tcaattattc    240 aacaataggn ttacagggtc atacctctt tctttaaggt tctgcccttt gnttcagnct    300
cttgacctca acaacaactt gctnacagga agcaatccct tatagtcttg ctaattccac    360
taagctttat tggcttaact ttgagnttca actnctttct ntgggncttt accaactagn    420
ctaactcact cattttctct cactttttt tntntttaaa aaaacaaaca tttntngntt    480 ccccttctnac tcntgggggg gggaaaaaca annaaaggnt tctttaggnt tcaaaaaatg    540
atcctanaac ataacttt                                                   558
```

<210> SEQ ID NO 18
<211> LENGTH: 794
<212> TYPE: DNA
<213> ORGANISM: Glycine max
<220> FEATURE:
<221> NAME/KEY: misc_feature
<222> LOCATION: (1)..(794)
<223> OTHER INFORMATION: partial cDNA

<400> SEQUENCE: 18

```
aatgggagga gtgggaaaga cagtggctat ggagcttgtt ccggaggttg ggttggaatc     60
aagtgtgctc agggacaggt tattgtgatc cagcttcctt ggaagggttt gagggggtcga    120 atcaccgaca aaattggcca acttcaaggc ctcaggaagc ttagtcttca tgataaccaa    180
attggtggtt caatcccttc aactttggga cttcttccca accttagagg ggttcagtta    240
ttcaacaata ggcttacagg ttccatacct ctttctttag gtttctgccc tttgcttcag    300
tctcttgacc tcagcaacaa cttgctcaca ggagcaatcc cttatagtct tgctaattcc    360
actaagcttt attggcttaa cttgagtttc aactccttct ctggccttta ccagctagcc    420
taactcactc attttctctc acttttcttt ctcttcaaaa taacaatctt tctggctccc    480
ttcctaactc ttggggnggg aatttcaaga atggcttctt taggcttcaa aatttgatcc    540
tagatcataa cttttttnctg gtgacgttcc tgcttctttg ggtagcttaa gagagcccna    600
tgagaattcc cttagtcatn ataagnttag tggagctttc caantgaaat anggaccct    660 tntaggctta aacactngnc attctaataa tgccttgaat gggaacctcc ctgttccctc    720
```

```
tttanttatc tcccttncnc ngctggangc cagaccaccn cntgncaatn aatccctcaa    780
agttaggtac atcg                                                      794

<210> SEQ ID NO 19
<211> LENGTH: 781
<212> TYPE: DNA
<213> ORGANISM: Glycine max
<220> FEATURE:
<221> NAME/KEY: misc_feature
<222> LOCATION: (1)..(781)
<223> OTHER INFORMATION: partial cDNA

<400> SEQUENCE: 19
ggaggagtgg gaaagacagt ggctatggag cttgttccgg aggttgggtt ggaatcaagt     60
gtgctcaggg acaggttatt gtgatccagc ttccttggaa ggggtttgag gggtcgaatc    120
accgacaaaa ttggccaact tcaaggcctc aggaagctta gtcttcatga taaccaaatt    180
ggtggtcaat cccttcaact ttgggacttc ttccaacctt agagggttc aagttattca     240 acaataggct tacaggttcc atacctcttt ctttaggttt ctgccctttg cttcaagtct    300
cttgacctca gcaacaactt gctcacagga gcaatccctt atagtcttgc taattccact    360
aagctttatt ggcttaactt gagtttcaac tncttctctg gnccttttacc agctagccta   420 actcactcat tttctctcac ttttctttct cttcaaaaaa acaaactttc tgggtccttt    480
ctactcttgg gggggaatt ccagaatggn ttctttaggg ttnaaaattg atcctagaca     540
tactttttac tggggacgtc ctgcttcttt ggnagcttaa agagctcaat gagattncct    600
tagcataata agttaggggg gctttnccaa agnaatagga nccttntag ggttaaaaac     660 ctggcatttt taaaatgcct tgaangggac ttgnccgctn cccctntaat tatccncctt    720
acnccgntgg anggagagaa aanccccttg caaanaaaac cctcaaaggt tagggngatc    780
g                                                                   781

<210> SEQ ID NO 20
<211> LENGTH: 861
<212> TYPE: DNA
<213> ORGANISM: Glycine max
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
```

<222> LOCATION: (794)..(794)
<223> OTHER INFORMATION: n is a, c, g, or t
<220> FEATURE:
<221> NAME/KEY: misc_feature
<222> LOCATION: (796)..(797)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t

<400> SEQUENCE: 20

```
gaatgggagg agtgggaaag acagtggcta tggagcttgt tccggaggtt gggttggaat      60
caagtgtgct cagggacagg ttattgtgat ccagcttcct tggaagggtt tgaggggtcg     120
aatcaccgac aaaattggcc aacttcaagg cctcaggaag cttagtcttc atgataacca     180
aattggtggt tcaatccctt caactttggg acttcttccc aaccttagag gggttcagtt     240
attcaacaat aggcttacag gttccatacc tctttcttta ggtttctgcc ctttgcttca     300
gtctcttgac ctcagcaaca acttgctcac aggagcaatc ccttatagtc ttgctaattc     360
cactaagctt tattggctta acttgagttt caactccttc tctggtcctt taccagctag     420
cctaactcac tcatttttctc tcactttttct ttctcttcaa ataacaatc tttctggctc     480
ccttcctaac tcttggggtg ggaattccaa gaatggcttc tttaggcttc aaaatttgat     540
cctagatcat aacttttttca ctggtgacgt tcctgcttct ttgggtagct taagagagct     600
caatgagatt tcccttagtc ataataaagt ttaatggagc tataccaaat gaaataggaa     660
cccttctan gcttaaacac ttgacattn taataatgnc ttgaatggga acttgcctgc     720
taccctctnt aattatcctn cttacactgn tgaatgcaaa aaacaacctc ttgcaataaa     780
tcccttaaan ttangnnaat gggaaanttn tttntgattt gagtnaaacc aattaatggc     840
atattnttta acatttaaan t                                               861
```

<210> SEQ ID NO 21
<211> LENGTH: 761
<212> TYPE: DNA
<213> ORGANISM: Glycine max
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t

```
-continued

<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (717)..(718)
<223> OTHER INFORMATION: n is a, c, g, or t
<220> FEATURE:
<221> NAME/KEY: misc_feature
<222> LOCATION: (724)..(726)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
```

<400> SEQUENCE: 21

```
gaatgggagg agtgggaaag acatggggtt gaagggctgt acccacatag ttgaatattt      60
cccacaaatg agcttgagtt aaatttcttg gcaagcagag gggggacaga acctgagagg     120
ctattgtagg aaacattgaa gggatttaga ctgcgctgac tgtcaaagga gactggaatt     180
tctccactga aattattcag tgacaaatca agctgcctaa gcgaggaaat gtttgcaatg     240
cttgaaggaa tatgtccact aaattggttt ctactcaaaa tcagaacaga aagattacgc     300
aatctaccta aactttgagg gatttgattg tcaaggaggt tgttctctgc attcagcagt     360
gtaagtgagg ataaattaga gagggtagca ggcaagttcc cattcaaggc attattagaa     420
atgtcaagtg tcttaagcct anaaagggtt cctatttcat ttggtatagc tccctaaact     480
tattatgact aagggaaatc tnattgagct ctnttaactc ccaaagaaca ggacgtncca     540
gtgaaaaagt atnatctagg atcaaatttg aacctaaaaa gcattttgga tccccccaaa     600
gtaggaagga gcanaagatg tntttnaaaa anaaatanaa aatatagtag tactgtaagc     660
naaaaggtga ctaatagcat aantatgata caaattagga tttcttanaa tttttttnnaa     720
aatnnnangn aaccaaaaaa gngacntncn tttnaanacc c                         761
```

<210> SEQ ID NO 22
<211> LENGTH: 856
<212> TYPE: DNA
<213> ORGANISM: Glycine max
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature

```
<222> LOCATION: (771)..(771)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (829)..(830)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (849)..(850)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t

<400> SEQUENCE: 22
aatgggagga gtgggaaaga cagtggctat ggagcttgtt ccggaggttg ggttggaatc    60
aagtgtgctc agggacaggt tattgtgatc cagcttcctt ggaagggttt gaggggtcga   120
atcaccgaca aaattggcca acttcaaggc ctcaggaagc ttagtcttca tgataaccaa   180
attggtggtt caatcccttc aactttggga cttcttccca accttagagg ggttcagtta   240
ttcaacaata ggcttacagg ttccatacct cttcttttag gtttctgcct ttgcttcaag   300
tctcttgacc tcagcaacaa cttgctcaca ggagcaatcc cttatagtct tgctaattcc   360
actaagcttt attggcttaa cttgagtttc aactccttct ctggtccttt accagctagc   420
ctaactcact catttctct cactttctt tctcttcaaa anaacaatct ttctggctcc     480
cttcctaact cttggggtgg gaattccaag aatggcttct ttaggcttca aaaattgatc   540
ctagaacata acttttttac tggtgacgtt cctgctttt ttggtaggct taaaganaag    600
ccaatgagaa tttccttagt catnataaag ttaaggggag cttttnccaa atgaaaaag    660 gaacccttn taggcttaaa nanacttgac aattntaat aatgcccttg aatngggaac     720
ttgcctgcta cccccttaa tttatcctac ttacctgnt ngaaggcaaa naacaacccc     780
tttgcaataa aaacccnaaa gttaagggga angnggnact ttntntctnn tttngggnaa   840
```
accanttann ggcnct 856

<210> SEQ ID NO 23
<211> LENGTH: 826
<212> TYPE: DNA
<213> ORGANISM: Glycine max
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t

<400> SEQUENCE: 23
gaatgggagg agtgggaaag acatgggggtt gaagggctgt acccacatag ttgaatattt    60

```
cccacaaatg agcttgagtt aaatttcttg gcaagcagag gggggacaga acctgagagg    120
ctattgtagg aaacattgaa gggatttaga ctgcgctgac tgtcaaagga gactggaatt    180
tctccactga aattattcag tgacaaatca agctgcctaa gcgaggaaat gtttgcaatg    240
cttgaaggaa tatgtccact aaattggttt ctactcaaaa tcagaacaga aagattacgc    300
aatctaccta aactttgagg gatttgattg tcaaggaggt tgttctctgc attcagcagt    360
gtaagtgagg ataaattaga gagggtagca ggcaagttcc cattcaaggc attattagaa    420
atgtcaagtg tcttaagcct agaaagggtt cctatttcat ttggtatagc ttcactaaac    480
ttattatgac taanggaaat ctcattgagc tctcttaagc tacccaaaga agcaggaacc    540
gtcaccagtg aaaaaagtta tgatctagga tcaaattttg aacctaaaaa accattcttg    600
gaattccacc ccaagaatta ggaagggagc canaaagatt gttattttga aaaaaaaga    660 aaagtgagaa aaaatgagtg agttaggctt actggtaaaa ggaccaaaaa aaggantttg    720
aaactnaaan ttaanccaat aaaacttaat ggnaataaca aanactttta nggaattctc    780
ttttnaacaa attnttnctt angncaaaaa anttaancaa aggnct                    826
```

```
<210> SEQ ID NO 24
<211> LENGTH: 571
<212> TYPE: DNA
<213> ORGANISM: Glycine max
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
```

-continued

<400> SEQUENCE: 24

```
tgggactggc tgtgactgat ctctctggtc taatctcttc cagctgctgg agaacttgat      60
gaacttctgg tcgtgctgat ggagaaggat caacacagtg caaagcgagc ttcaacgtgt     120
ttagcaactc gtcgccaact gtggatgcat ctctcatcaa gtctgcatca aaaacctcat     180
ttgtccactc ctctttgaca actgaggcaa cccactgagg caaatctagt ccattcatag     240
acaccccagg tgatttcctc gttaggagtt ctaacaagat aacaccaaga ctgtagatat     300
cagttttagt gtttgctttc ttgagctttg agagctcagg tgcccggtat cccaatgctt     360
cagctgtagc tatcacgttg gaattagcag cagttgacat caaccgagaa agaccaaaat     420
ctgcaatttt agcatttgna ttctcattaa acaacacaat gntggatgng anggtnccat     480
ggatgaaggt cttctnggna agnaagnaaa acaaagcacc gggccaaggn ttgggctaat     540
ttcaaccttg ggggcaaac naanaaatgt t                                     571
```

<210> SEQ ID NO 25
<211> LENGTH: 727
<212> TYPE: DNA
<213> ORGANISM: Glycine max
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (726)..(727)
<223> OTHER INFORMATION: n is a, c, g, or t

<400> SEQUENCE: 25

```
ttacaactag tgttatcgga gaatgaaaaa ttgaagaata ataagttcag ctataataaa      60
ctcgagggag gaaaaacaaa gaaattcatg ataaatagat ataacttatt aaatttaagg    120
ggtgtatttg cacaccctga attatagaga ttcttatatc tttgagaaaa taattaaatt    180
gggaaaaaag agataatgac tgattgagat ttgcctcaga attgttcgtt ttaatattgg    240
tacgaatcta atggttttat cctgaaagat gctcacaagt attgagggac taataaattg    300
tttataaact actactaaat gagatgagac tttaaggtgt actgaagcaa tatcatttaa    360
aaaatgacta ctcgtatttg tgttgagaaa atttattttc aatgaaaaga aaatatatac    420
atataagata aagtaattaa cataaccgaa aggaaataaa atgcaacatt ataaaaacta    480
caactatata aatgatatat acaactccta gcacatgcat tggattgtga attaattaaa    540
atgttgtatg gatggtaaaa attcaaaact aaaccccccca caatttaagt gacacagaat    600
ataattagcg gtggtctttt tacagaaacg acgagaacaa aggtgtcaaa ggaaaggaga    660
tggatgcatg tggtatgagc tcatncaatt ccaacctgtt gtggaccaaa gccgaagtcc    720
ttgacnn                                                              727
```

<210> SEQ ID NO 26
<211> LENGTH: 560
<212> TYPE: DNA
<213> ORGANISM: Glycine max
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature

```
<222> LOCATION: (542)..(542)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t

<400> SEQUENCE: 26
attacgcnag ctctatacga ctcactatag ggagacaagc ttgcatgcct gcaggtcgac      60
tctagaggat ccccgggtac cgagctcgaa ttcccaatgc agagcttcc ctatcgtggg     120 ccccacctat gaagaataca cccacgttga atacatgtt gttgttgttg dacgcgccca     180
gccgagagtg ccggtccacg agtatcccca acgtgcatgg cgcatgcgct tgaaacctag    240
tattcatctt cctgatggag gcagccacgt gtccgacaag gtcaatgttg ccgttttcgt    300
gaaaagggat gataatgaaa ggcaccatat tgtcttgggc gaggttgaaa atggcgtcgt    360
gcatgctctt gtaaggtgcc acgttgatgt agggaagaac cttgactggc ccacttgagt    420
tgttggagta gttttcgaag gcttgcatga tgtggttggt gttggggtaa ttcacagaca    480
agaattttct gngacccgtg tctatgtttt atgggaagga gaatgggtgc cttttcccca    540
cnagctngat naggnggact                                                 560

<210> SEQ ID NO 27
<211> LENGTH: 630
<212> TYPE: DNA
<213> ORGANISM: Glycine max
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t

<400> SEQUENCE: 27
actgcatgca tgcaagcaaa tttaacttta cacaacacac caccagagtg taagctgttt      60
cataaaaaat gattgtttcg ggctttcgga tcacaaggct tgtttagtat tcggtaagaa    120
agaaagaaat aggtgataaa taaagtggat agaaacataa aagaaaggaa taaagtaatg    180
aaaataaggg agaagtagaa taatggaaat agataagaaa tagaatggat tcgatagtat    240
atctagttta agagaaataa gaaaaaataa gaacaagaaa aaaaattgca ttttaattta    300
ttatttgtac tgtatcgatg attggcacga gattataagt ttttttttc gtgtttaccg    360 ttgaaggatt atatatcata ccatttgttt gtcaaccaac acggaacttt aagtctcttg    420
atgttcaaaa gcacttaaaa ctaaggaatt ttacatcata ttagtcgtct gtagactgat    480
acaggatttt aagcctatat atctagcatt gatccggttg gcaatcaata tcacattaat    540
gatcggtaaa ccattcatat aaccccttg attggtcaag aaatggcttt atgaatccca    600
ggattgagcc cagaancagg ngatactagn                                     630
```

```
<210> SEQ ID NO 28
<211> LENGTH: 756
<212> TYPE: DNA
<213> ORGANISM: Glycine max
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(502)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (752)..(752)
<223> OTHER INFORMATION: n is a, c, g, or t

<400> SEQUENCE: 28
attggcttaa cttgagtttc aactccttct ctggtccttt accagctagc ctaactcact      60
cattttctct cacttttctt tctcttcaaa ataacaatct ttntggctcc cttnctaact     120
gtgggggggg gaatancaag ggnggcttta ggctgcaaaa tttgatccta gatcataact     180
```

-continued

```
ttttcactgg tgacgttcct gcttctttgg gtagcttaag agagctcaat gagatttccc    240
ttagtcataa taagtttagt ggagctatac caaatgaaat aggaacccett tctaggctta    300 agacacttga catttctaat aatgccttga atgggaactt gcctgctacc ctctctaatt    360
tatcctcact tacactgctg aatgcagaga acaacctcct tgacaatcaa atccctcaaa    420
gtttaggtag attgcgtact ctttcctgtt ccgattttga gtagaaacca atttagtgga    480
catattcctt caagcatngc nnacatttcc tcgcttaggc agcttgattg tcactgaata    540
atttcaggtg gagaaattnc agtctncttt gacagtcagc gcagtctaaa tcttcttcaa    600
tggttnctac aataggcctc tcagggtctg gccccccttt gnttggccaa ggaaanttaa    660
cttaagctta tttggngggg aaanattcaa ctatgggggg acncggcccct ttaaacccca    720 gggnttttcc caggttcctt ccaagggngc anttgt                              756
```

<210> SEQ ID NO 29
<211> LENGTH: 566
<212> TYPE: DNA
<213> ORGANISM: Glycine max
<220> FEATURE:
<221> NAME/KEY: misc_feature
<222> LOCATION: (554)..(554)
<223> OTHER INFORMATION: n is a, c, g, or t

<400> SEQUENCE: 29

```
gacccttgtt ctatagaacc gaattcgagc tcggtacccg gggatcctct agagtcgacc     60
tgcaggcatg caagcttatt attactacta ctacttatct tcactccacc acactgtgtc    120
actaaaaccg gaaccatccc catacaaaat tctactgaag acaacatatc ccccaatatt    180
cccaatgcat cagcgttctc catgaaagtt gtcatttctt ttccattcaa agatccatca    240
ttgtggcgcc ttcccaccat cacaagatca tagtttcctt ccaaactatg cactgcttcc    300
aacacctcca ccccatcgtc caccgtaatc tcgtaccaac aaacgttacc aatgccatat    360
ttcatgctct tgaactcgtc aattaacccc tcgtccaaca tggtatcttc ctcttcctct    420
tcacgctctt ctcttgcaaa ataatttac aaccacacgg tttcttggtc acgataacaa    480
acctaaacaa gctaccctcg tatctgcacg ctccgcattc gaattcccaa tgccagagct    540
tccctatcgg gggncccacc tatgaa                                          566
```

<210> SEQ ID NO 30
<211> LENGTH: 673
<212> TYPE: DNA
<213> ORGANISM: Glycine max
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature

```
<222> LOCATION: (494)..(494)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (637)..(638)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (672)..(673)
<223> OTHER INFORMATION: n is a, c, g, or t

<400> SEQUENCE: 30
gggactggct gtgactgatc tctctggtct aatctcttcc agctgctgga gaacttgatg      60
aacttctggt cgtgctgatg gagaaggatc aacacagtgc aaagcgagct tcaacgtgtt     120
tagcaactcg tcgccaactg tggatgcatc tctcatcaag tctgcatcaa aaacctcatt     180
tgtccactcc tctttgacaa ctgaggcaac ccactgaggc aaatctagtc cattcataga     240
caccccaggt gatttcctcg ttaggagttc taacaagata acaccaagac tgtagatatc     300
agttttagtg tttgctttct tgagcttttg agaagctcag gtgcccggta tcccaaatgc     360
ttccagctgt agcttatcac cgttgggaat taagcagcaa gttggacatt caacccggag     420
naaaagaccc aaaaattttg caaattttta agcaatttng gnanttcttn aatcaaggcc     480
aaccaccaat tggnttggga atggtggaag ggtttcccca atggtaattg gaagggtttc     540
ttccctnggg gaaatggaa agggcaana aacaaaggc ccaacngggg ccccaaaggt     600
nttttggggg cctattttt tncnaatncc ctttggnngg ggncccaaat tcnaaantgg     660
aaattggntt tnn                                                        673
```

```
<210> SEQ ID NO 31
<211> LENGTH: 736
<212> TYPE: DNA
<213> ORGANISM: Glycine max
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (627)..(628)
<223> OTHER INFORMATION: n is a, c, g, or t
<220> FEATURE:
<221> NAME/KEY: misc_feature
<222> LOCATION: (633)..(634)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t
<220> FEATURE:
<221> NAME/KEY: misc_feature
```

<222> LOCATION: (699)..(699)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (728)..(729)
<223> OTHER INFORMATION: n is a, c, g, or t

<400> SEQUENCE: 31

```
gttgnntagn tgcactatag aatncgaatt caatttaaac attttaattt ttttgtcttt      60
gtattctatt ttttcataaa ttctaatctt gctaataatt tcaattcata ttaagatcgg     120
taaatagaaa atctagaaaa aaaaacaaaa aaagtatttt tttttcattg attttatttt     180
caattgattt gtcactaaca aactgattcc tcttaaatct cacaaaagta catgtcgata     240
taaatatgag attataaatt catgatatct attttcgatt tttacatata atgttttttt     300
tatcttttt agttcctaat aagcattttt aaatgtctta tgttcctact ttgcatatca     360
gggacccatt aatgggacga ggtcactgcg agcatgaaca acgtgtcttt cgtctcccga     420
acaacgtgcc atcttgcagg ctcaccacct cggaatccct ggagtggtca ccactgattt     480
tccgggaaaa gcccgccggt gaaagtttga ttacaccggc aatgtgagcc ggtcgctgtg     540
gcaaccctgg tnccgggaca aangcacacc aagttgnaan tttgggtccg aggggngcca     600
naattggggt tgcanggata ctaagcnntt ggnnacttnc ctggnnaacc caccccctaat    660
nccatntttc aatggggnac cnaatttctt acaattggnt gcaananggg nttttngggn    720
aacctttnna ccccca                                                    736
```

<210> SEQ ID NO 32
<211> LENGTH: 566
<212> TYPE: DNA
<213> ORGANISM: Glycine max
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t -continued

<400> SEQUENCE: 32

```
gaccnnagac gctactatag ggagacaagc tattcgaagg ggaactgaga acgatccaaa      60
gcactccaag aaacagagag tttcacattg tttgttgtgt acataatgaa gcaaacgtgc     120
gtggcatcac tgccttatta aagagtgcaa acccagtgca agagagcccc atatgcgtct     180
acgcagtcca ccttatcgag ctcgtgggga aaagtgcacc cattctcctt cccataaaac     240
atagacacgg tcgcagaaaa ttcttgtctg tgaattaccc caacaccaac cacatcatgc     300
aagccttcga aaactactcc aacaactcaa gtgggccagt caaggttctt ccctacatca     360
acgtggcacc ttacaagagc atgcacgacg ccattttcaa cctcgcccaa gacaatatgg     420
tgcctttcat tatcatccct tttcacgaaa acggcaacat tgaccttgtc ggacacgtgg     480
ctgcctccat caggaagatg aatactaggt ttcaagcgca tgcgccatgc cgttggggat     540
actcgnggcc ggnactctng gtgggn                                          566
```

<210> SEQ ID NO 33
<211> LENGTH: 614
<212> TYPE: DNA
<213> ORGANISM: Glycine max
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (558)..(559)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t

```
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (593)..(593)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t

<400> SEQUENCE: 33
acaacaagca acgaacagct tttaacctta aactaggcaa atgccaatat taaacaacaa      60
ataattaaaa ttgtaaggct ggtcgagtat aaattaaaca aaaggccctc tattcaaacc     120
ttcatatatc atacctgntt ttaattaacg cggactactt tttcatataa aaaaaagatc     180
attagaggat taatttaaag cgntttagtt tttaattacc aaagagtata attattatta     240
ggcgctttgg cccacaatca atcacctaaa caagaaaaag aaaaagaaaa aaaaaggcaa     300
attggactaa tgcaaaagtg gcacaatctt tgncttgaac tctttaatta gcaacaaatn     360
atactcttct gcacaaatca caagaatacc ttacatgaaa agaatggnaa tntgacgggt     420
tacattaaat tatatgcagg tttctgcagg gaatcaattn tcaagaattt aaggggggt      480 gggaattttc aatagctagc ttgactagca aagggaaaga ataaaggnaa aangcttctt     540
ggctnggcct tttgggannng gnatccttt ngctaaaccg gaaanggnta tangaatggg     600
aaaggagana atcg                                                      614

<210> SEQ ID NO 34
<211> LENGTH: 602
<212> TYPE: DNA
<213> ORGANISM: Glycine max
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t

<400> SEQUENCE: 34
aggctagctg gtaaaggacc agagaaggat ttgaaactca agttaagcca ataaagctta      60
gtggaattag caagactata agggattgct cctgtgagca agttgttgct gaggtcaaga    120
gactgaagca aagggcagaa acctaaagaa agaggtatgg aacctgtaag cctattgttg    180
aataactgaa cccctctaag gttgggaaga agtcccaaag ttgaagggat tgaaccacca    240
atttggttat catgaagact aagcttcctg aggccttgaa gttggccaat tttggcggtg    300
attcgacccc tcaaacccct tccaaggaag ctggatcaca ataacctgtcc ctgagcacac    360
```

```
ttgattccaa cccaacctcc ggaacaagct ccatagccac tggcattcca gctcccgcaa    420
gaacccttct ggatcagcca actcttgctt gaaagcttat cacatgtacc tctctacaga    480
taggagggtg cttcttccct ttcactggnc tacctcttcg ggaataagcc acctaatgag    540
aaagaaagan ctgggatagc taactctaca tagnctcaag gcnagagata attagggaaa    600 ng                                                                  602
```

```
<210> SEQ ID NO 35
<211> LENGTH: 644
<212> TYPE: DNA
<213> ORGANISM: Glycine max
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t

<400> SEQUENCE: 35
ggaattttga agagaagtaa agtgagagaa aatgantgan nnaggctagc tggtaaagga     60
ccagagaagg atttgaaact caagttaagc caataaagct tagtggaatt agcaagacta    120
taagggattg ctcctgtgag caagttgttg ctgaggtcaa gagactgaag caaagggcag    180
aaacctaaag aaagaggtat ggaacctgta agcctattgt tgaataactg aaccccctcta   240 aggttgggaa gaagtcccaa agttgaaggg attgaaccac caatttggtt atcatgaaga    300
ctaagcttcc tgaggccttg aagttggcca attttggcgg tgattcgacc cctcaaaccc    360
ttccaaggaa gctggatcac aataaccgtgt ccctgagcac acttgattcc aacccaacct    420
ccggaacaag ctccatagcc actggcattc cagctcccgc aagaacccctt ctggatcagc    480 caactcttgc ttgaaagctt atcacatgta cctctctaca gataggaggg tgcttcttcc    540
ctttcactgg nctacctctt cgggaataag ccacctaatg agaaagaaag anctgggata    600
gctaactcta catagnctca aggcnagaga taattaggga aang                     644
```

```
<210> SEQ ID NO 36
<211> LENGTH: 748
<212> TYPE: DNA
<213> ORGANISM: Glycine max
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
```

<222> LOCATION: (632)..(632)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t

<400> SEQUENCE: 36

```
attggcttaa cttgagtttc aactccttct ctggtccttt accagctagc ctaactcact      60
cattttctct cactttcttt tctcttcaaa ataacaatct ttctggctcc cttcctaact     120
cttggggtgg gaattccaag aatggcttct ttaggcttca aaatttgatc ctagatcata     180
acttttcac tggtgacgtt cctgcttctt tgggtagctt aagagagctc aatgagattt      240
cccttagtca taataagttt aatggagctg taccaaatga aataggaacc ctttctaggc     300
ttaagacact tgacatttct aataatgcct tgaatgggaa cttgcctgct accctctcta     360
atttatcctc acttacactg ctgaatgcag agaacaacct ccttgacaat caaatccctc     420
aaagtttagg tagattgcgt aatctttctg ttctgatttt gggtagaaac caatttagtg     480
gacatattcc ttcaagcatt gcaaacattt cctcgcttag gcagcttgat ttgcactgaa     540
taatttcagt ggagaaattc cagtctcctt tgacagtcaa gcgcaagtct aaatctcttc     600
aatgttcct acaatagcct ctcanggtct gncccccctc tgcttgccaa gaaatttaac      660
tcaagctcat ttgtgggaaa tattcaacta tgtgggacag nccttcaacc ccatgttttn     720
ccaagcttca tacaaggagc atggccct                                         748
```

<210> SEQ ID NO 37
<211> LENGTH: 563
<212> TYPE: DNA
<213> ORGANISM: Glycine max

<400> SEQUENCE: 37

```
ctggctgtga ctgatctctc tggtctaatc tcttccagct gctggagaac ttgatgaact      60
tctggtcgtg ctgatggaga aggatcaaca cagtgcaaag cgagcttcaa cgtgtttagc     120
aactcgtcgc caactgtgga tgcatctctc atcaagtctg catcaaaaac ctcatttgtc     180
cactcctctt tgacaactga ggcaacccac tgaggcaaat ctagtccatt catagacacc     240
ccaggtgatt cctcgttag gagttctaac aagataacac caagactgta gatatcagtt      300
ttagtgtttg ctttcttgag ctttgagagc tcaggtgccc ggtatcccaa tgctccagct     360
gtagctatca cgttggaatt agcagcagtt gacatcaacc cgagaaagac caaaatctgc     420
aattttagca tttgtattct catcaagcaa cacattgctg gatgtgaggt tcccatgtat     480
gatgttctcc tgggaatgaa ggcagaacaa gccacggcca agcttggcta tttcatcctt     540
gtggccaatc aatgaatggt cat                                              563
```

<210> SEQ ID NO 38
<211> LENGTH: 623
<212> TYPE: DNA
<213> ORGANISM: Glycine max
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t

<400> SEQUENCE: 38

```
gattttgcac atctacttga gtaggcttca catgattccg tgtattactt ttattttggt    60
atatatacca tgtggagtat agtatcactt tttgtcctac aaccacattt tatgagactt   120
gcattttatg tgacatgaac ataaaaaata atgaaaaaga aaatgtcaca tatatatgat   180
acaatctttt taaaagtcaa tttgaataat ttttcatcag gaggaaaaag aagagagaaa   240
atgaattaag tttcttctaa aaattaaaat caacttataa aagaaaaaa ctttaatgaa    300
aaaaattcaa aaagaaaaag aataaaatga tcaatagcct ttaggtttaa gcacaaggtg   360
aatccaaata aagaccccaa aagatagtac agaacccaac aatggtaaaa tctagaaata   420
tacatgtaaa gactgcattt atagaccatc atgactagca aatgcttaaa ggcacataga   480
tgaattaatc tatgcaacaa aatctgnccc aagttttttt tangcaagga aaatcatatc   540
attttattaa ggataactga gaggaccaat ggtgtaatca attgaaatca tgcgaggctt   600
acatgaaatc tgtcaccaag tac                                            623
```

<210> SEQ ID NO 39
<211> LENGTH: 785
<212> TYPE: DNA
<213> ORGANISM: Glycine max
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (767)..(767)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (781)..(782)
<223> OTHER INFORMATION: n is a, c, g, or t

<400> SEQUENCE: 39

```
caattaggaa ataaatatat tgaaaagaat tggtagtcag ttcaatgaaa gtgaggtcct    60
caaacaactt gatgcagcan ctgtatgata caaaatatat taataactac accagcagaa   120
aaatataggt caatctatat ttgggaacca aataatattt aatttgtatc tgatagactc   180
aagaaattat aactaatttg gaagaaatgg atacctagta ttattaaaac accaaaacac   240
agggcagatt atagtagcta aagaggaaga agctaactag tcaaagtgtc acactattca   300
acactacaaa ggaccaatcc cctttagag agcctgacct ttctcaccca agagctaccc    360
aagagaatac acccctctc ctccatatcc cctcccatat aacacaatcc tcaccaacta    420
agcacctacc tgacaattcc ctcctaacca actctctgct catcagggtt gattctcttc   480
tctttccaag actttgggct tttgttttga ctaagccaaa tttctatctg ctggcctggt   540
ccaacagtat cttttacaga caagtttaca aaatattcgt atttgttaga atttattgat   600
```

```
attcctatta tggtccccac tgtgtgcaaa catttagaaa ctaatattac aattaacagt    660
ttttggtgaa tgcagcaaaa ctaaatatat ttgatataga aatcaacaaa ctgaaaaatt    720
atatngcaag gncaattgga aaagaaaatt gatacccctt ttgnggnaat aaatatantg    780 nntac                                                                785
```

```
<210> SEQ ID NO 40
<211> LENGTH: 640
<212> TYPE: DNA
<213> ORGANISM: Glycine max
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t

<400> SEQUENCE: 40
tggaaggcgt ccttcaattc aatcacaaag tctaaatcaa agacgagggg gctgaaatca     60
tgggggacat tgacaacgta aggtaaccac taattaatta accactaata ttatcccatt    120
aatatcccat taagagataa tacatataga gccaataaat aagcatctta acaagacaaa    180
taaattatcc attattccagc ttatgcccat ggtggtatta gaagtttagg aaaaaaaaat    240
tcatcatttg gcaattttgg gctcattagc ttgaattggt tacaaggtgt ggtatggact    300
tttttctttt cttttctcta aattcttcct tctatgatat acttttggtc aacttaaact    360
caatttctta tagctcaata ttttggattt agattggaaa tatctaaaag ncacttaaat    420
tttatattta caaaaaaaaa aaaagcatcg ntcttttctt tttataaca aaggggatc     480 aaaatcactc ttttatgaa tccgcattat ccttnataat aattaacctc cactgggatt    540
taaagggnga ttaattaaat ccggaggcca tggaaggata tggggaacc taatctaaaa    600 ntncatcctc aaccctaang ggaaaataaa ggaatngggg                          640
```

```
<210> SEQ ID NO 41
<211> LENGTH: 808
<212> TYPE: DNA
<213> ORGANISM: Glycine max
<220> FEATURE:
<221> NAME/KEY: misc_feature
<222> LOCATION: (83)..(83)
<223> OTHER INFORMATION: n is a, c, g, or t
```

```
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t

<400> SEQUENCE: 41
cttttgacac tatgaatacg aattcaaata ttaaatattt ttattttttg tctttgtatt      60
ctattttttc ataaattcta atnttgctaa taatttcaat tcatattaag atcggtaaat     120
agaaaatcta gaaaaaaaaa caaaaaaagt attttttttt cattgatttt attttcaatt    180
gatttgtcac taacaaactg attcctctta aatctcacaa aagtacatgt cgatataaat    240
atgagattat aaattcatga tatctatttt cgattttttac atataatgtt ttttttatct    300
tttttagttc ctaataagca tttttaaatg tcttatgttc ctactttgca tatcagggac    360
ccattaatgg gacgaggttc actgcgagca tgaacaacgt gtctttcgtt ctcccgaaca    420
acgtgtccat cttgcaggct caccacctcg gaatccctgg agtgttcacc actgattttc    480
cggggaagcc gccggtgaag tttgattaca ccggcaatgt gagccgttcg ctgtggcaac    540
ctgttcccgg gacaaaggca cacaagttga agtttgggtc cgagggtgca gattgtgttg    600
caggatacta gcattgtcac tcctgagaac caccctatcc atcttcatgg gtcgatttct    660
acattgttgc agagggtttc gggaacttcg acccaaagaa agatccgcga aattcaacct    720
tggtggatcc cctttgaaaa acacagtggc tggcctgtaa atggatgggc aagtattcga    780
tttgggggct gataacccna gtaaatnt                                        808

<210> SEQ ID NO 42
<211> LENGTH: 605
<212> TYPE: DNA
<213> ORGANISM: Glycine max
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
```

```
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (602)..(603)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t

<400> SEQUENCE: 42
ctcccgggtc caagtaata ggcccctcag agccaaaaca ttggggggc taattttcc       60 tagaacactg acttctgatt caaattctct atgacctta gtgatctttt ccctcaatct    120
ctttactgca acttgacttc catcctccaa aatagcctta taaacagntc cataggtgct   180
ctttcccatg atctcagctg gtgcacacaa gagatcatca gctgtaaaag ccattggtcc   240
atcaaaatgg actagtttcc ctccagcctc cccacctgct tcaacatcac caccagcaac   300
tggagggact cctttttctg cctcatagtg gccgctctac cctcggtggc ttggccgntc   360
ccggccttag atgntgatct ctttctgatc aggcagaaaa gcaggacaca acaaagnata   420
atcaggacta cgaggagaac tcctgctact atgagaatta tgnctttggg gcttagcttc   480
ctatgatggg gatggttnga cacttcanga ggggggcaa tgactccctg gganggagct   540
tgggaaagac atgggggtga aggnctgnac ccacataggn gaaaaattcc cacaaangag   600 cnngn                                                                605

<210> SEQ ID NO 43
<211> LENGTH: 275
<212> TYPE: DNA
<213> ORGANISM: Glycine max
<220> FEATURE:
<221> NAME/KEY: misc_feature
<222> LOCATION: (225)..(225)
<223> OTHER INFORMATION: n is a, c, g, or t

<400> SEQUENCE: 43
ctgaacggaa gtgactgcgt ttgtgtcggt tgtaagcagg gagtggaggc attataggtc     60
tcggttttgc tctttactcc tttggcacga tggtgagaat gcttattgtg gtgattcggt    120
gatttgtatt cgagtatggc ggttgtagtg gtgttgtcga aggcagcgtt ttgggcggat    180
tggtacgcac gcgccgccat gtagtagcgg gaaggtggct ggtcnccggt gattaagacg    240
tcggcggttt gcccggggcc cactatgagg acttt                                275

<210> SEQ ID NO 44
<211> LENGTH: 632
<212> TYPE: DNA
<213> ORGANISM: Glycine max
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
```

<220> FEATURE:
<221> NAME/KEY: misc_feature
<222> LOCATION: (632)..(632)
<223> OTHER INFORMATION: n is a, c, g, or t

<400> SEQUENCE: 44

| | | | | | |
|---|---|---|---|---|---|
| tgtatataat | taaaatgagt | ttaatattta | tgtattaata | gtataaaatt | tatcatacat | 60 |
| gatgaatggt | gaaattttga | attatgatta | aataattata | taaaaaaatt | tacatgatga | 120 |
| atgaataact | ttttttttct | caattaaaat | tatgatcctt | tgtcgatatg | ttttactgtg | 180 |
| tcgaccttt  | ttttcggggg | agaggggacc | agtaggagaa | gtagtattta | gtaaaagaag | 240 |
| ggagagagaa | gttgacttat | cctttaatta | gtttagagaa | aattagacga | gaaggaaaaa | 300 |
| aaataggcga | aagtcacttt | ttcttctat | ctctaccaag | aatgttgatg | aaaaagtggg | 360 |
| gagcagaatt | ttaaattttt | attttcatat | ttatccttct | ccacatttt  | ggtttcttcc | 420 |
| atttttttat | aaaatgattt | attttagggc | ataggtaact | tttcaatttt | tttcattcta | 480 |
| ttcgatcaaa | taaatagaaa | aataatttac | ttttctttct | tttaaccttt | ttcatatttc | 540 |
| tctcataacg | accacttatt | aattacctct | tttnccccac | ttttttgctat | ncaaatctat | 600 |
| cttttgaattt | cttccttttc | attttggtct | cn         |            |            | 632 |

<210> SEQ ID NO 45
<211> LENGTH: 650
<212> TYPE: DNA
<213> ORGANISM: Glycine max
<220> FEATURE:
<221> NAME/KEY: misc_feature
<222> LOCATION: (573)..(573)
<223> OTHER INFORMATION: n is a, c, g, or t

<400> SEQUENCE: 45

| | | | | | |
|---|---|---|---|---|---|
| ttcacagaca | tagcaaaatt | ctgaagtaag | aagcaagttc | acgtgtgatg | gcgaaaccca | 60 |
| ttatagaata | tgttagactg | aaaggtaaca | aattaaaata | tgttttattg | cagaaaccat | 120 |
| aaactaataa | acctttgggg | tagatagaaa | agtgataaat | catacataat | aataactgaa | 180 |
| atactcagct | tttaatcaat | ttaattcaat | atatatctat | ttttgaattt | ttcaaagaga | 240 |
| tgcttagcta | ggggaggaaac | ctaatttagt | ataaaaaaa | gaaacaaatt | aaaaacataa | 300 |
| attgccattg | aatgcctctt | aaaatattcc | gatccattga | tgtctacata | ataatatata | 360 |
| ttattgatat | aataaccgat | tgaataaaat | ggatatacct | attacgtaat | agcagatttg | 420 |
| tctacgcaaa | agagacagtc | aaaggtgcta | attagaaatt | aatcgcccca | taataaaatt | 480 |
| ctaaaccttt | gaaagataa  | atcaattctc | aaaaagattt | attttactta | tctcagtacc | 540 |
| atgcaccatg | gatcatctta | ctggtctggt | tangaatttt | caaagctacg | ccacaaattg | 600 |
| aaattgggct | aaaaatcaaa | catgcatggt | gtcacaacta | tattactagt |            | 650 |

<210> SEQ ID NO 46
<211> LENGTH: 628
<212> TYPE: DNA
<213> ORGANISM: Glycine max
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t

```
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t

<400> SEQUENCE: 46
gaatgcacat tttataaacg tgttgatcct ctccccgnng ggggaccaat taataaggta      60
ccctgttgcc cctaggggac attggatggc catcagatgg tgcatataca caccaaagtt    120
tatacagcat tatagtgact ttcaacctcc tcactccgag gtccccatat attctctcta    180
ttgaacttgt aaagactaat gaacttatga agactatcac tgaaacccac tatggaagcc    240
ccagtagtaa aatggncatg catgctcacc aaaagtttat acagcattat agcgacatac    300
gacctcactc ccaggnccac atgctctatn gaacttctaa agctatctcn gaaccctatt    360
atagcttcat gagggtaaca tgcattttag cgacttagaa aactacatat cattgagcgt    420
gatcnttaag aaggcctcat tttgacacaa agaacatga tggatttgcc tttatattcg    480
gttactaacc ttgatagcta ttttggncag agagaaaaat attgacatgc ccgnggaatc    540
aaaaggtaga taatnattaa agagataaag aactatcccc ttgctagggg naaaaaaaaa   600
ntatatccct atttaaataa aanccatc                                      628

<210> SEQ ID NO 47
<211> LENGTH: 736
<212> TYPE: DNA
<213> ORGANISM: Glycine max
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t

<400> SEQUENCE: 47
tggtgtatat aattaaaatg agtttaatat ttatgtatta atagtataaa atttatcata      60
catgatgaat ggtgaaattt tgaattatga ttaaataatt atataaaaaa atttacatga    120
```

-continued

```
tgaatgaata actttttttt tctcaattaa aattatgatc ctttgtcgat atgttttact        180
gtgtcgacct ttttttttcgg gggagagggg accagtagga gaagtagtat ttagtaaaag       240
aagggagaga gaagttgact tatcctttaa ttagtttaga gaaaattaga cgagaaggaa        300
aaaaaatagg cgaaagtcac tttttctttc tatctctacc aagaatgttg atgaaaaagt       360
ggggagcaga attttaaatt tttattttca tatttatcct tctccacatt tttgttttct       420 tccattttt tataaaatga tttattttag ggcatagtta acttttcaat tttttttcatt       480 tctattcgat caaataaata gaaaaataat ttacttttct ttcttttaac cttttcatat       540
ttctctcata acgaacaact tattaattta cctcttttcc cccactttg tctatccaaa        600 ttctatcttt gaattttctt cctttcatt ttggttctca acccaaataa agaagaacga        660
gtttggataa atcataaagg ttatataccc tataantgga agaacattta aatggtccaa       720
ngggccttaa aattct                                                        736
```

<210> SEQ ID NO 48
<211> LENGTH: 695
<212> TYPE: DNA
<213> ORGANISM: Glycine max
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t

```
-continued

<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (615)..(616)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (639)..(640)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (653)..(655)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (682)..(686)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
```

```
<220> FEATURE:
<221> NAME/KEY: misc_feature
<222> LOCATION: (695)..(695)
<223> OTHER INFORMATION: n is a, c, g, or t

<400> SEQUENCE: 48
atgccagagc tttccttatc gtggccccac ctatgaagaa tacacccacg ttgaaataca      60
tgttgttgtt gttggacgcg cccagcccga gagtgccggt ccacgagtat ccccaacgtg     120
catggcgcat gcgcttgaaa cctagtattc atcttcctga tggaggcagc cacgtgtccg     180
acaaggtcaa tgttgccgtt ttcgtgaaaa gggatgataa tgaaaggcac catattgtct     240
tgggcgaggt tgaaaatggc gtcgtgcatg ctcttgtaag gtgccacgtt gatgtaggga     300
agaaccttga ctggcccact tgagttgttg gagtagtttt cgaaggcttg catgatgtgg     360
ttggtgttgg ggtaattcac agacaagaat tttctgcgac cgtgtctatg ttttatggga     420
aggagaatgg gtgcactttt cccacgagct cgataaaggt ggactgcgta naccatatgg     480
gctctnttgc actgggttgc actcttctaa taanggcagn gatgccncnc nccgtttgct     540
tnattatgta cncaacaaac aatgngaaac tctctgnttn ttgggagngc tttggatcgn     600
tctcanntnc ccttnnaata ancttttntnn gngnacttnn agggcgangc ttnnncnata     660
tgntaaccaa gggngntacn annnnnggnt ntaan                                 695

<210> SEQ ID NO 49
<211> LENGTH: 625
<212> TYPE: DNA
<213> ORGANISM: Glycine max
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (611)..(611)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t

<400> SEQUENCE: 49
tttcccacaa tctttaatct tgctaataat ttcaattcat attaagatcg gaaaatagaa      60
aatctataaa aaaaaacaaa aaagtatttt tttttcatt gattttattt tcaattgatt     120
tgtcactaac aaactgattc ctcttaaatc tcacaaaagt acatgtcgat ataaatatga     180
```

```
gattataaat tcatgatatc tattttcgat ttttacatat aatgtttttt ttatcttttt      240
tagttcctaa taagcatttt taaatggctt atgttcctac tttgcatatc agggacccat      300
taatgggacg aggttcactg cgagcatgaa caacgtggct ttcgttctcc cgaacaacgt      360
gtccatcttg caggctcacc acctcggaat ccctggagtg ntcaccactg attttccggg      420
gaagccgccg gtgaagttng attacacccg gcaatgtgag ccgntcgctg ggcaacctg       480 ntcccgggac aaaggcacac aagttgaagt ttgggtcgag ggngcagatt ggggntgcan      540
gatactagca ttgcactcct gagaaccacc ctatccatct tcatggggac caattctaca      600
ttggtgcaga nggttccggg aacnc                                            625

<210> SEQ ID NO 50
<211> LENGTH: 621
<212> TYPE: DNA
<213> ORGANISM: Glycine max

<400> SEQUENCE: 50
actggtgtac gatttagtgt tactagctat cccatgtaat aaatatataa atcttgaatc       60
acaaggaatg atgcaatata tggttcctct aatagtaagt tatcccacca aatctgaata      120
taattaagaa gttgtattcg tctgaatgtt gtgtctaaaa gggttgattg atgaatgatg      180
gctacatgtg agagtttgat aacaacagct agctagccat tagccaagcc actaactaga      240
cattagtttt ggttggttgt cagacaaacc gttagacctg agaacgaaag cgtattaaac      300
aaaagatgat atgtagactt ttaatataaa aagagatgga gaaaccaaat tgagatttga      360
taggtgaact ataaatcatg acagtgcatt agacaagttg gtagagtttg ttactaactc      420
atcagattct taagaaaggc aaaaatagaa actacaccac atgtcgctag cgataacgtg      480
caatttataa ataaataatg gcttcatttt catggttagt tataaattaa tgggtcacaa      540
ttcttaattt attaggaacg tatacttcat tttgagagtg tataaagttg gaagaagaaa      600
agggatatag aaagaataaa a                                                621

<210> SEQ ID NO 51
<211> LENGTH: 480
<212> TYPE: DNA
<213> ORGANISM: Glycine max
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
```

```
<220> FEATURE:
<221> NAME/KEY: misc_feature
<222> LOCATION: (464)..(464)
<223> OTHER INFORMATION: n is a, c, g, or t

<400> SEQUENCE: 51
aagctccgcn cggggaacct nnagagtcta cctgaatccc caagntngaa cgaatacttg    60
ccaacacaaa tacgggcgat gggaaacatc tgaagaccgc tccaaagcgc cncatactaa   120
attgnnagga aaatttatat ctgacctttc atgggtgggg ggtgcatctg ctataaggaa   180
gggttcattc tggcaagat ctgtggaaaa caatattggg gatcaaattt tagggagtga   240
tgctacaacc tcttcattat acatggattc tgaaataagt ggtgtgaact ttaaagtgaa   300
cgaagacggc atgcaaatgc ctggtattca tctagttgat ttatttgaga ctgacaccaa   360
tacaagcggc gataaacatg attcccacta tgatgaagng ccatcatctt atgggtttga   420
gggcttacga cgatccaaac gtaggaacat acaacctgaa ccgntactct gattggggga   480

<210> SEQ ID NO 52
<211> LENGTH: 480
<212> TYPE: DNA
<213> ORGANISM: Glycine max
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t

<400> SEQUENCE: 52
aagctccgcn cggggaacct nnagagtcta cctgaatccc caagntngaa cgaatacttg    60
ccaacacaaa tacgggcgat gggaaacatc tgaagaccgc tccaaagcgc cncatactaa   120
attgnnagga aaatttatat ctgacctttc atgggtgggg ggtgcatctg ctataaggaa   180
gggttcattc tggcaagat ctgtggaaaa caatattggg gatcaaattt tagggagtga   240
tgctacaacc tcttcattat acatggattc tgaaataagt ggtgtgaact ttaaagtgaa   300
cgaagacggc atgcaaatgc ctggtattca tctagttgat ttatttgaga ctgacaccaa   360
tacaagcggc gataaacatg attcccacta tgatgaagng ccatcatctt atgggtttga   420
gggcttacga cgatccaaac gtaggaacat acaacctgaa ccgntactct gattggggga   480
```

```
<210> SEQ ID NO 53
<211> LENGTH: 736
<212> TYPE: DNA
<213> ORGANISM: Glycine max
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (734)..(735)
<223> OTHER INFORMATION: n is a, c, g, or t

<400> SEQUENCE: 53
aatttattta gttgatataa ccactttcaa aaatctgact tacaagactc tttagaattc    60
ataatagtga cacttgatta agttagatta gactttataa aacacgagtt tgattttttt   120
tttaataata attaaggttc tagcttatat atattatata gttgatatag actactttca   180
aaagtctgac ttaaaagtct ctttagtata cataataata taacctttta atttagttaa   240
aaaatttgtc cctaaataaa ttaataaatc caaacttata tacaagttaa taggcttaag   300
tcttaaaaaa ataatatata tatatatata taaagcatta aaacatttca atgaaaacaa   360
tataataata ataataataa atatattatt gttattaatt catagatttt attattacta   420
ttatagaata atttgtgtgt atatatataa atatatagag agagagaggg tcattttata   480
tgagtgagaa aatttaaata ttattatgaa ttttcaaaat taaaatcaca tgccatatga   540
ttttcttaaa aaattacgta acttttttttt ttacaaaagt aatcatatgg ttttaaaaac   600
taatttaaat aacttatata taactatatc agntaaaatt ngggtcataa aataagtata   660
tcagntattt tacaaaaatt ataagtnttc ataaataaat accaaatgat agtcccaggn   720
gatgggncag cttnng                                                    736

<210> SEQ ID NO 54
<211> LENGTH: 642
<212> TYPE: DNA
<213> ORGANISM: Glycine max
<220> FEATURE:
<221> NAME/KEY: misc_feature
<222> LOCATION: (573)..(573)
<223> OTHER INFORMATION: n is a, c, g, or t

<400> SEQUENCE: 54
ttaactttac acaacacacc accagagtgt aagctgtttc ataaaaaatg attgtttcgg    60
gctttcggat cacaaggctt gtttagtatt cggtaagaaa gaaagaaata ggtgataaat   120
aaagtggata gaaacataaa agaaaggaat aaagtaatga aaataaggga gaagtagaat   180
aatggaaata gataagaaat agaatggatt cgatagtata tctagtttaa gagaaataag   240
```

```
aaaaaataag aacaagaaaa aaaattgcat tttaatttat tatttgtact gtatcgatga      300
ttggcacgag attataagtt ttttttttcg tgtttacgtt gaaggattat atatcatacc      360
atttgtttgt caaccaacac ggaactttaa gtctcttgat gttcaaaagc acttaaaact      420
aaggaatttt acatcatatt agtcgctgta gactgataca ggattttaag cctatatatc      480
tagcattgat cgggtgtcaa tcaatatcac attaatgatc ggtaaaccat tcatataacc      540
cctttgattg gtcaagaaat ggctttatga atnccagga ttgagcccag aagacaggtg      600
atactaggtt caattcatgg ttttaggata ggctcgtaaa cc                          642
```

```
<210> SEQ ID NO 55
<211> LENGTH: 659
<212> TYPE: DNA
<213> ORGANISM: Glycine max
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t

<400> SEQUENCE: 55
aaaaggacct aaaagcaaaa agaaaattga gtatccttag gaattaaaaa tattccaata       60
aaaataaaat aaagatccaa atgatagtgg gataaccgaa gaggaatgtc tttcaaccac      120
tgcctgaccg ccaccactgc caacagccta gtatcaaccg aatccacata taccaacaat      180
cttcagacaa acacttctaa gttggtgctg aagagacaat atctcatggg tagatcaaat      240
taagagtgct accaataaca aaatcgggat catttgacta acaaacagtt atgtgcattg      300
gatgttctac catagtacat tgctttatgt gaaattcttt taattattca atattgacat      360
gntcttatat atatatatat atatatatat atatatatat atatacgagg gattgnatta      420
```

```
tctctgaaaa aagattttat cataaaatca taatgatttc tcataatgna tctttacatt    480
ttaaaggtag ataaataaaa ttgatttaaa tnggnagata taattaaaat acataattaa    540
tatgactttt aaccaaattg atatataaac acttaaaaaa aagttcatga acgnccgggg    600
ngnattggnt gggncaaaaa aaaattaata ctatcaacct aattaaaaat tatttatan    659
```

```
<210> SEQ ID NO 56
<211> LENGTH: 805
<212> TYPE: DNA
<213> ORGANISM: Glycine max
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (654)..(655)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (732)..(733)
<223> OTHER INFORMATION: n is a, c, g, or t
<220> FEATURE:
<221> NAME/KEY: misc_feature
<222> LOCATION: (739)..(740)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
```

```
<222> LOCATION: (744)..(744)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (782)..(783)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (795)..(796)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t

<400> SEQUENCE: 56
ccaatgccag agcttcccta tcgtgggccc cacctatgaa gaatacaccc acgttgaaat      60
acatgttgtt gttgttggac gcgcccagcc gagagtgccg gtccacgagt atccccaacg     120
tgcatggcgc atgcgcttga aacctagtat tcatcttcct gatggaggca gccacgtgtc     180
cgacaaggtc aatgttgccg ttttcgtgaa aagggatgat aatgaaaggc accatattgt     240
cttgggcgag gttgaaaatg gcgtcgtgca tgctcttgta aggtgccacg ttgatgtagg     300
gaagaacctt gactggccca cttgagttgt tggagtagtt ttcgaaggct tgcatgatgt     360
ggttggtgtt ggggtaattc acagacaaga attttctgcg accgtgtcta tgttttatgg     420
gaaggagaat gggtgcactt ttccccacga gctcgataag gtggactgcg tagacgcata     480
tggggctctc ttgcactggg ttgcactctt ctaataaggc agtgatgcca cgcacgtttg     540
ctttcattat gtacacaaca aaacaatgtg aaaactctct gtttcttgga ggtgctttgg     600
atcgttctcn agttcccctt cgaataagct ttctgcgtgn tacttcnagg ggcnnatgct     660
ttgtaccaat atgnttancc caagggngnt tnccattncn ggtctttact accacnacat     720
aacacccnat tnnttgaann gnanccnatc caacntctac naaancgtna tcaatnacnt     780
tnnattngat ttganncact ggccn                                           805

<210> SEQ ID NO 57
<211> LENGTH: 632
```

```
<212> TYPE: DNA
<213> ORGANISM: Glycine max

<400> SEQUENCE: 57
tttagaattc ataatagtga cacttgatta agttagatta gactttataa aacacgagtt      60
tgattttttt tttaataata attaaggttc tagcttatat atattatata gttgatatag     120
actactttca aaagtctgac ttaaaagtct ctttagtata cataataata taaccttta      180 atttagttaa aaaatttgtc cctaaataaa ttaataaatc caaacttata tacaagttaa     240
taggcttaag tcttaaaaaa ataatatata tatatatata taaagcatta aaacatttca     300
atgaaaacaa tataataata ataataataa atatattatt gttattaatt catagatttt     360
attattacta ttatagaata atttgtgtgt atatatataa atatatagag agagagaggg     420
tcattttata tgagtgagaa aatttaaata ttattatgaa ttttcaaaat taaaatcaca     480
tgccatatga ttttcttaaa aaattacgta actttttttt ttacaaaagt aatcatatgg     540
ttttaaaaac taatttaaat aacttatata taactatatc agttaaattt ggttcataaa     600
ataagtatat cagttatttt acaaaattat aa                                   632

<210> SEQ ID NO 58
<211> LENGTH: 437
<212> TYPE: DNA
<213> ORGANISM: Glycine max
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (404)..(405)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t

<400> SEQUENCE: 58
cttttgacac tatngaatac gaattcgaat gtcggagcgt gcagatacga gggtgagctt      60
gtttaggttt gttatcgtga acaagaaacc gtgtggttgt aaaattattt tgacaagaga     120
agagcgtgaa gaggaagagg aagataccat gttggacgag gggttaattg acgagttcaa     180
```

```
gagcatgaaa tatggcattg gtaacgtttg ttggtacgag attacggtgg acgatggggt    240
ggaggtgttg gaagcagtgc atagtttgga aggaaactat gatcttgtga tggtgggaag    300
gcgccacaat gatggatctt tgaatggaaa agaaatgaca actttcatgg agaacgctga    360
tgcattggga atattgtggg atatgttccc ttcnccsanc ntgnntggcn tngttccgct    420
tttttcgnct ntnngcc                                                   437
```

```
<210> SEQ ID NO 59
<211> LENGTH: 681
<212> TYPE: DNA
<213> ORGANISM: Glycine max
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t

<400> SEQUENCE: 59
```

```
ggnttcttta gggcttcaaa atttgatcct agatcataac ttttttcact ggtgacgttc     60
ctgcttcttt gggtagctta agagagctca atgagatttc ccttagtcat aataagttta   120
gtggagctat accaaatgaa ataggaaccc tttctaggct taagacactt gacatttcta   180
ataatgcctt gaatgggaac ttgcctgcta ccctctctaa tttatcctca cttacactgc   240
tgaatgcaga gaacaacctc cttgacaatc aaatccctca agtttaggt agattgcgta   300 atctttctgt tctgattttg agtagaaacc aatttagtgg acatattcct tcaagcattg   360
caaacatttc ctcgcttagg cagcttgatt tgcactgaat aatttcagtg gagaaattcc   420
agtctccttt gacagtcaag cgcagctaaa tctcttcaat ggttcctaca atagcctctc   480
agggtctgcc cccctctgct tggcaagaaa tttaactcaa gctcatttgt gggaaatatt   540
caactatgtg gggtacagcc ttcaacccca tggctttcca agctncatca caaggggca   600 ttggccccct cctgagnggc aaacatcacc atcataggaa gctaacccca aagacataat   660
tctcatagta nccaggaggt n                                              681
```

```
<210> SEQ ID NO 60
<211> LENGTH: 644
<212> TYPE: DNA
<213> ORGANISM: Glycine max
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t

<400> SEQUENCE: 60
```

```
acaacaagca acgaacagct tttaacctta aactaggcta atgccaatat taagaagaa     60
```

```
ataattaaaa ttgtaaggct ggtcgtgtat aaattaaaca aaaggccctc tattcaaacc    120
ttcatatatc atacctgttt ttaattaacg cggactactt tttcatataa aaaaaagatc    180
attagaggat taatttaaag cgttttagtt tttaattacc aaagagtata attattatta    240
ggcgctttgt cccacaatca atcacctaaa caagaaaaag aaaagaaaa aaaaagtcaa     300 attggactaa tgcaaaagtg gcacaatctt tgtcttgaac tctttaatta gcaacaaatt    360
atactcttct gcacaaatca caagaatacc ttacatgaaa agaatggtaa tttgacgggt    420
tacattaaat tatatgcagt tttctgcagg taattaattt tcaagaattt aagggtgggt    480
ggtaattttc aatagctagc ttgactagca aaggaaagaa taaaggtaaa atgcttcttg    540
gtttggcctt ttggattggt atacttttg ctaaacggaa atggttatat gaatggtaaa     600
ggagataaat tggtacatag ctaaaatggt atagncttaa tccn                     644

<210> SEQ ID NO 61
<211> LENGTH: 678
<212> TYPE: DNA
<213> ORGANISM: Glycine max

<400> SEQUENCE: 61
aaattcattt aacttctcta attttttaaat cgatcaaatt tggttttca atctaaaata    60 taagaaacta tattttgtga tgggtttaaa atcgacatta agtgttctta atctaccaca    120
aaaagcacat ttccaaaaaa ataaattaat tttaaaaatt ataagatcaa attgaatcaa    180
ttttaaaaat taaatatta aattgaaaaa aaaataaag gatcaaattg aacataaata     240
ataaatttga ggattaaaaa actaatttaa cctttaattt tttctcactt atattaatat    300
taaaaaatta tattgatttt cctaataact ccttatctca attaaaattt ccaaaaatta    360
attctagcat cttcaaacac tactcaccat gaaagttcat cacaaccatc tttctttctc    420
ttttctctac atcatgtttt cgcttcgcaa actttattgt gttcctagtc ttagacgtct    480
gataatcttc cacaagtatt gaactataac acttattgga cttgcaccgg taatagctaa    540
caccaaatga gacgtgcact tgactttat atcactaaga aaatttcaac acattgacca    600
agattagctc catcttgctt taacacttgg ttgactagtc acttaagtgc aacaaccact    660
ttgatatcat tgggtgga                                                  678

<210> SEQ ID NO 62
<211> LENGTH: 571
<212> TYPE: DNA
<213> ORGANISM: Glycine max
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t

<400> SEQUENCE: 62
```

```
tcttttaaga ccattcgaca ctatagaata cgaattccat aattaacaat aaagtcatct    60
tctattatat attttttctt cttaaattac atgatagtat ttcatcatta tttgacaata   120
atgatatttt tatctcataa atattatttt gttttaaaaa tattcatagc acacacgagt   180
tttttatatc aacaaagagg tatcacttca gttggtcaat ttggtctaac ttttagacaa   240
tgtcgtatag ttgaattgaa ttggaatttg gcagtatata ttttacttt tgccccctta    300 ttttcaatca aattagagta gacgcctcgt attattggca tacatggata ttggatcggc   360
acctgtgttt cagacctgag tcacatctga ctcggatcga ttttatctta catgaaaatt   420
ccaaaataat gaaagatatg gcaattggca ccatgtaact ctatggacac caatgcttca   480
ccgtagagct ctaaatttcg aggccttcta tatatagctt tgcgtgacta tgtnaaatta   540
ntcaatatcn tnttaattt tttgnggccc c                                   571
```

<210> SEQ ID NO 63
<211> LENGTH: 856
<212> TYPE: DNA
<213> ORGANISM: Glycine max
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<400> SEQUENCE: 63

```
aattagttgt cttgtttatt cattaccttt tcaattttt taatcaccat aattaaggcc    60
tttcgaatcc ctttaagtga taaaagaaac gtgcaattat gcgaacaaat aaattttcgt   120
tatgttacta tttagtcaag gaggaaaaaa aagtgataag ggaagaaaca agggatattt   180
cctgttataa caaacttaaa atggcgacta ttttgacgac attgcaaata ctcatagtac   240
gatataaatt ttgaatttaa tatacaatga ataggcatat tcattttcta ccccaaaaaa   300
gcatactcat ttatgtacat ttaattttct ctccatagag gaattaatgt acaaccatgc   360
ataagggatg agcgaaaggg acagattatt gcaatccaga agcatccaag gaaagttgga   420
taaacaaatc aattaatata tataaaaaaa aaacaaaaat gctcctagta gaagattaaa   480
ggaagagttg gctatatatg gcaaaccttt tctaactggt ttaccctctt ctcatcaccc   540
gcattgcatc accaatacgg gaacttttcc cattacaaaa ctcattggaa gccaacatat   600
cccccaaaat tccactggat ctgcattgtc catgaaattt gacatttctt cttctacaaa   660
attcccatgc tatgtcgttt tccaccatcc taggtcatag tccttcttca ttccccgaat   720
cgnttcacac ttgtatgcaa tcttccaccc cagcctcatg ggaaacaccg ntaacactat   780
cactctaata tcattcttgg cataaactca tctataaacc tctcgnccac gggctcttta   840
aattctcatc ttnttn                                                   856
```

```
<210> SEQ ID NO 64
<211> LENGTH: 639
<212> TYPE: DNA
<213> ORGANISM: Glycine max
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t

<400> SEQUENCE: 64 tccccttttgg gtcccaagta ataggccctc agagccaaaa cattggggtg tctaattttt      60
cctagaacac tgacttctga ttcaaattct ctatgacctt tagtgatctt ttccctcaat     120
ctctttactg caacttgact tccatcctcc aaaatagcct tataaacagt tccataggtg     180
ctctttccca tgatctcagc tgttgcacac aagagatcat cagctgtaaa agccattggt     240
ccatcaaaat ggactagttt ccctccagcc tccccacctg cttcaacatc accaccagca     300
actggaggga ctccttttc tgtcctcata gtggccgctc taccctcggt ggcttggccg      360
tcccggcctt agatgttgat ctctttctga tcaggcagaa aagcaggaca caacaaagta     420
taatcaggac tacgaggaga actcctgcta ctatgagaat tatgtctttg ggcttagctt     480
ctatgatggt gatggtttga cacttcagga ggtggggcaa tgactccttg tgatggagct     540
tgggaaagac atggggttga agggctggac ccacatagtt gaatatttcc acaaatgagc     600
ttgagttaaa attcttggca agcananggg ggacagaan                            639

<210> SEQ ID NO 65
<211> LENGTH: 495
<212> TYPE: DNA
<213> ORGANISM: Glycine max
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t

<400> SEQUENCE: 65
ttcccaatgc cggagcttcc ctatcgtggg ccccacctat gangaataca ccctcgaatg      60
aaatacatgt tgttgntgnt ggacgcgccc agccgagagt gccggtccac tagtatcccc     120
```

```
aacgtgcatg gcgcatgcgc ttgaaaccta gtattcatct tcctgatgga ggcagccacg      180
tgtccgacaa ggtcaatgtt gccgttttcg tgaaaaggga tgataatgaa aggcaccata      240
ttgtcttggg cgaggttgaa aatggcgtcg tgcatgctct tgtaaggtgc cacgttgatg      300
tagggaagaa ccttgactgg cccacttgag ttgttggagt agttttcgaa ggcttgcatg      360
atgtggttgg tgttggggta attcacagac aagaattttc tgcgaccggg tctatgtttt      420
atgggaagga gaatgggtgc acttttccca cgagctcnat aaggggact gcntanacnc      480 atatggggct ctctt                                                      495

<210> SEQ ID NO 66
<211> LENGTH: 480
<212> TYPE: DNA
<213> ORGANISM: Glycine max
<220> FEATURE:
<221> NAME/KEY: misc_feature
<222> LOCATION: (2)..(2)
<223> OTHER INFORMATION: n is a, c, g, or t

<400> SEQUENCE: 66
cnttcttaga atcgaattct ttggtatcag aacatatcag tcattttttaa agaataagaa      60 attaaattag acttaattttt taagagtatg gattaaaatg taaaatttgt ggggattata     120
aacataaata agtaattttt cctatatgag acatttattg aaatcttaag ataagatacg     180
tacatgcaaa ttaaattgat gcatgataat agaattaggt gaatagtcca atacctgaca     240
cctctttggt ccgaagtttt tggggcactt cttgatacct aaacccacag tgaagaagag     300
gctctggtca atttcagtgg gtacttcaac ttttctaggg cttctgaagc ttttgctgaa     360
ggaagtgact gcgtttgtgt ccgttgtaag cagggagtgg aggcattata ggtttggttt     420
tgttctttac tcctttggca cgatggtgag aatgcttatt gtggtgattc ggtgatttgt     480

<210> SEQ ID NO 67
<211> LENGTH: 669
<212> TYPE: DNA
<213> ORGANISM: Glycine max
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
```

<400> SEQUENCE: 67

```
atgcccaaaa aatttaccta aaagcaaata aaaagatga gtatttcttt taaattaaaa      60
atattttaat aaaaataaaa taaagatcca atgataatg tgataaccga agaggaatgt     120
ctttcaacca ctgcctgacc gccaccactg ccaacagcct agtatcaacc gaatccacat    180
ataccaacaa tcttcagaca aacacttcta agttggtgct gaagagacaa tatctcatgg    240
gtagatcaaa ttaagagtgc taccaataac aaaatcggga tcatttgact aacaaacagt    300
tatgtgcatt ggatgttcta ccatagtaca ttgctttatg tgaaattctt ttaattattc    360
aatattgaca tgggtcttat atatatatat atatatatat atatatatat atatatacga    420
gggattgtat tatctctgaa aaaagatttt atcataaaat cataatgatt tctcataatg    480
gatctntaca ttttaaaggt agataaataa aattgatttt aaatngggag ataaattaa     540
aanacataat taatatgact tttaacaaat tgatatataa acacttaaaa aaaagntcca    600
tgacgcacng ggggnattgg tgggacaaaa aaaattatct atcactaatt aaantatta     660
taaatatan                                                             669
```

<210> SEQ ID NO 68
<211> LENGTH: 486
<212> TYPE: DNA
<213> ORGANISM: Glycine max
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t

<400> SEQUENCE: 68

```
tggtgtatat aattaaaatg agtttaatat ttatgtatta atagtataaa atttatcata     60
catgatgaat ggtgaaattt tgaattatga ttaaataatt atataaaaaa atttacatga    120
tgaatgaata actttttttt tctcaattaa aattatgatc ctttgtcgat atgttttact    180
gtgtcgacct tttttttcgg gggagagggg accagtagga gaagtagtat ttagtaaaag    240
aagggagaga gaagttgact tatcctttaa ttagtttaga gaaaattaga cgagaaggaa    300
aaaaaatagg cgaaagtcac ttttttcttc tatctctacc aagaatgttg atgaaaaagt    360
ggggagcaga attttaaatt tttattttca tatttatcct tctccacatt tttgntttct    420
tccattttt tataaaanga tttattttag gcatagntaa cttttcaatt ttttccattt    480
ctattc                                                                486
```

<210> SEQ ID NO 69
<211> LENGTH: 779
<212> TYPE: DNA
<213> ORGANISM: Glycine max
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (669)..(670)
<223> OTHER INFORMATION: n is a, c, g, or t
<220> FEATURE:
<221> NAME/KEY: misc_feature

```
<222> LOCATION: (676)..(676)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (716)..(717)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t

<400> SEQUENCE: 69
tatttgtaaa ttgtttttta taattgaaaa gaaaataagg ttaaattatt ttcatataaa      60
aaatttaatt tgttcttata agttattttg aaaattttat taaataagt tgaaaacaat     120 ttataaataa atcataaact ataattttat aagttttctt aaatacttac acgtatgcca    180
taaaataagt tcagataaga tataaataaa ttcctccaaa cacatcttaa atctatattt    240
ttttaaaaca aactttcatc gttaaaagga tattataata ataataataa acttcaatca    300
ttaacaatta atatatgtgg ataaaagagc attcaaaatg atattttatt agcacatgac    360
aaatcacatt actctcaagc tatttttta aactaataaa aacttacata ttatatgata     420
tgatatatac tctctctata tttacacttt tttgagataa acaaggataa aaaatgatgt    480
aaatatgacc gcatataata ttatttataa tgtacggaat gccgtttttg acattttata   540
taatatatct gggggcaatt attttcttaa ccaataatta gcaaattttt atcttgcttt    600
ttctccatgg gggctaaatt aaactaaagg gncgtaccca atccagtccc actttttttt   660
aaataattnn ttccntccc acttagnaaa ggagtntttn ggcttaaatn ggcagnncca    720
ttaaccataa gcctttntgg taaggagtct taccaantaa aatggggaag gccccccc    779

<210> SEQ ID NO 70
<211> LENGTH: 677
<212> TYPE: DNA
<213> ORGANISM: Glycine max
<220> FEATURE:
<221> NAME/KEY: misc_feature
<222> LOCATION: (622)..(622)
<223> OTHER INFORMATION: n is a, c, g, or t

<400> SEQUENCE: 70
ttattggctt aacttgagtt tcaactcctt ctctggtcct ttaccagcta gcctaactca      60
ctcattttct ctcactttc tttctcttca aaataacaat ctttctggct cccttcctaa    120
ctcttggggt gggaattcca agaatggctt ctttaggctt caaaatttga tcctagatca   180
taactttttc actggtgacg ttcctgcttc tttgggtagc ttaagagagc tcaatgagat   240
ttcccttagt cataataagt ttagtggagc tataccaaat gaaataggaa ccctttctag   300
```

```
gcttaagaca cttgacattt ctaataatgc cttgaatggg aacttgcctg ctaccctctc    360
taatttatcc tcacttacac tgctgaatgc agagaacaac ctccttgaca atcaaatccc    420
tcaaagttta ggtagattgc gtaatctttc tgttctgatt ttgagtagaa accaatttag    480
tggacatatt ccttcaagca ttgcaaacat ttcctcgctt aggcagcttg atttgcactg    540
aataatttca gtggagaaat tccagctcct ttgcagtcag cgcagctaaa tctcttcaat    600
ggttcctaca atagcctctc anggtctgtc cccctctgc ttgccaagaa atttaactca    660
agctcatttg tgggaat                                                   677

<210> SEQ ID NO 71
<211> LENGTH: 571
<212> TYPE: DNA
<213> ORGANISM: Glycine max
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t

<400> SEQUENCE: 71
tgggactggc tgtgactgat ctctctggtc taatctcttc cagctgctgg agaacttgat     60
gaacttctgg tcgtgctgat ggagaaggat caacacagtg caaagcgagc ttcaacgtgt    120
ttagcaactc gtcgccaact gtggatgcat ctctcatcaa gtctgcatca aaaacctcat    180
ttgtccactc ctctttgaca actgaggcaa cccactgagg caaatctagt ccattcatag    240
acaccccagg tgatttcctc gttaggagtt ctaacaagat aacaccaaga ctgtagatat    300
```

```
cagttttagt gtttgctttc ttgagctttg agagctcagg tgcccggtat cccaatgctt    360
cagctgtagc tatcacgttg gaattagcag cagttgacat caaccgagaa agaccaaaat    420 ctgcaattt agcatttgna ttctcattaa acaacacaat gntggatgng anggtnccat      480
ggatgaaggt cttctnggna agnaagnaaa acaaagcacc gggccaaggn ttgggctaat    540
ttcaaccttg ggggcaaac naanaaatgt t                                     571
```

```
<210> SEQ ID NO 72
<211> LENGTH: 756
<212> TYPE: DNA
<213> ORGANISM: Glycine max
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(502)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
```

```
<220> FEATURE:
<221> NAME/KEY: misc_feature
<222> LOCATION: (752)..(752)
<223> OTHER INFORMATION: n is a, c, g, or t

<400> SEQUENCE: 72
attggcttaa cttgagtttc aactccttct ctggtccttt accagctagc ctaactcact      60
cattttctct cactttctt tctcttcaaa ataacaatct ttntggctcc cttnctaact     120
gtgggggggg gaatancaag ggnggcttta ggctgcaaaa tttgatccta gatcataact     180
ttttcactgg tgacgttcct gcttctttgg gtagcttaag agagctcaat gagatttccc     240
ttagtcataa taagtttagt ggagctatac caaatgaaat aggaacccctt tctaggctta     300 agacacttga catttctaat aatgccttga atgggaactt gcctgctacc ctctctaatt     360
tatcctcact tacactgctg aatgcagaga acaacctcct tgacaatcaa atccctcaaa     420
gtttaggtag attgcgtact cttccctgtt ccgattttga gtagaaacca atttagtgga     480
catattcctt caagcatngc nnacatttcc tcgcttaggc agcttgattg tcactgaata     540
atttcaggtg gagaaattnc agtctncttt gacagtcagc gcagtctaaa tcttcttcaa     600
tggttnctac aataggcctc tcagggtctg gcccccctttt gnttggccaa ggaaanttaa     660
cttaagctta tttggngggg aaanattcaa ctatgggggg acncggccct ttaaaccccca     720 gggnttttcc caggttcctt ccaagggngc anttgt                                756

<210> SEQ ID NO 73
<211> LENGTH: 557
<212> TYPE: DNA
<213> ORGANISM: Glycine max
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (345)..(346)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
```

```
<222> LOCATION: (381)..(381)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t

<400> SEQUENCE: 73
tgtgactgat ctctctggtc taatctcttc cagctgctgg agaacttgat gaacttctgg      60
tcgtgctgat ggagaaggat caacacagtg caaagcgagc ttcaacgtgt ttagcaactc     120
gtcgccaact gtggatgcat ctctcatcaa gtctgcatca aaaacctcat ttgtccactc     180
ctctttgaca actgaggcaa cccactgagg caaatctagt ccattcatag acncccagg      240 tgatttcntc gttaggagtt ntaacaagat aacaccaaga ctgtagatat cagttttagt     300
gtttgctttc ttgagctttg agagttaagg gncccggant cccanngntc nagttgnagt     360
tatancgttg gaattagcag nagttgcntc aaccgaaaaa gaccaaaatc tgaattttag     420
catttgtttt tcatcaagca acacattgnt ggatgngagg tcccatgtat gatgttctcc     480
tgggaatgaa ggcaaacaag cccgggccaa ggcttgggct attttaatcc ttggtggcca     540
aacaatgaaa ggttnat                                                    557

<210> SEQ ID NO 74
<211> LENGTH: 673
<212> TYPE: DNA
<213> ORGANISM: Glycine max
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
```

```
<222> LOCATION: (586)..(586)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (637)..(638)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (672)..(673)
<223> OTHER INFORMATION: n is a, c, g, or t

<400> SEQUENCE: 74
gggactggct gtgactgatc tctctggtct aatctcttcc agctgctgga gaacttgatg    60
aacttctggt cgtgctgatg gagaaggatc aacacagtgc aaagcgagct tcaacgtgtt   120
tagcaactcg tcgccaactg tggatgcatc tctcatcaag tctgcatcaa aaacctcatt   180
tgtccactcc tctttgacaa ctgaggcaac ccactgaggc aaatctagtc cattcataga   240
caccccaggt gatttcctcg ttaggagttc taacaagata acaccaagac tgtagatatc   300
agttttagtg tttgctttct tgagcttttg agaagctcag gtgcccggta tcccaaatgc   360
ttccagctgt agcttatcac cgttgggaat taagcagcaa gttggacatt caacccggag   420
naaaagaccc aaaaattttg caaattttta agcaatttng gnanttcttn aatcaaggcc   480
aaccaccaat tggnttggga atggtggaag ggtttcccca atggtaattg gaagggtttc   540
ttccctnggg gaaatggaaa agggcaana aaacaaaggc ccaacngggg ccccaaaggt   600
nttttggggg ccttattttt tncnaatncc ctttggnngg ggnccaaat tcnaaantgg   660
aaattggntt tnn                                                     673

<210> SEQ ID NO 75
<211> LENGTH: 602
<212> TYPE: DNA
<213> ORGANISM: Glycine max
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
```

```
<222> LOCATION: (550)..(550)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t

<400> SEQUENCE: 75
aggctagctg gtaaaggacc agagaaggat tgaaaactca agttaagcca ataaagctta    60
gtggaattag caagactata agggattgct cctgtgagca agttgttgct gaggtcaaga   120
gactgaagca aagggcagaa acctaaagaa agaggtatgg aacctgtaag cctattgttg   180
ataactgaa cccctctaag gttgggaaga agtcccaaag ttgaagggat tgaaccacca   240
atttggttat catgaagact aagcttcctg aggccttgaa gttggccaat tttggcggtg   300
attcgacccc tcaaacccTt ccaaggaagc tggatcacaa taacctgtcc ctgagcacac   360
ttgattccaa cccaacctcc ggaacaagct ccatagccac tggcattcca gctcccgcaa   420
gaacccttct ggatcagcca actcttgctt gaaagcttat cacatgtacc tctctacaga   480
taggagggtg cttcttccct ttcactggnc tacctcttcg ggaataagcc acctaatgag   540
aaagaaagan ctgggatagc taactctaca tagnctcaag gcnagagata attagggaaa   600
ng                                                                  602

<210> SEQ ID NO 76
<211> LENGTH: 748
<212> TYPE: DNA
<213> ORGANISM: Glycine max
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t

<400> SEQUENCE: 76
attggcttaa cttgagtttc aactccttct ctggtccttt accagctagc ctaactcact    60
cattttctct cacttttctt tctcttcaaa ataacaatct ttctggctcc cttcctaact   120
cttggggtgg gaattccaag aatggcttct ttaggcttca aaatttgatc ctagatcata   180
acttttttcac tggtgacgtt cctgcttctt tgggtagctt aagagagctc aatgagattt   240
ccccttagtca taataagttt aatggagctg taccaaatga aataggaacc ctttctaggc   300
ttaagacact tgcatttctc aataatgcct tgaatgggaa cttgcctgct accctctcta   360
atttatcctc acttacactg ctgaatgcag agaacaacct ccttgacaat caaatccctc   420
aaagtttagg tagattgcgt aatctttctg ttctgatttt gggtagaaac caatttagtg   480
gacatattcc ttcaagcatt gcaaacattt cctcgcttag gcagcttgat ttgcactgaa   540
```

```
taatttcagt ggagaaattc cagtctcctt tgacagtcaa gcgcaagtct aaatctcttc    600
aatgtttcct acaatagcct ctcanggtct gnccccccct tgcttgccaa gaaatttaac    660
tcaagctcat ttgtgggaaa tattcaacta tgtgggacag nccttcaacc ccatgttttn    720
ccaagcttca tacaaggagc atggccct                                       748
```

<210> SEQ ID NO 77
<211> LENGTH: 563
<212> TYPE: DNA
<213> ORGANISM: Glycine max

<400> SEQUENCE: 77

```
ctggctgtga ctgatctctc tggtctaatc tcttccagct gctggagaac ttgatgaact    60
tctggtcgtg ctgatggaga aggatcaaca cagtgcaaag cgagcttcaa cgtgtttagc    120
aactcgtcgc caactgtgga tgcatctctc atcaagtctg catcaaaaac ctcatttgtc    180
cactcctctt tgacaactga ggcaacccac tgaggcaaat ctagtccatt catagacacc    240
ccaggtgatt cctcgttag gagttctaac aagataacac caagactgta gatatcagtt    300
ttagtgtttg ctttcttgag ctttgagagc tcaggtgccc ggtatcccaa tgctccagct    360
gtagctatca cgttggaatt agcagcagtt gacatcaacc cgagaaagac caaaatctgc    420
aattttagca tttgtattct catcaagcaa cacattgctg gatgtgaggt tcccatgtat    480
gatgttctcc tgggaatgaa ggcagaacaa gccacggcca agcttggcta tttcatcctt    540
gtggccaatc aatgaatggt cat                                            563
```

<210> SEQ ID NO 78
<211> LENGTH: 623
<212> TYPE: DNA
<213> ORGANISM: Glycine max
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t

<400> SEQUENCE: 78

```
gattttgcac atctacttga gtaggcttca catgattccg tgtattactt ttattttggt    60
atatatacca tgtggagtat agtatcactt tttgtcctac aaccacattt tatgagactt    120
gcattttatg tgacatgaac ataaaaaata atgaaaaaga aaatgtcaca tatatatgat    180
acaatctttt taaaagtcaa tttgaataat ttttcatcag gaggaaaaag aagagagaaa    240
atgaattaag tttcttctaa aaattaaaat caacttataa aagaaaaaa ctttaatgaa    300 aaaaattcaa aaagaaaaag aataaaatga tcaatagcct ttaggtttaa gcacaaggtg    360
aatccaaata aagaccccaa aagatagtac agaacccaac aatggtaaaa tctagaaata    420
tacatgtaaa gactgcattt atagaccatc atgactagca aatgcttaaa ggcacataga    480
tgaattaatc tatgcaacaa aatctgnccc aagttttttt tangcaagga aaatcatatc    540
attttattaa ggataactga gaggaccaat ggtgtaatca attgaaatca tgcgaggctt    600
acatgaaatc tgtcaccaag tac                                            623
```

<210> SEQ ID NO 79
<211> LENGTH: 605
<212> TYPE: DNA
<213> ORGANISM: Glycine max

```
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (602)..(603)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t

<400> SEQUENCE: 79
ctcccgggtc ccaagtaata ggcccctcag agccaaaaca ttggggggc  taatttttcc      60 tagaacactg acttctgatt caaattctct atgaccttta gtgatctttt ccctcaatct     120
ctttactgca acttgacttc catcctccaa aatagcctta taaacagntc cataggtgct     180
cttccccatg atctcagctg gtgcacacaa gagatcatca gctgtaaaag ccattggtcc     240
atcaaaatgg actagtttcc ctccagcctc cccacctgct tcaacatcac caccagcaac     300
tggagggact cctttttctg cctcatagtg gccgctctac cctcggtggc ttggccgntc     360
ccggccttag atgntgatct ctttctgatc aggcagaaaa gcaggacaca acaaagnata     420
atcaggacta cgaggagaac tcctgctact atgagaatta tgnctttggg gcttagcttc     480
ctatgatggg gatggttnga cacttcanga gggggggcaa tgactccctg gganggagct     540
tgggaaagac atgggggtga aggnctgnac ccacataggn gaaaaattcc cacaaangag     600 cnngn                                                                605
```

```
<210> SEQ ID NO 80
<211> LENGTH: 711
<212> TYPE: DNA
<213> ORGANISM: Glycine max
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 80
ttaangncca acgactcact atagggcgaa ttgggcccga cgtcgcatgc tcccggccgc    60
catggccgcg ggattggctt aacttgagtt tcaactcctt ctctggtcct ttaccagcta   120
gcctaactca ctcatttcct ctcacttttc tttctcttcn taaaataaca atctttctgg   180
ctcccttcct aactcttggg gtgggaattc aagaatggc ttcttaggc ttcaaaattt     240 gatcctagat cataactttt tcactggtga cgttcctgct tctttgggta gcttaagaga   300
gctcaatgag atttcccta gtcataataa gtttagtgga gctataccaa atgaaatagg    360
aaccctttct aggcttaaga cacttgacat ttctaataat gccttgaatg ggaacttgcc   420
tgctaccctc tctaatttat cctcacttac actgctgaat gcagagaaca acctccttga   480
caatcaaatc cctcaaagtt taggtagatt gcgtaatctt tctgttctga ttttgagtag   540
aaaccaattt agtggacata ttccttcaag cattgcaaac atttcctcgc ttaggcagct   600
tgatttgtca ctgaataatt tcagtggaga aattccagtc tcctttgaca gtcagcgcag   660
tctaaatctc ttcaatgttt cctacaatag cctctcaggg tctgtccccc n            711

<210> SEQ ID NO 81
<211> LENGTH: 716
<212> TYPE: DNA
<213> ORGANISM: Glycine max
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t

<400> SEQUENCE: 81
ttnntgaaaa ccctttgcta tttaggtgac actatagaat actcaagcta tgcatccaac    60
gcgttgggag ctctcccata tggtcgacct gcaggcggcc gcactagtga ttaatacgac   120
tcactatagg gctcgagcgg ccgcccgggc aggtgggact ggctgtgact gatctctctg   180
gtctaatctc ttccagctgc tggagaactt gatgaacttc tggtcgtgct gatggagaag   240
gatcaacaca gtgcaaagcg agcttcaacg tgtttagcaa ctcgtcgcca actgtggatg   300
catctctcat caagtctgca tcaaaaacct catttgtcca ctcctctttg acaactgagg   360
caacccactg aggcaaatct agtccattca tagacacccc aggtgatttc ctcgttagga   420
gttctaacaa gataacacca agactgtaga tatcagtttt agtgtttgct ttcttgagct   480
```

```
ttgagagctc aggtgcccgg tatcccaatg ctccagctgt agctatcacg ttggaattag    540
cagcagttga catcaaccga gaaagaccaa aatctgcaat tttagcattt gtattctcat    600
caagcaacac attgctggat gtgaggttcc catgtatgat gttctcctgg gaatgaaggc    660
agaacaagcc acgggccaag tcttgggcta ttttcatcct tggtgggcca atcaan        716
```

<210> SEQ ID NO 82
<211> LENGTH: 713
<212> TYPE: DNA
<213> ORGANISM: Glycine max
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t

<400> SEQUENCE: 82

```
ttcctaangc ctacgactcc tatagggcga attgggcccg acgtcgcatg ctccccggccg    60 ccatggccgc gggattatac gactcactat agggctcgag cggccactat gaggacagaa   120
aaaggagtcc ctccagttgc tggtggtgat gttgaagcag gtggggaggc tggagggaaa   180
ctagtccatt ttgatggacc aatggctttt acagctgatg atctcttgtg tgcaacagct   240
gagatcatgg gaaagagcac ctatggaact gtttataagg ctattttgga ggatggaagt   300
caagttgcag taaagagatt gagggaaaag atcactaaag gtcatagaga atttgaatca   360
gaagtcagtg ttctaggaaa aattagacac cccaatgttt tggctctgag ggcctattac   420
ttgggaccca aagggaaaa gcttctggtt tttgattaca tgtctaaagg aagtcttgct    480
tctttcctac atggtaagtt tcgtgtgctg ttctttcatt aagtgttgtg tgtgctgttc    540
tttaattata atttggagtt ttaccttagt aatctgtata attctaatcg gagaacagta   600
caaacaaaaa cacctaagga acaacacctt anctttaata taccatatca ataagtgaat   660
tattttctta ttcatcttga tgcaggtggt ggaactgaaa catttatttg atn           713
```

<210> SEQ ID NO 83
<211> LENGTH: 712
<212> TYPE: DNA
<213> ORGANISM: Glycine max
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature

```
<222> LOCATION: (704)..(704)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t

<400> SEQUENCE: 83
nnnctaaggc ccnttactca ctatngggcg aattgggccc gacgtcgcat gctcccggcc      60
gccatggccc gcgggattgg cttaacttga gtttcaactc cttctctggt cctttaccag    120
ctagcctaac tcactcattt tctctcactt ttctttctct ttaaaataac aatctttctg    180
gctcccttcc taactcttgg ggtgggaatt ccaagaatgg cttctttagg cttcaaaatt    240
tgatcctaga tcataacttt ttcactggtg acgttcctgc ttctttgggt agcttaagag    300
agctcaatga gatttccctt agtcataata agtttagtgg agctatacca aatgaaatag    360
gaacccttc taggcttaag acacttgaca tttctaataa tgccttgaat gggaacttgc    420
ctgctaccct ctctaattta tcctcactta cactgctgaa tgcagagaac aacctccttg    480
acaatcaaat ccctcaaagt ttaggtagat tgcgtaatct ttctgttctg attttgagta    540
gaaaccaatt tagtggacat attccttcaa gcattgcaaa catttcctcg cttaggcagc    600
ttgatttgca ctgaataatt tcagtggaga aattccagtc tcctttgcag tcagcgcagt    660
ctaaatctct tcaatggttn ctacaatagn ctctcagggt ctgncccccc tn            712

<210> SEQ ID NO 84
<211> LENGTH: 681
<212> TYPE: DNA
<213> ORGANISM: Glycine max
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t

<400> SEQUENCE: 84
ggnttcttta gggcttcaaa atttgatcct agatcataac ttttttcact ggtgacgttc     60
ctgcttcttt gggtagctta agagagctca atgagatttc ccttagtcat aataagttta    120
gtggagctat accaaatgaa ataggaaccc tttctaggct taagacactt gacatttcta    180
ataatgcctt gaatgggaac ttgcctgcta ccctctctaa tttatcctca cttacactgc    240
tgaatgcaga gaacaacctc cttgacaatc aaatccctca aagtttaggt agattgcgta    300
atctttctgt tctgattttg agtagaaacc aatttagtgg acatattcct tcaagcattg    360
caaacatttc ctcgcttagg cagcttgatt tgcactgaat aatttcagtg gagaaattcc    420
agtctccttt gcagtcaag cgcagctaaa tctcttcaat ggttcctaca atagcctctc    480
agggtctgcc cccctctgct tggcaagaaa tttaactcaa gctcatttgt gggaaatatt    540
caactatgtg gggtacagcc ttcaaccca tggctttcca agctncatca caaggggca    600
``` ttggcccct cctgagnggc aaacatcacc atcataggaa gctaacccca aagacataat    660
tctcatagta nccaggaggt n                                             681

<210> SEQ ID NO 85
<211> LENGTH: 639
<212> TYPE: DNA
<213> ORGANISM: Glycine max
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t

<400> SEQUENCE: 85
tcccctttgg gtcccaagta ataggccctc agagccaaaa cattggggtg tctaattttt     60
cctagaacac tgacttctga ttcaaattct ctatgaccct tagtgatctt ttccctcaat    120
ctctttactg caacttgact tccatcctcc aaaatagcct tataaacagt tccataggtg    180
ctctttccca tgatctcagc tgttgcacac aagagatcat cagctgtaaa agccattggt    240
ccatcaaaat ggactagttt ccctccagcc tccccacctg cttcaacatc accaccagca    300
actggaggga ctccttttc tgtcctcata gtggccgctc taccctcggt ggcttggccg    360
tcccggcctt agatgttgat ctctttctga tcaggcagaa aagcaggaca caacaaagta    420
taatcaggac tacgaggaga actcctgcta ctatgagaat tatgtctttg ggcttagctt    480
ctatgatggt gatggtttga cacttcagga ggtggggcaa tgactccttg tgatggagct    540
tgggaaagac atggggttga agggctggac ccacatagtt gaatatttcc acaaatgagc    600
ttgagttaaa attcttggca agcanangg ggacagaan                            639

<210> SEQ ID NO 86
<211> LENGTH: 661
<212> TYPE: DNA
<213> ORGANISM: Glycine max
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t

```
<220> FEATURE:
<221> NAME/KEY: misc_feature
<222> LOCATION: (646)..(647)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t

<400> SEQUENCE: 86
gaaggatggt tattttgaag agaaagaaaa gtgagagaaa atgagtgagt taggctagct      60
ggtaaaggac cagagaagga gttgaaactc aagttaagcc aataaagctt agtggaatta     120
gcaagactat aagggattgc tcctgtgagc aagttgttgc tgaggtcaag agactgaagc     180
aaagggcaga aacctaaaga aagaggtatg gaacctgtaa gcctattgtt gaataactga     240
acccctctaa ggttgggaag aagtcccaaa gttgaaggga ttgaaccacc aatttggtta     300
tcatgaagac taagcttctg aggccttgaa gttggccaat tttgtcggtg attcgacccc     360 tcaaacccctt ccaaggaagc tggatcacaa taacctgtcc ctgagcacac ttgattccaa    420
cccacctccg gaacaagctc catagccact gtcattccag cttccgcaag aacccttctg     480
gatcagccaa ctcttgcttg aaaagcttat cacatgtacc ttttacagat aggaggntgc     540
ttcttccttt cactggtcta cctcttcgga ataagccaac ctaatgagaa agaaagatct     600
gngatagctn acttacatac tnagncagag ataattantg naagcnnaag ttaaacntnt     660
t                                                                    661

<210> SEQ ID NO 87
<211> LENGTH: 626
<212> TYPE: DNA
<213> ORGANISM: Glycine max
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t

<400> SEQUENCE: 87
aattcgtggg ctacaaagga tgaacgtaaa ctatatgcac ctccagctgg ttcaggcttc      60
atatctggct ttacttctat ctcacgcaga tcttctgttg atagtactca aaatctgtct     120 attcctttg gtccaagctc atacctttct gcacaggctc gagtagttga tgagtattct      180
atgtcccaga ttatcttaca aaatgtgctt gatggagggg tcactggtat gttaatagtt     240
gtcactggtg caagccatgt tacatatgga tctagaggaa ctggagtgcc agcaagaatt     300
tcaggaaaaa tacaaaagaa aaaccatgca gttatattac ttgaccctga agacaattc      360 attcgcagag aaggagaagt tcctgttgct gattttttgt ggtattctgc tgcgagaccc     420
tgtagtagaa attgctttga ccgtgctgag attgctcggg ttatgaatgc tgctgggcgg     480
aggcgagatg ccctcccaca ggtaaaccaa caattacagt tactaatttg tttgactgtt     540
aatcttcttg ccccatagac cctncttcca attttttagcc ctttatgtcc tctcattcct    600
agngggataa gggtttgggg gnggtg                                         626
```

<210> SEQ ID NO 88
<211> LENGTH: 627
<212> TYPE: DNA
<213> ORGANISM: Glycine max

<400> SEQUENCE: 88

```
tgaaaaactg aaggaccaaa ttaaatctaa aaaataaata aattaaaaga ctaaaaaata      60
aatctatcca aaattaaaag gtttattctt ggaagtaatg aaatgtattt tgactctttg     120
aagaatgcat tactataatg aaagagtagg tggagagagg ggataataaa atcccactaa     180
ataacatcca tgactatcac tataaaaaaa aatattatta ttaagataag aagaattatc     240
taacttgaat aagagactac taccaaagtg agaaaaaggt cttataacat agagtttttc     300
aagtttacct ataaaacttg taataagatt tgttttccaa ccatctaatt ttttattagt     360
gtggactgca taaaaaaaat atagtaacaa gaaactacta aattagactt tttgaactat     420
tcattgtatg gctgccatga aacctacctg cctggagggg tgggtcccac gtaagactgt     480
aagagggagg agggaagcac tagtcacaca ccggcgcacg ttagcgaggc aatgttccta     540
gattgaaacg gagaaggtga ttagagggc ggaaatctca aagcagacac aggcaactaa     600
tttatcgcct ctttcctcat tcgctta                                         627
```

<210> SEQ ID NO 89
<211> LENGTH: 782
<212> TYPE: DNA
<213> ORGANISM: Glycine max
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t

<400> SEQUENCE: 89

```
cacataatta acaataaagt catcttctat tatatatttt ttcttcttaa attacatgat      60
agtatttcat cattatttga caataatgat attttttatct cataaatatt attttgtttt    120
aaaaatattc atagcacaca cgagtttttt atatcaacaa agaggtatca cttcagttgg     180
tcaatttggt ctaactttta gacaatgtcg tatagttgaa ttgaattgga atttggcagt     240
atatattta ctttttgccc ccttattttc aatcaaatta gagtagacgc ctcgtattat     300
tggcatacat ggatattgga tcggcacctg tgtttcagac ctgagtcaca tctgactcgg    360
atcgattta tcttacatga aaattccaaa ataatgaaag atatggtaat tggcaccatg     420
taactctatg gacaccaatg cttcacgtag agctctaaat ttgaggcctt ctatatatag    480
tttgcgtgac tatgtaaatt atcaatatca tttaattttt ttgcgaccac gaaatatacg    540
aatttattat tgaacacaaa aagtgagtg tatatttaa gtctaggatt ttatgagagg     600
caaaaataag aataacctct tgatatattt tcttggatac actttcttta ttatatattt    660
tttaataatg gattataatt tattggaaac aatcaaatta tangggaaaa ttcattggaa    720
taaaagaang aaatttaaaa aaaaatataa ttttaatat attaagtaa taaaaatcct     780
tt                                                                    782
```

<210> SEQ ID NO 90
<211> LENGTH: 160
<212> TYPE: DNA
<213> ORGANISM: Glycine max

<400> SEQUENCE: 90
tggttgagat gtgtataaga gacagttgcc ccacctcctg aagtgtcaaa acatcaccat       60
cataggaagc taagcaccaa agacataatt ctcatagtag caggagttct cctcgtagtc      120
ctgattatac tttgttgtgt cctgcttttc tgcctgatca                            160

<210> SEQ ID NO 91
<211> LENGTH: 779
<212> TYPE: DNA
<213> ORGANISM: Glycine max
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (524)..(525)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature

```
<222> LOCATION: (771)..(771)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t

<400> SEQUENCE: 91
tgctcccggc gcatggccgn gggattggct taacttgagt ttcaactcct tctctggtcc      60
tttaccagct agcctaactc actcattttc tctcactttt ctttctcttc aaaataacaa     120
tctttntggc tcccttncta actgtggggg ggggaatanc aagggnggct ttaggctgca     180
aaatttgatc ctagatcata acttttttcac tggtgacgtt cctgcttctt tgggtagctt     240
aagagagctc aatgagattt cccttagtca taataagttt agtggagcta taccaaatga     300
aataggaacc ctttctaggc ttaagacact tgacatttct aataatgcct tgaatgggaa     360
cttgcctgct accctctcta atttatcctc acttacactg ctgaatgcag agaacaacct     420
ccttgacaat caaatccctc aaagtttagg tagattgcgt actctttcct gttccgattt     480
tgagtagaaa ccaatttagt ggacatattc cttcaagcat ngcnnacatt tcctcgctta     540
ggcagcttga ttgtcactga ataatttcag gtggagaaat tncagtctnc tttgacagtc     600
agcgcagtct aaatcttctt caatggttnc tacaataggc ctctcagggt ctggccccc     660
tttgnttggc caaggaaant taacttaagc ttatttggng gggaaanatt caactatggg     720
gggacncggc cctttaaacc ccagggnttt tcccaggttc cttccaaggg ngcanttgt      779

<210> SEQ ID NO 92
<211> LENGTH: 743
<212> TYPE: DNA
<213> ORGANISM: Glycine max
<220> FEATURE:
<221> NAME/KEY: misc_feature
<222> LOCATION: (623)..(623)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t

<400> SEQUENCE: 92
ttggcttaac ttgagtttca actccttctc tggtccttta ccagctagcc taactcactc      60
attttctctc acttttcttt ctcttcaaaa taacaatctt tctggctccc ttcctaactc     120
ttggggtggg aattccaaga atggcttctt taggcttcaa aatttgatcc tagatcataa     180
ctttttcact ggtgacgttc ctgcttcttt gggtagctta agagagctca atgagatttc     240
ccttagtcat aataagttta gtggagctat accaaatgaa ataggaaccc tttctaggct     300
taagacactt gacatttcta ataatgcctt gaatgggaac ttgcctgcta ccctctctaa     360
tttatcctca cttacactgc tgaatgcaga gaacaacctc cttgacaatc aaatccctca     420
aagtttaggt agattgcgta tctttctgt tctgattttg agtagaaacc aatttagtgg     480
acatattcct tcaagcattg caaacatttc ctcgcttagg cagcttgatt tgtcactgaa     540
taatttcagt ggagaaattc cagtctcctt tgacagtcag cgcagtctaa atctcttcaa     600
tgtttcctac aatagcctct cangttctgn ccccctctg cttgccaaga aattaactca     660
```

```
agctcatttg tgggaaatat tcaactatgt gggacaggcc ttcaacccca ngctttncca    720
agcttcatca caagggcat tgg                                              743

<210> SEQ ID NO 93
<211> LENGTH: 742
<212> TYPE: DNA
<213> ORGANISM: Glycine max
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t

<400> SEQUENCE: 93
ttaacttgag tttcaactcc ttctctggtc ctttaccagc tagcctaact cactcatttt    60 ctctcactt tctttctctt caaaataaca atctttctgg ctcccttcct aactcttggg    120
gtgggaattc caagaatggc ttcttaggc ttcaaaattt gatcctagat cataactttt    180
tcactggtga cgttcctgct tctttgggta gcttaagaga gctcaatgag atttccctta    240
gtcataataa gtttaatgga gctgtaccaa atgaaatagg aacccttct aggcttaaga    300 cacttgacat ttctaataat gccttgaatg ggaacttgcc tgctaccctc tctaatttat    360
cctcacttac actgctgaat gcagagaaca acctccttga caatcaaatc cctcaaagtt    420
taggtagatt gcgtaatctt tctgttctga tttgggtag aaaccaattt agtggacata     480
ttccttcaag cattgcaaac atttcctcgc ttaggcagct tgatttgcac tgaataattt    540
cagtggagaa attccagtct cctttgacag tcaagcgcaa gtctaaatct ttcaatgtt    600 tcctacaata gcctctcang gtctgncccc cctctgcttg ccaagaaatt taactcaagc    660
tcatttgtgg gaaatattca actatgtggg acagnccttc aaccccatgt tttnccaagc    720
ttcatacaag gagcatggcc ct                                              742

<210> SEQ ID NO 94
<211> LENGTH: 741
<212> TYPE: DNA
<213> ORGANISM: Glycine max
<220> FEATURE:
<221> NAME/KEY: misc_feature
<222> LOCATION: (619)..(619)
<223> OTHER INFORMATION: n is a, c, g, or t

<400> SEQUENCE: 94
cttaacttga gtttcaactc cttctctggt cctttaccag ctagcctaac tcactcattt    60
tctctcactt ttctttctct tcaaaataac aatctttctg gctcccttcc taactcttgg    120
ggtgggaatt ccaagaatgg cttcttagg cttcaaaatt tgatcctaga tcataacttt    180
ttcactggtg acgttcctgc ttctttgggt agcttaagag agctcaatga gatttccctt    240
agtcataata gtttagtgg agctataccaa atgaaatag gaacccttttc taggcttaag    300 acacttgaca tttctaataa tgccttgaat gggaacttgc ctgctaccct ctctaattta    360
tcctcactta cactgctgaa tgcagagaac aacctccttg acaatcaaat ccctcaaagt    420
```

| | |
|---|---|
| ttaggtagat tgcgtaatct ttctgttctg attttgagta gaaaccaatt tagtggacat | 480 |
| attccttcaa gcattgcaaa catttcctcg cttaggcagc ttgatttgca ctgaataatt | 540 |
| tcagtggaga aattccagtc tcctttgaca gtcaagcgca gtctaaatct cttcaatgtt | 600 |
| tcctacaata gcctctcang ttctgccccc ctctgcttgc caagaaattt aactcaagct | 660 |
| catttgtggg aaatattcaa ctatgtggga caggccttca accccatgtt tttccaagct | 720 |
| ccatcacaag gggcattgcc t | 741 |

<210> SEQ ID NO 95
<211> LENGTH: 743
<212> TYPE: DNA
<213> ORGANISM: Glycine max
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t

<400> SEQUENCE: 95

| | |
|---|---|
| cttaacttga gtttcaactc cttctctggt cctttaccag ctagcctaac tcactcattt | 60 |
| tctctcactt ttctttctct tcaaaataac aatctttctg gctcccttcc taactcttgg | 120 |
| ggtgggaatt ccaagaatgg cttctttagg cttcaaaatt tgatcctaga tcataacttt | 180 |
| ttcactggtg acgttcctgc ttcttggggt agcttaagag agctcaatga gatttccctt | 240 |
| agtcataata agtttagtgg agctataccaa aatgaaatag gaacccttc taggcttaag | 300 |
| acacttgaca tttctaataa tgccttgaat gggaacttgc ctgctaccct ctctaattta | 360 |
| tcctcactta cactgctgaa tgcagagaac aacctccttg acaatcaaat ccctcaaagt | 420 |
| ttaggtagat tgcgtaatct ttctgttctg attttgagta gaaaccaatt tagtggacat | 480 |
| attccttcaa gcattgcaaa catttcctcg cttaggcagc ttgatttgca ctgaataatt | 540 |
| tcaaggggag aaattncagt ctcctttgac agtcaagcgc aagtctaaat ctcttcaatg | 600 |
| gttcctacaa taagcctctc anggtctgnc ccccctctgc ttgncaagaa aattaactca | 660 |
| agctcatttg ggggaaatat tcaactatgn gggacagncc ttcaacccat gttttccaag | 720 |
| ctccatacan gagcatggcc cnt | 743 |

```
<210> SEQ ID NO 96
<211> LENGTH: 742
<212> TYPE: DNA
<213> ORGANISM: Glycine max
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t

<400> SEQUENCE: 96
cttaacttga gtttcaactc cttctctggt cctttaccag ctagcctaac tcactcattt      60
tctctcactt ttctttctct tcaaaataac aatctttctg gctcccttcc taactcttgg     120
ggtgggaatt ccaagaatgg cttctttagg cttcaaaatt tgatcctaga tcataacttt     180
ttcactggtg acgttcctgc ttctttgggt agcttaagag agctcaatga gatttcccctt    240 agtcataata agtttagtgg agctatacca aatgaaatag gaaccctttc taggcttaag     300
acacttgaca tttctaataa tgccttgaat gggaacttgc ctgctaccct ctctaattta     360
tcctcactta cactgctgaa tgcagagaac aacctccttg acaatcaaat ccctcaaagt     420
ttaggtagat tgcgtaatct ttctgttctg attttgagta gaaaccaatt tagtggacat     480
attccttcaa gcattgcaaa catttcctcg cttaggcagc ttgatttgtc actgaataat     540
ttcaggggga gaaattccag tctcctttga cagtcagcgc aagtctaaat ctcttcaatg     600
gttcctacaa tagcctctca nggtctgncc ccctctgct tgncaagaaa ttaactcaag      660
ctcatttgtg ggaaatattc aactatgngg gacaggcctt caacccatgt ttttccaagc    720
ttcatacaag gagtaatggc ct                                              742

<210> SEQ ID NO 97
<211> LENGTH: 716
<212> TYPE: DNA
<213> ORGANISM: Glycine max
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
```

```
<222> LOCATION: (529)..(529)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (572)..(573)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(618)
<223> OTHER INFORMATION: n is a, c, g, or t
<220> FEATURE:
<221> NAME/KEY: misc_feature
<222> LOCATION: (623)..(625)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
```

```
<222> LOCATION: (644)..(644)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (652)..(654)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (693)..(694)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(701)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (707)..(708)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t

<400> SEQUENCE: 97
```

-continued

```
ggacagaaaa aggagtccct ccagttgctg gtggtgatgt tgaagcaggt ggggaggctg      60
gagggaaact agtccatttt gatggaccaa tggcttttac agctgatgat ctcttgtgtg     120
caacagctga gatcatggga aagagcacct atggaactgt ttataaggct attttggagg     180
atggaagtca agttgcagta aagagattga gggaaaagat cactaaaggt catagagaat     240
ttgaatcaga agtcagtgtt ctaggaaaaa ttagacaccc caatgttttg gctctgaggg     300
cctattactt gggacccaaa ggggaaaagc ttctggtttt tgattacatg tctaaaggaa     360
gtcttgcttc tttcctacat ggtaagtttc gtgtgctgnt ctttcattaa agtgntgggn     420
gggctggtct ttaattataa tttggagttt taccttanta atctgtataa ttctaatcgg     480
agacaagtca acaaaaaacc ctaaggaaca acnccttanc tttaatatnc catatcaata     540
angngaatta ttttnttggt tcatttgatg cnnggggng gnacntnaaa cnttnatttg      600
ntgggccacn anggnnnnaa aannncacaa ananttggnc cngnggnttn gnnntgcctt     660
tantnccang anaaacatna tacanggnan ctnncntcnn naangtnntn gttngn         716
```

```
<210> SEQ ID NO 98
<211> LENGTH: 616
<212> TYPE: DNA
<213> ORGANISM: Glycine max
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t

<400> SEQUENCE: 98
```

```
ggacagaaaa aggagtccct ccagttgctg gtggtgatgt tgaagcaggt ggggaggctg      60
gagggaaact agtccatttt gatggaccaa tggcttttac agctgatgat ctcttgtgtg     120
caacagctga gatcatggga aagagcacct atggaactgt ttataaggct attttggagg     180
atggaagtca agttgcagta aagagattga gggaaaagat cactaaaggt catagagaat     240
ttgaatcaga agtcagtgtt ctaggaaaaa ttagacaccc caatgttttg gctctgaggg     300
cctattactt gggacccaaa ggggaaaagc ttctggtttt tgattacatg tctaaaggaa     360
gtcttgcttc tttcctacat ggtaagtttc gtgtgctgtt ctttcattaa gtgttgtgtg     420
tgctgttctt taattataat ttggagnttt accttagtaa tctgtataat tctaatcgga     480
gaacagtcaa acaaaacacc taaggaacaa caccttagct ttaatatcca tatcaataag     540
tgaatatttt cttggtcatc ttgatgcagg nggnggaact tgaacaatca ttgattggnc     600
caccanggat gaaaat                                                     616
```

```
<210> SEQ ID NO 99
<211> LENGTH: 532
<212> TYPE: DNA
<213> ORGANISM: Glycine max
```

```
<400> SEQUENCE: 99
actggctgtg actgatctct ctggtctaat ctcttccagc tgctggagaa cttgatgaac    60
ttctggtcgt gctgatggag aaggatcaac acagtgcaaa gcgagcttca acgtgtttag   120
caactcgtcg ccaactgtgg atgcatctct catcaagtct gcatcaaaaa cctcatttgt   180
ccactcctct ttgacaactg aggcaaccca ctgaggcaaa tctagtccat tcatagacac   240
cccaggtgat ttcctcgtta ggagttctaa caagataaca ccaagactgt agatatcagt   300
tttagtgttt gctttcttga cttttgagag ctcaggtgcc cggtatccca atgctccagc   360
tgtagctatc acgttggaat tagcagcagt tgacatcaac cgagaaagac caaaatctgc   420
aattttagca tttgtattct catcaagcaa cacattgctg gatgtgaggt tcccatgtat   480
gatgttctcc tgggaatgaa ggcggaacaa gccacgggcc aagtcttgtg ct           532

<210> SEQ ID NO 100
<211> LENGTH: 568
<212> TYPE: DNA
<213> ORGANISM: Glycine max
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t

<400> SEQUENCE: 100
tatgaggaca gaaanttnag tccctccagt tgctggtggt gatgttgaag caggtgggga    60
ggctggaggg aaactagtcc attttgatgg accaatggct tttacagctg atgatctctt   120
gtgtgcaaca gctgagatca tgggaaagag cacctatgga actgtttata aggctatttt   180
ggaggatgga agtcaagttg cagtaaagag attgagggaa aagatcacta aaggtcatag   240
agaatttgaa tcagaagtca gtgttctagg aaaaattaga caccccaatg ttttggctct   300
gagggcctat tacttgggac ccaaagggga aaagcttctg ttttttgatt acatgtctaa   360
aggaagtctt gcttctttcc tacatggtaa gtttcgtgtg ctgttctttc attaagtgtt   420
gtgtgtgctg ttctttaatt ataatttgga gttttacctt agtaatctgt ataattctaa   480
tcggagaaca gtcaaacaaa aaccctaagg aacacacctt actttaatat accatatcaa   540
taagngaatn atttcttggt catcttga                                      568

<210> SEQ ID NO 101
<211> LENGTH: 678
<212> TYPE: DNA
<213> ORGANISM: Glycine max
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
```

```
<222> LOCATION: (628)..(628)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (677)..(678)
<223> OTHER INFORMATION: n is a, c, g, or t

<400> SEQUENCE: 101
ggtgggactg gctgtgactg atctctctgg tctaatctct tccagctgct ggagaacttg      60
atgaacttct ggtcgtgctg atggagaagg atcaacacag tgcaaagcga gcttcaacgt     120
gtttagcaac tcgtcgccaa ctgtggatgc atctctcatc aagtctgcat caaaaacctc     180
atttgtccac tcctctttga caactgaggc aacccactga ggcaaatcta gtccattcat     240
agacacccca ggtgatttcc tcgttaggag ttctaacaag ataacaccaa gactgtagat     300
atcagtttta gtgtttgctt tcttgagctt tgagagctca ggtgcccggt atcccaatgc     360
tccagctgta gctatcacgt tggaattagc agcagttgac atcaaccgag aaagaccaaa     420
atctgcaatt ttagcatttg tattctcatc aagcaacaca ttgctggatg tgaggttccc     480
atgtatgatg ttctcctggg aatgaaggca gaacaagcca cgggccaagt cttgngctat     540
tttcatcctt ggtggccaat caatgaatgg ttcagttnca ccacctgcat caagatgaac     600
aagaaaataa ttcacttatt gatatggnat attaaaagct aaggggtggt ccctagggggg    660 tttggttgga ccggncnn                                                    678

<210> SEQ ID NO 102
<211> LENGTH: 673
<212> TYPE: DNA
<213> ORGANISM: Glycine max
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t

<400> SEQUENCE: 102
ggtgggactg gctgtgactg atctctctgg tctaatctct tccagctgct ggagaacttg      60
atgaacttct ggtcgtgctg atggagaagg atcaacacag tgcaaagcga gcttcaacgt     120
gtttagcaac tcgtcgccaa ctgtggatgc atctctcatc aagtctgcat caaaaacctc     180
atttgtccac tcctctttga caactgaggc aacccactga ggcaaatcta gtccattcat     240
agacacccca ggtgatttcc tcgttaggag ttctaacaag ataacaccaa gactgtagat     300
atcagtttta gtgtttgctt tcttgagctt tgagagctca ggtgcccggt atcccaatgc     360
tccagctgta gctatcacgt tggaattagc agcagttgac atcaaccgag aaagaccaaa     420
atctgcaatt ttagcatttg tattctcatc aagcaacaca ttgctggatg tgagggtccc     480
```

-continued

```
atgtatgatg ttctcctggg aatgaaggca gaacaagcca cggccaagtc ttgngctatt      540
ttcatccttg ttggccaatc aatgaatggt tcaagttccc cacctgcatc aagatgaaca      600
agaaaataat tcacttaatg gatatggnat attaaagcta aggggtggtc cntagggggtt     660 ttgggttgnc cng                                                         673
```

<210> SEQ ID NO 103
<211> LENGTH: 665
<212> TYPE: DNA
<213> ORGANISM: Glycine max
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t

<400> SEQUENCE: 103

```
ggtgggactg gctgtgactg atctctctgg tctaatctct tccagctgct ggagaacttg       60
atgaacttct ggtcgtgctg atggagaagg atcaacacag tgcaaagcga gcttcaacgt      120
gtttagcaac tcgtcgccaa ctgtggatgc atctctcatc aagtctgcat caaaaacctc      180
atttgtccac tcctctttga caactgaggc aacccactga ggcaaatcta gtccattcat      240
agacacccca ggtgatttcc tcgttaggag ttctaacaag ataacaccaa gactgtagat      300
atcagtttta gtgtttgctt tcttgagctt tgagagctca ggtgcccggt atcccaatgc      360
```

-continued

```
tccagctgta gctatcacgt tggaattagc agcagttgac atcaaccgag aaagaccaaa    420
atctgcaatt ttagcatttg tattctcatc aagcaacaca ttgctggatg tgagggtccc    480
atgtatgatg tctnctggga atgaaggcan aacaagccac ggccaagtct tgggctattt    540
tcatccttgt ggncaatcaa tgaatggtta anttcccccc ctgcttcaag atgaacaaga    600
aaataattca cttattggtt gggntatnaa actaaggggn gnccctaggg gnttngntgn    660 ccnct                                                                665
```

<210> SEQ ID NO 104
<211> LENGTH: 671
<212> TYPE: DNA
<213> ORGANISM: Glycine max
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<400> SEQUENCE: 104

```
ggtgggactg gctgtgactg atctctctgg tctaatctct tccagctgct ggagaacttg     60
atgaacttct ggtcgtgctg atggagaagg atcaacacag tgcaaagcga gcttcaacgt    120
gtttagcaac tcgtcgccaa ctgtggatgc atctctcatc aagtctgcat caaaaacctc    180
atttgtccac tcctctttga caactgaggc aacccactga ggcaaatcta gtccattcat    240
agacacccca ggtgatttcc tcgttaggag ttctaacaag ataacaccaa gactgtagat    300
atcagtttta gtgtttgctt tcttgagctt tgagagctca ggtgcccggt atcccaatgc    360
tccagctgta gctatcacgt tggaattagc agcagttgac atcaaccgag aaagaccaaa    420
atctgcaatt ttagcatttg tattctcatc aagcaacaca ttgctggatg tgaggttccc    480
atgtatgatg ttctcctggg aatgaaggca gaacaagcca cggccaagtc ttgngctatt    540
ttcatccttg gtggccaatc aatgaatgtt tcagttccac cacctgcatc aagatgaaca    600
agaaaataat tcacttattg atatggnata ttaaagctaa ggggtggtcc ntaggggtt     660 tngntggncc c                                                         671
```

<210> SEQ ID NO 105
<211> LENGTH: 670
<212> TYPE: DNA
<213> ORGANISM: Glycine max
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature

```
<222> LOCATION: (577)..(577)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (622)..(624)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (660)..(662)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t

<400> SEQUENCE: 105
ggtgggactg gctgtgactg atctctctgg tctaatctct tccagctgct ggagaacttg     60
atgaacttct ggtcgtgctg atggagaagg atcaacacag tgcaaagcga gcttcaacgt    120
gtttagcaac tcgtcgccaa ctgtggatgc atctctcatc aagtctgcat caaaaacctc    180
atttgtccac tcctctttga caactgaggc aacccactga ggcaaatcta gtccattcat    240
agacacccca ggtgatttcc tcgttaggag ttctaacaag ataacaccaa gactgtagat    300
atcagtttta gtgtttgctt tcttgagctt tgagagctca ggtgccccggt atcccaatgc    360 tccagctgta gctatcacgt tggaattagc agcagttgac atcaaccgag aaagaccaaa    420
atctgcaatt ttagcatttg tantctcatc aagcaacaca ttgctggatg tgagggtccc    480
atgtatgatg tcctcctggg aatgaaggca gaacaagcca cgggccaagt cttgggctat    540
tttcatcctt ggtgggccaa tcaatgaatg gttcaanttc ancacctgcn tcaagangaa    600
```

```
caagaaaata attncntatg gnnnggatat naaactaagg ggnggnccta ggggtntngn     660 nngnccggcn                                                           670

<210> SEQ ID NO 106
<211> LENGTH: 662
<212> TYPE: DNA
<213> ORGANISM: Glycine max
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t

<400> SEQUENCE: 106
ggtgggactg gctgtgactg atctctctgg tctaatctct tccagctgct ggagaacttg     60
atgaacttct ggtcgtgctg atggagaagg atcaacacag tgcaaagcga gcttcaacgt    120
gtttagcaac tcgtcgccaa ctgtggatgc atctctcatc aagtctgcat caaaaacctc    180
atttgtccac tcctctttga caactgaggc aacccactga ggcaaatcta gtccattcat    240
agacacccca ggtgatttcc tcgttaggag ttctaacaag ataacaccaa gactgtagat    300
atcagtttta gtgtttgctt tcttgagctt tgagagctca ggtgcccggt atcccaatgc    360
tccagctgta gctatcacgt tggaattagc agcagttgac atcaaccgag aaagaccaaa    420
atctgcaatt ttagcatttg tattctcatc aagcaacaca ttgctggatg tgaggttcca    480
tgtatgatgt tctnctggga atgaaggcag aacaagccca gggccaagtc ttgngctatt    540
tcatccttgt gggcaatcaa tgaatgttta anttccncac ctgcttnaga ggaccaagaa    600
aanattactt attggntggg tattaaagct aagggggggn cctaaggggn tttggnnggc    660
cc                                                                  662

<210> SEQ ID NO 107
<211> LENGTH: 792
```

-continued

```
<212> TYPE: DNA
<213> ORGANISM: Glycine max
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
```

```
<222> LOCATION: (566)..(566)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (639)..(640)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (689)..(690)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (718)..(719)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
```

```
<222> LOCATION: (790)..(790)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t

<400> SEQUENCE: 107
tatttacaac tagtgttatc ggagaatgaa aaattgaaga ataataagtt cagctataat      60
aaactcgagg gaggaaaaac aaagaaattc atgataaata gatataactt attaaattta     120 agggtgtat ttgcacaccc tgaattatag agattcttat atctttgaga aaataattaa      180
attgggaaaa aagagataat gactgattga gatttgcctc agaattgttc gttttaatat     240
tggtacgaat ctaatggntt tatcctgaaa gatgctcaca agtattgagg gactaataaa     300
ttgnttataa actactacta aatgagatga gactttaagg ngtactgaag caatatcatt     360
taaaaaatga ctactcgcat ttgngttgag aaaatttatt ttcatgaaag naaattttnt     420
ccnttttang ataaagccat ttnncttaac cnnanggggga nataaaatgg cccccnttca     480
taaaaaacct accanctata taaatggatn tataccaacc ttcctangca ccatgccatt     540
gggatnggng gaattaaatt naaaangntt gcnttggaat gggtaaaaaa ttccaaaact     600
tnaacccccn ccacaatttt agtggccacn gnaatattnn ttanccgntg gncttttttc     660
caggaaaacg acccgtaacc aaangggggnn aaaagggaaa gggagatgga ttgcntgnng     720
gtntgaggct catcccnatt cccaaacatg ttngggnccc aaaaccgaag tnccctgga     780 ccatggatgn cn                                                         792

<210> SEQ ID NO 108
<211> LENGTH: 573
<212> TYPE: DNA
<213> ORGANISM: Glycine max
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
```

```
<222> LOCATION: (542)..(542)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (560)..(560)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t

<400> SEQUENCE: 108
gggactggct gtgactgatc tctctggtct aatctcttcc agctgctgga gaacttgatg      60
aacttctggt cgtgctgatg gagaaggatc aacacagtgc aaagcgagct tcaacgtgtt     120
tagcaactcg tcgccaactg tggatgcatc tctcatcaag tctgcatcaa aaacctcatt     180
tgtccactcc tctttgacaa ctgaggcaac ccactgaggc aaatctagtc cattcataga     240
caccccaggt gatttcctcg ttaggagttc taacaagata acaccaagac tgtagatatc     300
agttttagtg tttgctttct tgagctttga gagctcaggt gcccggtatc caatgctcca     360
gctgtagcta tcacgttgga attagcagca gttgacatca acccgagaaa gaccaaaatt     420
gcaatttagc anttgnattc ttataacaa cacaatggtt ggatgngang gtnccaagga     480
ttgangtttt ctgggaatga aaggganaaa caagccccgg gccaaagntt ggggttattt     540
tnaancctgg ngggncaaan aaangaaagg ttn                                  573

<210> SEQ ID NO 109
<211> LENGTH: 673
<212> TYPE: DNA
<213> ORGANISM: Glycine max
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
```

```
<222> LOCATION: (547)..(547)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (637)..(638)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (672)..(673)
<223> OTHER INFORMATION: n is a, c, g, or t

<400> SEQUENCE: 109
gggactggct gtgactgatc tctctggtct aatctcttcc agctgctgga gaacttgatg    60
aacttctggt cgtgctgatg gagaaggatc aacacagtgc aaagcgagct tcaacgtgtt   120
tagcaactcg tcgccaactg tggatgcatc tctcatcaag tctgcatcaa aaacctcatt   180
tgtccactcc tctttgacaa ctgaggcaac ccactgaggc aaatctagtc cattcataga   240
caccccaggt gatttcctcg ttaggagttc taacaagata acaccaagac tgtagatatc   300
agttttagtg tttgctttct tgagcttttg agaagctcag gtgcccggta tcccaaatgc   360
ttccagctgt agcttatcac cgttgggaat taagcagcaa gttggacatt caacccggag   420
naaaagaccc aaaaattttg caaattttta agcaatttng gnanttcttn aatcaaggcc   480
aaccaccaat tggnttggga atggtggaag ggtttcccca atggtaattg gaagggtttc   540
ttccctnggg gaaatggaa agggcaana aaacaaaggc ccaacngggg ccccaaaggt    600
nttttggggg ccttatttt tncnaatncc ctttggnngg ggncccaaat tcnaaantgg   660
aaattggntt tnn                                                      673

<210> SEQ ID NO 110
<211> LENGTH: 564
```

<212> TYPE: DNA
<213> ORGANISM: Glycine max

<400> SEQUENCE: 110

```
actggctgtg actgatctct ctggtctaat ctcttccagc tgctggagaa cttgatgaac    60
ttctggtcgt gctgatggag aaggatcaac acagtgcaaa gcgagcttca acgtgtttag   120
caactcgtcg ccaactgtgg atgcatctct catcaagtct gcatcaaaaa cctcatttgt   180
ccactcctct ttgacaactg aggcaaccca ctgaggcaaa tctagtccat tcatagacac   240
cccaggtgat ttcctcgtta ggagttctaa caagataaca ccaagactgt agatatcagt   300
tttagtgttt gctttcttga gctttgagag ctcaggtgcc cggtatccca atgctccagc   360
tgtagctatc acgttggaat tagcagcagt tgacatcaac ccgagaaaga ccaaaatctg   420
caatttagc atttgtattc tcatcaagca acacattgct ggatgtgagg ttcccatgta   480
tgatgttctc ctgggaatga aggcagaaca agccacggcc aagcttggct atttcatcct   540
tgtggccaat caatgaatgg tcat                                          564
```

<210> SEQ ID NO 111
<211> LENGTH: 456
<212> TYPE: DNA
<213> ORGANISM: Glycine max
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (429)..(430)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t

<400> SEQUENCE: 111

```
actatgagga cagaaaaagg agtccctcca gttgctggtg gtgatgttga agcgggtggg    60
gaggctggag ggaaactagt ccattttgat ggaccaatgg cttttacagc tgatgatctc   120
ttgtgtgcaa cagctgagat catgggaaag agcacctatg gaactgttta taaggctatt   180
ttggaggatg gaagtcaagt tgcagtaaag agattgaggg aaaagatcac taaaggtcat   240
agagaatttg aatcanaagt cagtgttcta ggaaaaatta nacacccccaa tgtttggtt   300 ntgaggccta ttacttggga cccaaagggg aaaagcttnt ggttttgat tcatgtntaa   360 aggaagtctt gcttntttcc tacatggnaa gtttcggggc tgtctttnat taangggtngg   420 gngngctgnn tttaattata attnggngtt tacctt                             456
```

<210> SEQ ID NO 112
<211> LENGTH: 592
<212> TYPE: DNA
<213> ORGANISM: Glycine max
<220> FEATURE:
<221> NAME/KEY: misc_feature
<222> LOCATION: (463)..(464)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t

<400> SEQUENCE: 112

```
actatgagga cagaaaaagg agtccctcca gttgctggtg gtgatgttga agcaggtggg    60
gaggctggag ggaaactagt ccattttgat ggaccaatgg cttttacagc tgatgatctc   120
ttgtgtgcaa cagctgagat catgggaaag agcacctatg gaactgttta taaggctatt   180
ttggaggatg gaagtcaagt tgcagtaaag agattgaggg aaaagatcac taaaggtcat   240
agagaatttg aatcagaagt cagtgttcta ggaaaaatta gacacccccaa tgtttggct   300 ctgagggcct attacttggg acccaaaggg gaaaagcttc tggttttga ttacatgtct    360 aaaggaagtc ttgcttcttt cctacatggt aagtttcgtg tgctgttctt tcattaagtg   420
ttgggtgtgc tggtctttaa ttataatttg gagtttacct tannaatctg gataattcta   480
```

```
atcggagaac agncaaacaa aanccctaag gaacaaccct tanctttaat atccatatca    540
ataagngaan tatttcttgg tcatcttgat gcagggggg gnactgaaca tt             592
```

<210> SEQ ID NO 113
<211> LENGTH: 460
<212> TYPE: DNA
<213> ORGANISM: Glycine max
<220> FEATURE:
<221> NAME/KEY: misc_feature
<222> LOCATION: (438)..(438)
<223> OTHER INFORMATION: n is a, c, g, or t

<400> SEQUENCE: 113

```
gggactggct gtgactgatc tctctggtct aatctcttcc agctgctgga gaacttgatg    60
aacttctggt cgtgctgatg gagaaggatc aacacagtgc aaagcgagct tcaacgtgtt   120
tagcaactcg tcgccaactg tggatgcatc tctcatcaag tctgcatcaa aaacctcatt   180
tgtccactcc tctttgacaa ctgaggcaac ccactgaggc aaatctagtc cattcataga   240
caccccaggt gatttcctcg ttaggagttc taacaagata acaccaagac tgtagatatc   300
agttttagtg tttgctttct tgagctttga gagctcaggt gcccggtatc ccaatgcttc   360
agctgtagct atcacgttgg aattagcagc agttgacatc aaccgagaaa gaccaaaatc   420
tgcaatttta gcatttgnat tctcattaaa caacacaatg                         460
```

<210> SEQ ID NO 114
<211> LENGTH: 566
<212> TYPE: DNA
<213> ORGANISM: Glycine max
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (354)..(355)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature

```
<222> LOCATION: (390)..(390)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t

<400> SEQUENCE: 114
gggactggct gtgactgatc tctctggtct aatctcttcc agctgctgga gaacttgatg      60
aacttctggt cgtgctgatg agaaggatc aacacagtgc aaagcgagct tcaacgtgtt     120
tagcaactcg tcgccaactg tggatgcatc tctcatcaag tctgcatcaa aaacctcatt    180
tgtccactcc tctttgacaa ctgaggcaac ccactgaggc aaatctagtc cattcataga    240
cnccccaggt gatttcntcg ttaggagttn taacaagata acaccaagac tgtagatatc    300
agttttagtg tttgctttct tgagctttga gagttaaggg ncccggantc ccanngntcn    360
agttgnagtt atancgttgg aattagcagn agttgcntca accgaaaaag accaaaatct    420
gaattttagc atttgttttt catcaagcaa cacattgntg gatgngaggt cccatgtatg    480
atgttctcct gggaatgaag gcaaacaagc ccgggccaag gcttgggcta ttttaatcct    540
tggtggccaa acaatgaaag gttnat                                         566

<210> SEQ ID NO 115
<211> LENGTH: 16
<212> TYPE: DNA
<213> ORGANISM: Glycine max

<400> SEQUENCE: 115
gactgcgtac caattc                                                     16

<210> SEQ ID NO 116
<211> LENGTH: 16
<212> TYPE: DNA
<213> ORGANISM: Glycine max

<400> SEQUENCE: 116
gatgagtcct gagtaa                                                     16

<210> SEQ ID NO 117
<211> LENGTH: 22
<212> TYPE: DNA
<213> ORGANISM: Glycine max

<400> SEQUENCE: 117
gggtttcaga taaccgtggt cg                                              22

<210> SEQ ID NO 118
<211> LENGTH: 25
<212> TYPE: DNA
<213> ORGANISM: Glycine max

<400> SEQUENCE: 118
ttgcagatat tttagttgat tggcc                                           25
```

```
<210> SEQ ID NO 119
<211> LENGTH: 24
<212> TYPE: DNA
<213> ORGANISM: Glycine max

<400> SEQUENCE: 119
agttgattgg ctcaaaccat ggcc                                              24

<210> SEQ ID NO 120
<211> LENGTH: 20
<212> TYPE: DNA
<213> ORGANISM: Glycine max

<400> SEQUENCE: 120
ttgcgtgtga tcggtattac                                                   20

<210> SEQ ID NO 121
<211> LENGTH: 20
<212> TYPE: DNA
<213> ORGANISM: Glycine max

<400> SEQUENCE: 121
tacctgagtt ctctcaagtc                                                   20

<210> SEQ ID NO 122
<211> LENGTH: 252
<212> TYPE: DNA
<213> ORGANISM: Glycine max
<220> FEATURE:
<221> NAME/KEY: misc_feature
<222> LOCATION: (20)..(20)
<223> OTHER INFORMATION: n is a, c, g, or t

<400> SEQUENCE: 122
gatttagact gcgctgactn tcaaaggaga ctggaatttc tccactgaaa ttattcagtg        60
acaaatcaag ctgcctaagc gaggaaatgt ttgcaatgct tgaaggaata tgtccactaa      120
attggtttct actcaaaatc agaacagaaa gattacgcaa tctacctaaa ctttgaggga      180
tttgattgtc aaggaggttg ttctctgcat tcagcagtgt aagtgaggat aaattagaga      240
gggtagcagg ca                                                          252

<210> SEQ ID NO 123
<211> LENGTH: 199
<212> TYPE: DNA
<213> ORGANISM: Glycine max

<400> SEQUENCE: 123
ttatcatcca aattaaaatt gaaaacttta atacaaatgc acattttgga gccattcatg        60
tcatctcttg gtctgagtct tatcattctg tggattgaat tcatggtttc tcttatgaca      120
ttgttgccaa gtaatactac tatataaatt cagatttggg tttctgataa ccgtggtcgt      180
taatactata tataatacc                                                   199

<210> SEQ ID NO 124
<211> LENGTH: 213
<212> TYPE: DNA
<213> ORGANISM: Glycine max

<400> SEQUENCE: 124
ttatcatcca aattaaaatt gaaaacttta atacaaatgc acattttgga gccattcatg        60
tcatctcttg gtctgagtct tatcattctg tggattgaat tcatggtttc tcttatctta      120
```

```
tgaattcatg gtttctctta tcttatgaca ttgttgccaa gtaatactac tatataaatt    180
cagatttggg tttcagataa ccgtggtcgt taa                                 213

<210> SEQ ID NO 125
<211> LENGTH: 133
<212> TYPE: DNA
<213> ORGANISM: Glycine max

<400> SEQUENCE: 125
ttaaagggat atgttttttt cactaatgct gtaaaaattc acccagattt ttgcattttc     60
tttgaaaaaa tgttagatat atcatgtttt tttacaagca ttacaataat attcactcgt    120
atattaggaa ttc                                                       133

<210> SEQ ID NO 126
<211> LENGTH: 113
<212> TYPE: DNA
<213> ORGANISM: Glycine max

<400> SEQUENCE: 126
ttaaagggat atgttttttt cactaatgtc gtaaaaattc accccaaatt tttgcatttt     60
atcatgtttt tttacaagca ttacaataat attcactcgt atattaggaa ttc           113

<210> SEQ ID NO 127
<211> LENGTH: 397
<212> TYPE: DNA
<213> ORGANISM: Glycine max

<400> SEQUENCE: 127
ttaaaacctt gcgtgtgatc ggtattacag tacgcagggc caatcaacta aaatatctgc     60
aaacgataat ataattataa gaaaagaca cactttgagg gcattttga cttgagagaa      120 ctcaggtatc aatctaaaag caacgctgtt caccttgagc tgaaacacct ggaggagaaa    180
gcaaagcaaa ccaaacgcga gagagaaata agaacggaa acagagagag agaggaag      240 gaccttgttc aaagcaacgg ggacaacttt agagccctgg cgcgcgtggg ggtcaataag    300
cgtaacctgg ctgaggagag cctcggcgtc gtccttgctg aagcagaaga ggaagagcac    360
gagaccaaga gaaactcctc ggaagcaacg ggaattc                             397

<210> SEQ ID NO 128
<211> LENGTH: 405
<212> TYPE: DNA
<213> ORGANISM: Glycine max

<400> SEQUENCE: 128
ttaaaacctt gcgtgtgatc ggtattacag tacgcagggc catggtttga gccaatcaac     60
taaaatattt gcaaacgata atataattat aagaaaaaga ctcactttga gggcattttt    120
gacttgagag aactcaggta tcaatctaaa agcaacgctg ttcaccttga gctgaaacac    180
ctggaggaga agcaaagca aaccaaacgc gagagagaaa taagaacgg aaacagagag     240 agaggaagga ccttgttcaa agcaacgggg acaactttag agccctggcg cgcgtggggg    300
tcaataagcg taacctggct gaggagagcc tcggcgccgt ccttgctgaa gcagaagagg    360
aagagcccga gaccaagaga aactcctcgg aagcaacggg aattc                    405

<210> SEQ ID NO 129
<211> LENGTH: 161
<212> TYPE: DNA
<213> ORGANISM: Glycine max
```

```
<400> SEQUENCE: 129
ttaaatgaaa atcgatcaaa atgaaataat atatgctttt tttagttggg ttcaagtact     60
tttttttatt gaaaaaatcg acccaagttg aaacacatgt ttgagaattg ttttgtgcat    120
ccaacgtttt tcttgtacaa tcagctgtga gaggggaatt c                        161

<210> SEQ ID NO 130
<211> LENGTH: 162
<212> TYPE: DNA
<213> ORGANISM: Glycine max

<400> SEQUENCE: 130
ttaaatgaaa atcgatcaaa atgaaataat atatgctttt tttagttgtg ttcaagtaac     60
ttttttttat tgaaaaaatc gacccaagtt gaaacacatg tttgagaatt gttttgtgca    120
tccaacgttt tcttgtaca atcagctgtg agaggggaat tc                        162

<210> SEQ ID NO 131
<211> LENGTH: 18
<212> TYPE: DNA
<213> ORGANISM: Glycine max

<400> SEQUENCE: 131
agggatatgt ttttttca                                                    18

<210> SEQ ID NO 132
<211> LENGTH: 18
<212> TYPE: DNA
<213> ORGANISM: Glycine max

<400> SEQUENCE: 132
gaattcctaa tatacgag                                                    18

<210> SEQ ID NO 133
<211> LENGTH: 21
<212> TYPE: DNA
<213> ORGANISM: Glycine max

<400> SEQUENCE: 133
atctcttggt ctgagtctta t                                                21

<210> SEQ ID NO 134
<211> LENGTH: 25
<212> TYPE: DNA
<213> ORGANISM: Glycine max

<400> SEQUENCE: 134
tggtttctct tatgacattg ttgcc                                            25

<210> SEQ ID NO 135
<211> LENGTH: 26
<212> TYPE: DNA
<213> ORGANISM: Glycine max

<400> SEQUENCE: 135
ttctcttatc ttatgacatt gttgcc                                           26
```

```
<210> SEQ ID NO 136
<211> LENGTH: 20
<212> TYPE: DNA
<213> ORGANISM: Glycine max

<400> SEQUENCE: 136
tattaacgac cacggttatc                                              20
```

ISOLATED SOYBEAN CYST NEMATODE AND SOYBEAN SUDDEN DEATH SYNDROME POLYPEPTIDES

CROSS REFERENCE TO RELATED APPLICATIONS

This application is a divisional of the U.S. Utility application Ser. No. 09/772,134, filed Jan. 29, 2001, now abandoned herein incorporated by reference in its entirety which claims priority to the U.S. Provisional Application Ser. No. 60/178,811, filed Jan. 28, 2000, herein incorporated by reference in its entirety.

TECHNICAL FIELD

The present invention relates to plant breeding and plant genetics. More particularly, the invention relates to soybean cyst nematode and soybean sudden death syndrome resistance genes, soybean cyst nematode and soybean sudden death syndrome resistant soybean lines, and methods of breeding and engineering the same.

| Table of Abbreviations | |
|---|---|
| AFLP | amplified fragment length polymorphism |
| BAC | bacterial artificial chromosome |
| bp | base pair |
| Cf | tomato genes for resistance to *Cladosporium fulvus* |
| FAM | 6-carboxyfluorescein |
| FI | female index of parasitism |
| indel | a nucleotide insertion or deletion |
| MMAS | molecular marker-assisted selection |
| QTL | quantitative trait loci |
| RAPD | random amplified polymorphic DNA |
| RFLP | restriction fragment length polymorphism |
| rhg1 and Rhg4 | genetic loci conferring resistance to *Heterodera glycines* |
| RIL | recombinant inbred line |
| SCN | soybean cyst nematode |
| SDS | sudden death syndrome |
| SSR | microsatellite |
| TAMRA | 6-carboxy-N,N,N'5N'tetrachlorofluorescein |
| TET | 6-carboxy-4,7,2',7',tetrachlorofluorescein |

BACKGROUND OF THE INVENTION

Soybeans are a major cash crop and investment commodity in North America and elsewhere. Soybean oil is one of the most widely used edible oils, and soybeans are used worldwide both in animal feed and in human food production.

The soybean cyst nematode (SCN), *Heterodera glycines*, is a widespread pest of soybeans in the American continent. Reported first in Japan more than 75 years ago, since the first reports in North Carolina in 1954, SCN continues its spread toward almost all soybean-cultivated soils. Known as a small plant-parasitic roundworm that attacks the roots of soybeans, it reproduces very quickly, survives in the soil for many years in the absence of a soybean crop, and can cause substantial soybean crop yield losses.

Resistant soybean varieties are an effective tool available for SCN management. There are multiple sources for soybean cyst nematode resistance genes in commercial soybean varieties (PI88788, Peking and PI209332), and several have been used to develop cultivars (Myers & Anand (1991), *Euphytica* 55:197-201; Rao-Arrelli et al. (1988) *Crop Sci* 28:650-652). All the described loci involved in the resistance to SCN are reported to be quantitative. (Concibido et al. (1997) *Crop Sci* 37:258-264; Concibido (1996) *Theor Appl Genet.* 93:234-241; Webb et al. (1995) *Theor Appl Genet.* 91:574-581; Rao-Arrelli et al. (1992) *Crop Sci* 32:862-864; Matthews et al. (1991) *Soybean Genetics Newsletter*; Rao-Arrelli et al., 1988). They differ by their chromosomal position (LG A2, G, B, I, F, J and E) and race of the pathogen against which they confer the resistance (e.g. Race 1, 3, 5 or 14). SCN resistance is simply inherited, but field resistance is oligogenic due to the existence of variation among SCN populations that are described as "races" (Riggs and Schmidt (1988) *J Nematol* 20:392-395).

One gene, rhg1, provides the major portion of resistance to SCN race 3 across many genotypes derived from Peking (Chang et al. (1997) *Crop Sci* 372:965-971; Mathews et al. (1998) *Theor Appl Genet.* 97:1047-1052; Mahalingam et al. (1995) *Breed Sci* 45:435-445); PI437654 (Prabhu et al. (1999) *Crop Sci* 39:982-987; Webb et al., 1995), >PI88788= (Bell-Johnson et al. (1998) *Soybean Genet Newslett* 25:115-118; Concibido et al., 1997; Cregan et al. (1999a) *Crop Sci* 39:1464-1490; Cregan et al. (1999b) *Theor Appl Genet.* 99:811-818; Cregan et al. (1999c) *Theor Appl Genet.* 99:918-928), >PI209332=(Concibido et al., 1996), or >PI90763= (Concibido et al., 1997). A second gene for SCN resistance, Rhg4, provides an equal portion of resistance to SCN race 3 across genotypes derived from Peking (Chang et al., 1997; Mathews et al., 1998; Mahalingam et al., 1995); and PI437654 (Prabhu et al., 1999; Webb et al., 1995) but not PI88788, PI209332 or PI90763 (Concibido et al., 1996; Concibido et al., 1997). Cytological studies suggest PI437654 and Peking derived resistances share mechanisms (pronounced necrosis and cell wall appositions) not seen in PI88788 in response to race 3 (Mahalingham et al. (1996) *Genome* 39:986-998). These differences in mechanism may derive from distinct alleles at Rhg4, rhg1 and/or other defense associated loci.

DNA molecular markers linked to SCN/SDS resistance loci can be used to develop effective plant breeding strategies. In general, molecular markers are abundant, often co-dominant, and suitable for rapid screening at the seedling stage. Genetic linkage maps of soybean based on RFLP, RAPD, AFLP, and microsatellite markers have been described. See Brown et al. (1987) *Principles and Practice of Nematode Control in Crops*, pp 179-232, Academic Press, Orlando Fla.; Concibido et al., 1996; Concibido et al., 1997; Mahalingham et al., 1995; Meksem et al. (1999) *Theor Appl Genet.* 99:1131-1142; Meksem et al. (2000) *Theor Appl Genet.* 101:747-755; Webb et al., 1995; Weiseman et al. (1992) *Theor Appl Genet.* 85:136-138; Lark et al. (1993) *Theor Appl Genet.* 86:901-906; Shoemaker and Specht (1995) *Crop Sci* 35:436-446; Chang et al., 1997; Keim et al. (1997) *Crop Sci* 37:537-543).

All such markers have a limit of resistance trait predictability based principally on proximity of the marker to the resistance locus. In some cases, the interpretative value of genetic linkage experiments can be augmented through the simultaneous or serial detection of more than one genetic marker, although this also incurs additional time and resources. Thus, there is a need for a reliable cost-effective method for detecting SCN or SDS resistance using genetic markers. Optimally, a genetic marker comprises a resistance gene.

Therefore, it is of particular importance, both to the soybean breeders and to farmers, to identify, genetic loci for resistance to SCN and SDS. Having knowledge of the loci for resistance to SCN and SDS, those of ordinary skill in the art can breed or engineer SCN and SDS resistant soybeans. Soybean resistance can be further provided to a non-resistant

SUMMARY OF THE INVENTION

The present invention discloses an isolated and purified genetic marker associated with SCN/SDS resistance in soybeans, said marker mapping to linkage group G in the soybean genome. Preferably, the marker has a sequence identical to any one of SEQ ID NOs:1, 3, and 5. Representative corresponding markers associated with SCN/SDS susceptibility are set forth as SEQ ID NOs:2, 4, and 6.

Also disclosed is an isolated and purified genetic marker associated with SCN/SDS resistance in soybeans, said marker mapping to linkage group A2 in the soybean genome. Preferably, the marker has a sequence identical to any one of SEQ ID NOs:7, 9, and 11. Representative corresponding markers associated with SCN/SDS susceptibility are set forth as SEQ ID NOs:8, 10, and 12.

The present invention further provides a plant, or parts thereof, which evidences an SCN/SDS resistance response comprising a genome, homozygous with respect to genetic alleles which are native to a first parent and normative to a second parent of the plant, wherein said second parent evidences significantly less resistant response to SCN/SDS than said first parent and said improved plant comprises alleles from said first parent that evidences resistance to SCN/SDS in hybrid combination in at least one locus selected from: a locus mapping to linkage group G and mapped by one or more of the markers set forth as SEQ ID NOs:1, 3, and 5, a locus mapping to linkage group A2 and mapped by one or more of the markers set forth as SEQ ID NOs:7, 9, and 11; or combinations thereof, said resistance not significantly less than that of the first parent in the same hybrid combination, and yield characteristics which are not significantly different than those of the second parent in the same hybrid combination.

In another embodiment, a plant of the present invention, or parts thereof, comprises the progeny of a cross between first and second inbred lines, alleles conferring SCN/SDS resistance being present in the homozygous state in the genome of one or the other or both of said first and second inbred lines such that the genome of said first and second inbreds together donate to the hybrid a complement of alleles necessary to confer the SCN/SDS resistance. Further disclosed are hybrid plants derived therefrom.

Also disclosed herein are isolated and purified biologically active SCN/SDS resistance polypeptide and an isolated and purified nucleic acid molecule encoding the same are disclosed. Preferably, the polypeptide comprises a soybean SCN/SDS resistance polypeptide. Chimeric genes comprising the isolated and purified nucleic acid molecules encoding a SCN/SDS resistance polypeptide are also provided.

In one embodiment, the nucleic acid molecule encoding a SCN/SDS resistance gene comprises an isolated soybean rhg1 gene that confers SCN/SDS resistance to a non-resistant host organism. The gene is capable of conveying *Heterodera glycines*-infestation resistance, *Fusarium solani*-infection resistance, or both *Heterodera glycines*-infestation resistance or *Fusarium solani*-infection resistance to a non-resistant plant germplasm, the gene located within a quantitative trait locus mapping to linkage group G and mapped by genetic markers of SEQ ID NOs:1, 3, and 5, said gene located along said quantitative trait locus between said markers. Preferably, the polypeptide comprises (a) a polypeptide encoded by a nucleic acid sequence set forth as SEQ ID NO:13; (b) a polypeptide encoded by a nucleic acid having homology to a DNA sequence set forth as SEQ ID NO:13; (c) a polypeptide encoded by a nucleic acid capable of hybridizing under stringent conditions to a nucleic acid comprising a sequence or the complement of a sequence set forth as SEQ ID NO:13; (d) a polypeptide which is a biologically functional equivalent of a peptide set forth as SEQ ID NO:14; or (e) a polypeptide comprising a fragment of a polypeptide of (a), (b), (c) or (d).

In another embodiment, the nucleic acid molecule encoding a SCN resistance polypeptide comprises an isolated soybean Rhg4 gene that is capable of conveying *Heterodera glycines*-infestation resistance to a non-resistant plant germplasm, said gene located within a quantitative trait locus mapping to linkage group A2 and mapped by the AFLP markers of SEQ ID NOs:7, 9, and 11, said gene located along said quantitative trait locus between said markers. Preferably, the nucleic acid molecule comprises any one of SEQ ID NOs:16-19.

The present invention further provides an isolated SCN/SDS resistance gene promoter region, or functional portion thereof, comprising an about 90 kb fragment of soybean genomic clone 73P6 between BamHI restriction sites and 21d9 between HinDIII restriction site. The genomic clone is available from the Forrest BAC library described in Meksem et al (2000) *Theor Appl Genet*. 101 5/6:747-755, available through Southern Illinois University-Carbondale (Carbondale, Ill.), Texas A&M University BAC center (College Station, Tex.), and Research Genetics (Huntsville, Ala.). Preferably, the isolated promoter region comprises the nucleotide sequence of SEQ ID NO:15 or a sequence substantially similar to SEQ ID NO:15. The SCN/SDS resistance gene promoter region can be operably linked to heterologous sequence.

A recombinant host cell comprising an isolated and purified nucleic acid molecule of the present invention is also disclosed, as is a transgenic plant having incorporated into its genome an isolated and purified nucleic acid molecule. In one embodiment, the nucleic acid molecule comprises encodes a SCN/SDS resistance polypeptide and is present in said genome in a copy number effective to confer expression in the plant of the SCN/SDS resistance polypeptide. Seeds, parts or progeny of the transgenic plant are also disclosed.

Further provided is a method for detecting a nucleic acid molecule that encodes an SCN/SDS resistance polypeptide in a biological sample comprising nucleic acid material is also disclosed. The method comprises: (a) hybridizing an isolated and purified nucleic acid molecule of the present invention under stringent hybridization conditions to the nucleic acid material of the biological sample, thereby forming a hybridization duplex; and (b) detecting the hybridization duplex. Preferably, the isolated and purified nucleic acid molecule comprises any of SEQ ID NOs:13 and 16-19.

An assay kit for detecting the presence, in biological samples, of an SCN/SDS resistance polypeptide is also disclosed. In one embodiment, the kit comprises a first container that contains a nucleic acid probe identical or complementary to a segment of at least ten contiguous nucleotide bases of a nucleic acid molecule of the present invention, preferably a nucleotide sequence of any one of SEQ ID NOs:13 and 16-19. In another embodiment, the kit comprises a nucleic acid probe or primer identical to any one of SEQ ID NOs:1, 3, 5, 7, 9, and 11, or portion thereof.

A method for identifying soybean sudden death syndrome (SDS) resistance or soybean cyst nematode (SCN) resistance in a soybean plant using a SDS resistance gene, a SCN resistance gene, or DNA segments having homology to a SDS resistance gene or to an SCN resistance gene is also disclosed. In one embodiment, the method comprises: (a) probing nucleic acids obtained from the soybean plant with a probe derived from said SDS resistance gene or from said SCN resistance gene or from said DNA segment having homology to said SDS resistance gene or to said SCN resistance gene; and observing hybridization of said probe to said nucleic acids, the presence of said hybridization indicating SDS or SCN resistance in said soybean plant. In another embodiment, the method comprises (a) detecting a molecular marker linked to a quantitative trait locus associated with SCN/SDS resistance, wherein the molecular marker is the sequence set forth as any one of SEQ ID NOs:1, 3, 5, 7, 9, and 11; and (b) determining the presence of SCN/SDS resistance as detection of the molecular marker and determining the absence of SCN/SDS resistance as failure to detect the molecular marker of (b).

A method of reliably and predictably introgressing SCN/SDS resistance genes into non-resistant soybean germplasm is also disclosed. The method comprises: using one or more nucleic acid markers for marker assisted selection among soybean lines to be used in a soybean breeding program, wherein the nucleic acid markers map to linkage groups G or A2 and wherein the nucleic acid markers are selected from among any of SEQ ID NOs: 1, 3, 5, 7, 9, and 11; and introgressing said resistance gene into said non-resistant soybean germplasm.

A soybean plant, or parts thereof, which evidences a SCN/SDS resistance response is also disclosed. The plant comprises a genome, homozygous with respect to genetic alleles which are native to a first parent and non-native to a second parent of the soybean plant, wherein said second parent evidences significantly less resistant response to SCN/SDS than said first parent, and said improved plant comprises alleles from said first parent that evidences resistance to SCN/SDS in hybrid combination of at least one locus selected from: a locus mapping to linkage group G and mapped by one or more of the markers set forth as SEQ ID NOs:1, 3, and 5, a locus mapping to linkage group A2 and mapped by one or more of the markers set forth in SEQ ID NOs:7, 9, and 11; or combinations thereof, said resistance not significantly less than that of the first parent in the same hybrid combination, and yield characteristics which are not significantly different than those of the second parent in the same hybrid combination.

The soybean plant, or parts thereof, can further comprise the progeny of a cross between first and second inbred lines, alleles conferring SCN/SDS resistance being present in a homozygous state in the genome of one or the other or both of said first and second inbred lines such that the genome of said first and second inbreds together donate to the hybrid a complement of alleles necessary to confer the SCN/SDS resistance. Thus, an SCN/SDS resistant hybrid, or parts thereof, formed with the soybean plant is also disclosed, as is a soybean plant, or parts thereof, formed by selfing the SCN/SDS resistant hybrid.

A method of positional cloning of a nucleic acid is also disclosed. The method comprises: (a) identifying a first nucleic acid genetically linked to a SCN/SDS resistance locus, wherein the first nucleic acid maps between two markers selected from SEQ ID NOs:1-12; and (b) cloning the first nucleic acid. Optionally, the first nucleic acid can comprise the rhg1 locus or the Rhg4 locus.

A method for producing an antibody that specifically recognizes a SCN/SDS resistance polypeptide is also disclosed. The method comprises (a) recombinantly or synthetically producing a SCN/SDS resistance polypeptide, or portion thereof; (b) formulating the polypeptide of (a) whereby it is an effective immunogen; (c) administering to an animal the formulation of (b) to generate an immune response in the animal comprising production of antibodies, wherein antibodies are present in the blood serum of the animal; and (d) collecting the blood serum from the animal of (c) comprising antibodies that specifically recognize a SCN/SDS resistance polypeptide. Also provided is an antibody produced by the disclosed method.

Methods for identifying a candidate compound as a modulator of SCN/SDS resistance activity is also disclosed. Such methods include but are not limited to cell-based assays of SCN/SDS resistance gene expression, assays of specific binding to SCN/SDS regulatory elements, and assays of specific binding to SCN/SDS polypeptides. Optionally, the screening methods are adapted to a high-throughput format.

In one embodiment, the method comprises: (a) exposing a cell sample with a candidate compound to be tested, the cell sample containing at least one cell containing a DNA construct comprising a modulatable transcriptional regulatory sequence of an SCN/SDS resistance-encoding nucleic acid and a reporter gene which is capable of producing a detectable signal; (b) evaluating an amount of signal produced in relation to a control sample; and (c) identifying a candidate compound as a modulator of SCN/SDS resistance activity based on the amount of signal produced in relation to a control sample.

The present invention also provides a method for identifying a substance that regulates SCN/SDS resistance gene expression using a chimeric gene that includes an isolated SCN/SDS resistance gene promoter region operably linked to a reporter gene. According to this method, a gene expression system is established that includes the chimeric gene and components required for gene transcription and translation so that reporter gene expression is assayable. To select a substance that regulates SCN/SDS resistance gene expression, the method further provides the steps of using the gene expression system to determine a baseline level of reporter gene expression in the absence of a candidate regulator; providing a plurality of candidate regulators to the gene expression system; and assaying a level of reporter gene expression in the presence of a candidate regulator. A candidate regulator is selected whose presence results in an altered level of reporter gene expression when compared to the baseline level. Preferably, the isolated SCN/SDS resistance gene promoter region used in this method comprises the sequence of SEQ ID NO:15, or functional portion thereof.

In another embodiment, the method comprises using an SCN/SDS regulatory sequence to identify a candidate substance that specifically binds to the regulatory sequence. According to the method, a SCN/SDS regulatory gene sequence is exposed to a candidate substance under conditions suitable for binding to a nucleic acid sequence, and a candidate regulator is selected that specifically binds to the SCN/SDS resistance gene promoter region. Preferably, the isolated SCN/SDS resistance gene promoter region used in this method comprises the sequence of SEQ ID NO:15, or functional portion thereof.

In another embodiment, a cell-free assay system is used and comprises: (a) exposing a SCN/SDS polypeptide of the present invention to a candidate compound; (b) assaying binding of the candidate compound to the SCN/SDS polypeptide; and (c) identifying a candidate compound as a putative modulator of SCN/SDS resistance activity based on specific binding of the candidate compound to the SCN/SDS polypeptide. Preferably, the SCN/SDS polypeptide comprises some or all of the amino acids of SEQ ID NO:14.

Figures 5A, 5B:
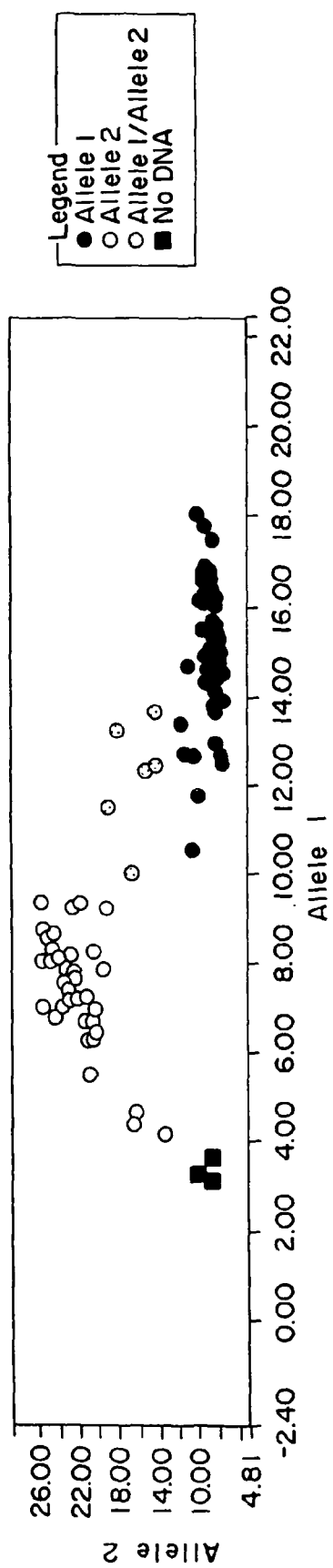

A method of modulating SCN/SDS resistance in a plant is also disclosed. The method comprises administering to the plant an effective amount of a substance that modulates expression of an SCN/SDS resistance activity-encoding nucleic acid molecule in the plant to thereby modulate SCN/SDS resistance in the plant. Preferably, the substance that modulates expression of an SCN/SDS resistance activity is discovered by a disclosed method of the present invention.

A method for providing a resistance characteristic to a plant is also disclosed. The method comprises introducing to said plant a construct comprising a nucleic acid sequence encoding an SCN/SDS resistance gene product operatively linked to a promoter, wherein production of the SCN/SDS resistance gene product in the plant provides a resistance characteristic to the plant. The construct can further comprises a vector selected from the group consisting of a plasmid vector or a viral vector. The SCN/SDS resistance gene product comprises a protein having an amino acid sequence of SEQ ID NO:14. The nucleic acid sequence comprises the nucleotide sequence of SEQ ID NO:13 or a nucleic acid that is substantially similar to SEQ ID NO:13, and which encodes an SCN/SDS resistance polypeptide.

The resistance characteristic is preferably nematode resistance, fungal resistance or combinations thereof. More preferably, the nematode resistance is *H. glycines* resistance, even more preferably race 3 *H. glycines* resistance.

In an alternative embodiment the construct further comprises another nucleic acid molecule encoding a polypeptide that provides an additional desired characteristic to the plant. Optionally, the method further comprises monitoring an insertion point for the construct in the plant genome; and providing for insertion of the construct into the plant genome at a location not associated with the resistance characteristic, the desired characteristic, or both the resistance and the desired characteristic. Preferably, the plant is a soybean plant.

The present invention also provides methods for providing a resistance characteristic to a plant is also disclosed, wherein a combination of genetic and non-genetic techniques is employed. The method comprises introducing to said plant a construct comprising a nucleic acid sequence encoding an SCN/SDS resistance gene product operatively linked to a promoter and provision of a substance that modulates SCS/SDS resistance gene activity, wherein production of the SCN/SDS resistance gene product in the plant, in combination with provision of the SCN/SDS resistance gene modulator, provides a resistance characteristic to the plant.

Accordingly, it is an object of the present invention to provide novel isolated polynucleotides and polypeptides relating to loci underlying resistance to soybean cyst nematode and soybean sudden death syndrome and methods employing same. The object is achieved in whole or in part by the present invention.

An object of the invention having been stated hereinabove, other objects and advantages will become evident as the description proceeds, when taken in connection with the accompanying Drawings and Examples as best described hereinbelow.

BRIEF DESCRIPTION OF THE DRAWINGS

FIG. 1 depicts new AFLP genetic markers for SCN/SDS resistance.

FIG. 1A presents genomic sequences of the both alleles (resistant Forrest and susceptible Essex) of the converted AFLP markers $E_{ATG}M_{CGA}87$ (SEQ ID NOs:1-2); $E_{CTA}M_{AGG}113$ (SEQ ID NOs:3, 4, 125, and 126); $E_{CGG}M_{AGA}116$ (SEQ ID NOs:5-6); $E_{CCG}M_{AAC}405$ (SEQ ID NOs:7, 8, 127, and 128), $E_{CCC}M_{ATG}161$ (SEQ ID NOs:9, 10, 129 and 130), $E_{CCA}M_{AGC}114$ (SEQ ID NOs:11-12). The italicized and underlined sequences represent the forward (CTAF and A2D8F, SEQ ID NOs: 131 and 120, respectively) and reverse (CTAR and A2D8R, which correspond to the reverse complements of the indicated sequences and which are disclosed as SEQ ID NOs: 132 and 121, respectively) sequence specific primers used. The bold capital sequences represent the original AFLP restriction site. The bold letters indicate the difference in sequences between the two alleles.

FIG. 1B presents genomic sequences of the two alleles (resistant and susceptible: SEQ ID NOs: 123 and 124, respectively) of the converted $E_{ATG}M_{CGA}87$ markers. The italic sequences represent the resistance specific TAQMANT™ probes TMA5—RE (SEQ ID NO: 134) and the susceptible allele specific probe TMA5-S (SEQ ID NO: 135). The standard font underlined sequence represent the TAQMANT™ forward (TMA5F; SEQ ID NO: 133) and reverse (TMA5R, corresponding to the reverse complement of the indicated sequence and which is disclosed as SEQ ID NO: 136) primers assay, the underlined italic sequence is the ATG4BACF primer (SEQ ID NO: 117) used for sequence extension of the $E_{ATG}M_{CGA}87$ marker, the BAC derived extended sequences are in small font capitals.

FIG. 2 depicts AFLPs for selecting SCN/SDS resistance.

FIG. 2A shows PCR amplification products using $E_{ATG}$ $M_{CGA}87$ sequence specific primers TMA5 forward and reverse (corresponding to SEQ ID NOs: 133 and 136): Lane 1-40 represent 40 RIL DNA, 41 and 42 are the two parents. F: Forrest; E: Essex; 1: resistant allele; 2: susceptible allele; H: heterozygote lines. The PCR products were separated by electrophoresis on a 4% (w/v) Metaphor gel.

FIG. 2B shows a partial AFLP autoradiograph profile of the $E_{CGG}M_{AGA}116$ marker. The six selective nucleotides step was replaced by MseI primer $M_{AGAGACT}$ and EcoRI primer E. Lane 7: Essex; Lane 8: Forrest; Lane 1 to 6 and 9 to 20 represent RIL DNA; 1: resistant allele; 2: susceptible allele FIG. 2C shows PCR amplification products using $E_{CTA}M_{AGG}113$ sequence specific primers CTA forward and reverse (corresponding to SEQ ID NOs: 131 and 132): Lane 1-40 represent 40 RIL DNA, 41 and 42 are the two parent. F: Forrest; E: Essex; 1: resistant allele; 2: susceptible allele; H: heterozygote lines. The PCR products were separated by electrophoresis on a 4% (w/v) Metaphor gel.

FIG. 2D shows PCR amplification products using $E_{CCG}$-$M_{AAC}405$ sequence specific primers A2D8 forward and reverse (corresponding to SEQ ID NOs: 120 and 121): Lane 1-40 represent 40 RIL DNA, 41 and 42 are the two parents F: Forrest; E: Essex; 1: resistant allele; 2: susceptible allele; H: heterozygote lines. The PCR products were separated by electrophoresis on a 4% (w/v) Metaphor gel.

FIG. 3 depicts a genetic and physical map showing the location of an Rhg4 gene relative to DNA markers. The location of the aspartokinase serine dehydrogenase (AK-HSDH) and the A2D8 marker are indicated as determined by restriction mapping of BAC DNA. The A2D8 sequences for Essex and Forrest alleles are deposited in GenBank as Accession Nos. AF286701 and AF286700, respectively. The l locus (l) position was estimated by relation to BARC-SAT_162 (Cregan et al., 1999c). Genetic mapping shows Rhg4 and A2D8 are both within the interval shown by the horizontal line and within a large insert clone, 100B10, that contains a 140 kbp insert (Zobrist et al. (2000) *Soybean Genet Newslett* 27:10-15).

FIG. 4 depicts the gene structure of the rhg1 gene and clones derived from Forrest genomic DNA.

FIG. 5 depicts detection of the A2D8 marker polymorphism using the TAQMANT™ assay and manual selection of genotypes. Eighty-six individuals from an F5 derived population of recombinant inbred lines from the cross of Essex× Forrest that segregate for resistance to SCN are shown.

FIG. 5A is an image of fluorescent signals viewed under the "dye component" field of the sequence detection software and the A2D8 genotypes were manually selected based on the ratio of FAM and TET signals. Allele 1 homozygous, Forrest type; FAM<<TET. Allele 2 homozygous, Essex type; TET<<FAM. Alleles 1 and 2 heterogeneous, Essex and Forrest type; TET less than 2 fold greater or lesser than FAM. Two selections were used, in the first (TAQMANT™ assay1) group of genotypes FAM 6-8 and TET 8-9 were considered susceptible. In the second (TAQMANT™ assay 2) group, they were considered heterogeneous.

FIG. 5B is a spreadsheet that contains scores (allele designations) for the samples as they were arranged in the 96 well plate. There was no DNA in wells E12, F12 and G12 (negative controls). There was Essex DNA in wells A1, C12 and D12. There was Forrest DNA in wells B2, A12 and B12. The RIL DNA was in well A3 to H11 in order by row from RIL1-RIL86 except samples E1 (RIL3) and E6 (RIL 43) that did not amplify. The RILs resistant to SCN had an index of parasitism F1<10% of the susceptible check resistant lines.

FIG. 6 depicts detection of the A2D8 marker polymorphism by PCR amplification and gel electrophoresis of soybean genotypes. Seventy-eight individuals from an F5 derived population of recombinant inbred lines from the cross of Essex x Forrest that segregate for resistance to SCN are shown.

FIG. 6A is an image of fluorescent signals viewed under the "dye component" field of the sequence detection software and the A2D8 genotypes were manually selected based on the ratio of FAM and TET signals. Lane 1,42 Essex; Lane 2 and 41 Forrest; Lanes 3-40 RILS 1-38.

FIG. 6B is a picture of an ehtidium-stained gel, showing resolution of gel electrophoresis markers. Lane 42 Essex; Lane 41 Forrest; Lanes 1-40 RILS 39-78. Asterisks indicate disagreements with the TAQMAN™ assay 1.

FIG. 7A-B presents the rhg1 gene sequence (SEQ ID NO:13).

FIG. 7C presents the rhg1 polypeptide (SEQ ID NO:14).

FIG. 7D shows sequences producing significant alignments using BLAST analysis.

FIG. 7E-F is an alignment between rhg1 protein (SEQ ID NO:14) and *Arabidopsis thaliana* hypothetical protein T18N14.120 (GenBank Accession T46070).

DETAILED DESCRIPTION OF THE INVENTION

Disclosed herein is the identification of AFLP markers that are genetically linked to the SCN/SDS resistance loci of Forrest. Further disclosed are purified and isolated SCN or SDS resistance genes, proximal sequences to SCN/SDS resistance genes, and SCN/SDS resistance-related genes.

The isolated and purified polynucleotide sequences disclosed herein can thus be used in a variety of applications pertaining to breeding and engineering soybeans having SCN and SDS resistance. For example, the isolated polynucleotides disclosed herein can be used in position-based or homology-based cloning of additional SCN/SDS resistance genes, including regulatory elements; in gene structure determination; in studies of genome organization and gene expression; in gene complementation experiments; in the isolation of additional DNA markers for gene manipulation and molecular marker assisted breeding; and in plant transformation and the production of transgenic plants.

The present invention also pertains to a soybean plant and methods of producing the same, which is resistant to soybean cyst nematodes (SCN). In one embodiment, the method comprises stable transformation of a plant with an rhg1 gene, disclosed herein. In another embodiment, the method comprises introgression in soybean of a trait enabling the plant to resist soybean cyst nematode (SCN) infestation. Additionally, the present invention relates to method of precise and accurate introgression of the genetic material conferring SCN resistance from one or more parent plants into the progeny.

The present invention also pertains to a soybean plant and methods of producing the same, which is resistant to soybean sudden death syndrome (SDS). In one embodiment, the method comprises stable transformation of a plant with an rhg1 gene, disclosed herein. In another embodiment, the method comprises introgression of the genetic material conferring SDS resistance from one or more parent plants into the progeny with precision and accuracy.

The invention differs from present technology in several regards. In one aspect, the present invention provides the first disclosure of the rhg1 gene sequence, thereby enabling transgenic approaches for providing SCN/SDS resistance. Further, the present invention provides a non-electorphoretic selection assay using nucleotide sequences of SCN/SDS resistance gene alleles. The disclosed nucleotide sequences of SCN/SDS resistance genes and associated genetic markers provide means for easily selecting resistant cultivars, for assembling many resistance genes in a single cultivar, for combining resistance genes in novel combinations, for identifying genes that confer resistance in new cultivars, and for predicting resistance in cultivars. The invention is used to improve selection for SDS and SCN resistance in soybean in breeding programs.

I. Traits

The term "phenotype" or "trait" each refer to any observable property of an organism, produced by the interaction of the genotype of the organism and the environment. A phenotype can encompass variable expressivity and penetrance of the phenotype. Exemplary phenotypes include but are not limited to a visible phenotype, a physiological phenotype, a susceptibility phenotype, a cellular phenotype, a molecular phenotype, and combinations thereof. Preferably, the phenotype is related to SCN/SDS resistance. The term "susceptibility phenotype" refers to an increased capacity or risk for displaying a phenotype, i.e. a susceptibility to SCN/SDS infection.

The term "complex trait" as used herein refers to a trait that is not inherited as predicted by classical Mendelian genetics. A complex trait results from the interaction of multiple genes, each gene contributing to the phenotype. Complex traits can be continuous or show threshold penetrance. In the field, SCN/SDS resistance is inherited as a complex trait.

The term "quantitative trait" is a complex trait that can be assessed quantitatively. Quantitation entails measurement of a trait across a continuous distribution of values. SCN/SDS resistance is a quantitative trait.

The term "SCN/SDS resistance" or "SCN/SDS resistance trait" as used herein refers to a cellular or organismal capacity for resistance to nematode or fungal infection, or both. Preferably, the nematode resistance is *Heterodera glycines* (the organism that causes SCN in soybeans) resistance, even more preferably race 3 *Heterodera glycines* resistance. The fungal resistance is preferably *Fusarium solani* (the organism that causes SDS in soybeans)-infection resistance. SCN resistance can be assayed in the field or in the greenhouse by methods known in the art, including but not limited to determination of an SCN index of parasitism as disclosed in Example 2, Meksem et al. (1999), and U.S. Pat. No. 6,096,944. SDS resistance can be scored by determination of disease incidence, disease severity, and disease index values as disclosed in Hnetkovsky et al. (1996) *Crop Sci* 36(2):393-400, Njiti et al. (1996) *Crop Sci* 36:1165-1170; and Matthews et al. (1991).

The term "SCN/SDS resistance" is used herein for convenience to describe traits, transgenic plants, polynucleotides, and polypeptides of the present invention. Therefore, the resistance characteristic conveyed by the polynucleotides and polypeptides of the present invention refers to any resistance characteristic as set forth herein and as would be apparent to one of ordinary skill in the art after reviewing the disclosure of the present invention.

The term "molecular phenotype" refers to a detectable feature of molecules in a cell or organism. Exemplary molecular phenotypes include but are not limited to a presence of a genetic marker nucleotide sequence, a presence of a SCN/SDS resistance gene sequence, a level of gene expression, a splice selection, a level of protein, a protein type, a protein modification, a level of lipid, a lipid type, a lipid modification, a level of carbohydrate, a carbohydrate type, a carbohydrate modification, and combinations thereof. Methods for observing, detecting, and quantitating molecular phenotypes are well known to one skilled in the art. See Sambrook et al., eds. (1989) *Molecular Cloning*, Cold Spring Harbor Laboratory Press, Cold Spring Harbor, N.Y., N.Y.; by Silhavy et al. (1984) *Experiments with Gene Fusions*, Cold Spring Harbor Laboratory Press, Cold Spring Harbor, N.Y., N.Y.; by Ausubel et al. (1992) *Current Protocols in Molecular Biology*, John Wylie and Sons, Inc. New York, N.Y.; Landgren et. al. (1988) *Science* 242:229-237; Bodanszky, et al. (1976) *Peptide Synthesis*, John Wiley and Sons, Second Edition, New York, N.Y.; Harlow and Lane (1988) *Antibodies: A Laboratory Manual*, Cold Spring Harbor Laboratory Press, Cold Spring Harbor, N.Y.; Ochman et al. (1990) in *PCR protocols: a Guide to Methods and Applications*, Innis et al. (eds.), pp. 219-227, Academic Press, San Diego, Calif.; Koduri and Poola (2001) *Steroids* 66(1):17-23; Regan et al. (2000) *Anal Biochem* 286(2):265-276; U.S. Pat. Nos. 6,096,555; 5,958,624; and 5,629,158.

II. Genetic Mapping

For genetic mapping, a representative population was generated as in Example 1. To detect genomic regions associated with resistance to SCN and resistance to SDS, the RILs were classified as Essex type or Forrest type for each marker. In some cases, SCN susceptibility and resistance was quantitatively determined according to a SCN female index (F1) of parasitism (Meksem, 1999) as described in Example 2. Markers were compared with SCN or SDS response scores by the F-test in analysis of variance (ANOVA) done with SAS (SAS Institute Inc., Cary, N.C., 1988). The probability of association of each marker with each trait was determined and a significant association was declared if $P \leq 0.05$ (unless noted otherwise in the text) since the detection of false associations is reduced in isogenic lines (Landers & Botstein (1989) *Genetics* 121:185-199; Paterson et al. (1990) *Genetics* 124:735-742).

Selected pairs of markers were analyzed by the two-way ANOVA using the general linear model (PROC GLM) procedure to detect non-additive interactions between the unlinked QTL (Chang et al. (1996) *Crop Sci* 36:965-971) or Epistat (Chase et al. (1997) *Theor Appl Genet*. 94:724-730). Non-additive interactions between markers which were significantly associated with SCN/SDS response were excluded when $P \geq 0.05$. Selected groups of markers were analyzed by multi-way ANOVA to estimate joint heritabilities for traits associated with multiple QTL. Joint heritability was determined from the $R^2$ term for the joint model in multi-way ANOVA.

Mapmaker-EXP 3.0 (Lander et al. 1987) was used to calculate map distances (cM, Haldane units) between linked markers and to construct a linkage map including traits as genes. The RIL (recombinant inbred line) and $F_3$ self genetic models were used. The $\log_{10}$ of the odds ratio (LOD) for grouping markers was set minimally at 2.0, and maximum distance was set at 30 cM. Conflicts were resolved in favor of the highest LOD score after checking the raw data for errors. Marker order within groups was determined by comparing the likelihood of many map orders. A maximum likelihood map was computed with error detection. Trait data were used for QTL analysis (Webb et al. 1995; Chang et al. 1997). The data were subjected to ANOVA (SAS Institute Inc., Cary, N.C.) with mean separation by LSD (Gomez and Gomez (1984). Graphs were constructed by Quattro Pro version 5.0 (Novell Inc., Orem, Utah).

III. Nucleotide Sequences of SCN/SDS Resistance Genes and Associated Genetic Markers The nucleic acid molecules provided by the present invention include the isolated nucleic acid molecules of SEQ ID NOs:1-13 and 15-114, sequences substantially similar to sequences of SEQ ID NOs:1-13 and 15-114, conservative variants thereof, plant-expressible variants thereof, subsequences and elongated sequences thereof, complementary DNA molecules, and corresponding RNA molecules. The present invention also encompasses genes, cDNAs, promoters, chimeric genes, and vectors comprising disclosed SCN/SDS resistance gene and SCN/SDS resistance gene marker nucleic acid sequences.

III.A. General Considerations

The term "nucleic acid molecule" refers to deoxyribonucleotides or ribonucleotides and polymers thereof in either single- or double-stranded form. Unless specifically limited, the term encompasses nucleic acids containing known analogues of natural nucleotides that have similar properties as the reference natural nucleic acid. Unless otherwise indicated, a particular nucleotide sequence also implicitly encompasses conservatively modified variants thereof (e.g. degenerate codon substitutions), complementary sequences, subsequences, elongated sequences, as well as the sequence explicitly indicated. The terms "nucleic acid molecule" or "nucleotide sequence" can also be used in place of "gene", "cDNA", or "mRNA". Nucleic acids can be derived from any source, including any organism.

The term "isolated", as used in the context of a nucleic acid molecule, indicates that the nucleic acid molecule exists apart from its native environment and is not a product of nature. An isolated DNA molecule can exist in a purified form or can exist in a non-native environment such as a transgenic host cell.

The term "purified", when applied to a nucleic acid, denotes that the nucleic acid is essentially free of other cellular components with which it is associated in the natural state. Preferably, a purified nucleic acid molecule is a homogeneous dry or aqueous solution. The term "purified" denotes that a nucleic acid or protein gives rise to essentially one band in an electrophoretic gel. Particularly, it means that the nucleic acid is at least about 50% pure, more preferably at least about 85% pure, and most preferably at least about 99% pure.

The term "substantially identical", in the context of two nucleotide or amino acid sequences, can also be defined as two or more sequences or subsequences that have at least 60%, preferably 80%, more preferably 90-95%, and most preferably at least 99% nucleotide or amino acid sequence identity, when compared and aligned for maximum correspondence, as measured using one of the following sequence comparison algorithms (described herein below under the heading Nucleotide and Amino Acid Sequence Comparisons) or by visual inspection. Preferably, the substantial identity exists in nucleotide sequences of at least 50 residues, more preferably in nucleotide sequence of at least about 100 residues, more preferably in nucleotide sequences of at least about 150 residues, and most preferably in nucleotide sequences comprising complete coding sequences.

In one aspect, polymorphic sequences can be substantially identical sequences. The term "polymorphic" refers to the occurrence of two or more genetically determined alternative sequences or alleles in a population. An allelic difference can be as small as one base pair.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogenous population of nucleic acid molecules. "Target sequence" is synonymous with "test sequence".

A preferred nucleotide sequence employed for hybridization studies or assays includes probe sequences that are complementary to or mimic at least an about 14 to 40 nucleotide sequence of a nucleic acid molecule of the present invention. Preferably, a probe comprises 14 to 20 nucleotides, or even longer where desired, such as 30, 40, 50, 60, 100, 200, 300, or 500 nucleotides or up to the full length of any of SEQ ID NOs:1-13, 15-114. Such fragments can be readily prepared by, for example, directly synthesizing the fragment by chemical synthesis, by application of nucleic acid amplification technology, or by introducing selected sequences into recombinant vectors for recombinant production. The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA). The phrase "binds substantially to" refers to complementary hybridization between a probe nucleic acid molecule and a target nucleic acid molecule and embraces minor mismatches that can be accommodated by reducing the stringency of the hybridization media to achieve the desired hybridization. Probe sequences can also hybridize specifically to duplex DNA under certain conditions to form triplex or other higher order DNA complexes. The preparation of such probes and suitable hybridization conditions are well known in the art.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2, Elsevier, New York, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.15 M NaCl at 65° C. An example of stringent wash conditions is 15 minutes in 0.2×SSC buffer at 65° C. (See Sambrook et al., 1989) for a description of SSC buffer). Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4-6×SSC at 40° C. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to clone homologous nucleotide sequences that are substantially identical to reference nucleotide sequences of the present invention: a probe nucleotide sequence preferably hybridizes to a target nucleotide sequence in 7% sodium dodecyl sulfate (SDS), 0.5 M $NaPO_4$, 1 mM EDTA at 50° C. followed by washing in 2×SSC, 0.1% SDS at 50° C.; more preferably, a probe and target sequence hybridize in 7% sodium dodecyl sulfate (SDS), 0.5 M $NaPO_4$, 1 mM EDTA at 50° C. followed by washing in 1×SSC, 0.1% SDS at 50° C.; more preferably, a probe and target sequence hybridize in 7% sodium dodecyl sulfate (SDS), 0.5 M $NaPO_4$, 1 mM EDTA at 50° C. followed by washing in 0.5×SSC, 0.1% SDS at 50° C.; more preferably, a probe and target sequence hybridize in 7% sodium dodecyl sulfate (SDS), 0.5 M $NaPO_4$, 1 mM EDTA at 50° C. followed by washing in 0.1×SSC, 0.1% SDS at 50° C.; more preferably, a probe and target sequence hybridize in 7% sodium dodecyl sulfate (SDS), 0.5 M $NaPO_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, are biologically functional equivalents; or are immunologically cross-reactive. These terms are defined further under the heading SCN/SDS Resistance Polypeptides herein below. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues (Batzer et al. (1991) *Nucleic Acid Res.* 19:5081; Ohtsuka et al. (1985) *J Biol Chem* 260:2605-2608; Rossolini et al. (1994) *Mol Cell Probes* 8:91-98).

The term "plant-expressible variant" means a substantially similar sequence that has been modified to comprise a coding sequence (nucleotide sequence) can be efficiently expressed by plant cells, tissue and whole plants. The art understands that a plant-expressible coding sequence has a GC composition consistent with good gene expression in plant cells, a sufficiently low CpG content so that expression of that coding sequence is not restricted by plant cells, and codon usage which is consistent with that of plant genes. Where it is desired that the properties of the plant-expressible SCN/SDS resistance gene are identical to those of the naturally occurring SCN/SDS resistance gene, the plant-expressible homolog will have an identical coding sequence or a substantially identical coding sequence.

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising about 8 or more deoxyribonucleotides or ribonucleotides, preferably 10-20 nucleotides, and more preferably 20-30 nucleotides of a selected nucleic acid molecule. The primers of the present invention encompass oligonucleotides of sufficient length and appropriate sequence so as to provide initiation of polymerization on a nucleic acid molecule of the present invention.

The term "elongated sequence" refers to an addition of nucleotides (or other analogous molecules) incorporated into the nucleic acid. For example, a polymerase (e.g., a DNA polymerase), e.g., a polymerase that adds sequences at the 3' terminus of the nucleic acid molecule can be employed to prepare an elongated sequence. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The term "complementary sequence", as used herein, indicates two nucleotide sequences that comprise anti-parallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable, of hybridizing to the nucleic acid segment in question under relatively stringent conditions such as those described herein. A particular example of a complementary nucleic acid segment is an antisense oligonucleotide.

The present invention further includes vectors comprising the disclosed SCN/SDS resistance gene sequences, including plasmids, cosmids, and viral vectors. The term "vector", as used herein refers to a DNA molecule having sequences that enable its replication in a compatible host cell. A vector also includes nucleotide sequences to permit ligation of nucleotide sequences within the vector, wherein such nucleotide sequences are also replicated in a compatible host cell. A vector can also mediate recombinant production of an SCN/SDS resistance gene polypeptide, as described further herein below.

Nucleic acids of the present invention can be cloned, synthesized, recombinantly altered, mutagenized, or combinations thereof. Standard recombinant DNA and molecular cloning techniques used to isolate nucleic acids are well known in the art. Exemplary, non-limiting methods are described by Sambrook et al., eds., 1989; by Silhavy et al., 1984; by Ausubel et al., 1992; and by Glover, ed. (1985) *DNA Cloning: A Practical Approach*, MRL Press, Ltd., Oxford, United Kingdom. Site-specific mutagenesis to create base pair changes, deletions, or small insertions are also well known in the art as exemplified by publications, see, e.g., Adelman et al., (1983) *DNA* 2:183; Sambrook et al. (1989).

Nucleotide sequences of the present invention can detected, subcloned, sequenced, and further evaluated by any measure well known in the art using any method usually applied to the detection of a specific DNA sequence including but not limited to dideoxy sequencing, PCR, oligomer restriction (Saiki et al., *Bio/Technology* 3:1008-1012 (1985), allele-specific oligonucleotide (ASO) probe analysis (Conner et al. (1983) *Proc Natl Acad Sci USA* 80:278), and oligonucleotide ligation assays (OLAs) (Landgren et. al. (1988) *Science* 241: 1007). Molecular techniques for DNA analysis have been reviewed (Landgren et. al. (1988) *Science* 242:229-237).

| Table of Functionally Equivalent Codons | | | |
|---|---|---|---|
| Amino Acids | | | Codons |
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

III.B. Genetic Markers

The term "genetic marker", as used herein generally refers to a genetic locus, a phenotype conferred by locus, or a nucleotide sequence residing at a locus, wherein the locus is genetically linked to a trait of interest. The term "genetically linked" as used herein refers to two or more loci that are predictably inherited together during random crossing or intercrossing. Quantitative linkage analysis is further described in the section Genetic Mapping herein above. Preferably, genetically linked loci are less than about 10 cM apart, more preferably less than about 5 cM apart, and even more preferably less than about 1 cM apart. Optimally, the genetic marker and the gene conferring a trait of interest comprise the same or overlapping nucleotide sequence.

An embodiment of the present invention comprises genetic markers associated with SCN resistance and SDS resistance that are isolatable from soybeans, and which are free from total genomic DNA. Disclosed herein are sequences of AFLP markers mapped in soybean to the chromosomal segments carrying rhg1 and SDS loci on molecular linkage group G and the Rhg4 locus on molecular linkage group A2. Representative markers for SCN/SDS resistance are set forth as SEQ ID NOs:1, 3, 5, 7, 9, and 11. Representative corresponding markers for SCN/SDS susceptibility are set forth as SEQ ID NOs: 2, 4, 6, 8, 10, and 12.

AFLP bands were obtained as described in Example 3. From each AFLP band, 4-30 clones were sequenced (mean 15.6) depending on the sequence complexity of the originating band. The sequence analysis showed that each AFLP band can be composed of a number of different DNA sequences from fragments of identical size. A mean of 6 sequences per band with a range of 1-15 sequences per band was detected. From a single AFLP band only one sequence corresponded with the original AFLP marker. The other sequences were bands that shared not only the same size within 1-2 bp but also the same selective bases at the EcoRI and MseI sites (100%). Further, some of the cloned sequences from within a band shared between 6 to 15 bp in common to each side (EcoRI and MseI) of the original AFLP polymorphism (about 30% of bands).

To identify polymorphisms within the AFLP, the AFLP sequence was used to design primers to screen the Forrest BamHI BAC library by PCR. For example, $E_{ATG}M_{CGA}87$ was a dominant AFLP band in coupling phase with the rhg1 locus, and screening with a $E_{ATG}M_{CGA}87$ AFLP band primer yielded a single clone. Two internal primers were designed from the $E_{ATG}M_{CGA}87$ resistant allele and DNA from the corresponding BAC was used as template to extend the sequence from the AFLP marker both up and down stream by sequencing. The sequence showed a single 5 bp indel underlay the polymorphic band and no SNPs were present. As used herein, an "indel" refers to a nucleotide insertion or a deletion (FIG. 1B). No additional polymorphisms were detected in about 1,250 bp of flanking sequence.

Sequence comparison of both, resistant and the susceptible alleles of the co-dominant AFLP marker $E_{CTA}M_{AGG}113$ found polymorphisms including both indels and SNPs. There were 4 SNPs within 113 bp and 1 indel (21 bp) (FIG. 1A). Primer sets were designed around the indel site and used to map the genetic position. The genetic position of the identified indel mapped to the region of the original AFLP.

Sequence comparison of resistant and the susceptible alleles of the dominant AFLP marker $E_{CCC}M_{ATG}161$ found SNP polymorphism. There were 2 SNPs within 116 bp (FIG. 1A). Primer sets were designed around the SNP site and used to map the genetic position. The genetic position of the identified indel mapped to the region of the original AFLP.

Sequence comparison of both resistant and susceptible alleles of the dominant AFLP marker $E_{CCA}M_{AGC}114$ found SNP polymorphism adjacent to the EcoRI site. There was 1 SNP within 114 bp (FIG. 1A).

Sequence comparison of resistant and susceptible alleles of the co-dominant AFLP marker $E_{CCG}M_{AAC}405$ found polymorphisms including both indels and SNPs. There were 2 indels (12 bp and 4 bp) and 4 SNPs within 405 bp (FIG. 1A). The 4 bp indel was two AG repeats in an $[AG]_5$ complex micro-satellite sequence. Primer sets were designed around both indel sites and used to map the genetic position. In both cases, the genetic position of the identified indel mapped to the region of the original AFLP.

For the AFLP marker $E_{CGG}M_{AGA}116$, the polymorphisms were found adjacent to both the EcoRI and MseI restriction sites (FIG. 1A). The six selective nucleotide step was replaced by $M_{AGAGACT}$ and $E_C$. Using this primer set the detection of the polymorphism on sequencing gels as well as the mapping of this sequence to the same location as the original AFLP was successful (FIG. 2B). There was 1 indel (2 bp) and 1 SNPs within 116 bp (FIG. 1A). The 2 bp indel was the $[A]_2$ extension of an $[A]_8$ repeat. Primer sets were designed around the indel and SNP sites and used to map their genetic positions. In both cases, the genetic position of the identified polymorphism was identical to the region of the original AFLP.

Comparison of both alleles of the AFLP marker $E_{CCG}M_{AAC}405$ provided four SNPs, two indels and one SSR. The insertion of $[AG]_2$ in the $[AG]_8$ repeat of the resistance allele created a microsatellite polymorphism that was designated SIUC-SAG405 by the present co-inventors. The difference of 4 by between the two alleles at position 224 by to 228 by was enough to discriminate between the resistant and susceptible allele after electrophoresis through a 4% (v/w) Metaphor7 agarose gel. The 12 by indel at 42 by to 54 by was used to design a sequence specific PCR marker (FIG. 2D), and to develop a TAQMANT™ assay for the Rhg4 locus. SNPs were found within the $E_{CCG}M_{AAC}405$. The transversions of T at position 327 in the resistant allele to C at position 337 in the susceptible allele; and A at position 358 by in the resistance allele to C at position 366 by in the susceptible allele can also be used for high-throughput screening SNPs based assay.

An indel of 21 bp was responsible for the polymorphism at the $E_{CTA}M_{AGG}113$ AFLP locus between Essex and Forrest. PCR based markers were designed to flank the 21 bp indel and shown to be polymorphic, the new marker was named CTA (FIG. 2C).

In the $E_{ATG}M_{CGA}87$ marker the insertion of CTTAT to form a tandem repeat in the Forrest allele at position 20 by to 25 by created a 5 by polymorphism that was suitable for marker development. PCR primers were designed to develop a sequence specific PCR assay (FIG. 2A), the new marker was named ATG4. The same indel was used to develop a TAQ-MAN™ probe named TMA5 to discriminate between the two alleles.

The genetic markers of the present invention can be used to reliably select SCN/SDS resistance, as described herein.

III.C. SCN/SDS Resistance Genes

The term "gene" refers broadly to any segment of DNA associated with a biological function. A gene encompasses sequences including but not limited to a coding sequence, a promoter region, a cis-regulatory sequence, a non-expressed DNA segment, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "gene" thus includes an isolated soybean rhg1 and SDS resistance gene as disclosed herein (FIG. 3). The gene is capable of conveying *Heterodera glycines*-infestation resistance or *Fusarium solani*-infection resistance to a non-resistant soybean germplasm, the gene located within a quantitative trait locus mapping to linkage group G and mapped by genetic markers of SEQ ID NOs:1-6, said gene located along said quantitative trait locus between said markers. Positional cloning methods were used to isolate genomic sequences in the chromosomal regions of Forrest that confers SCN/SDS resistance, as further described in Example 4. Specifically, rhg1 sequences were derived from BAC clones 21D9 and 73P6 of the Forrest BamHI or HindIII BAC libraries (Meksem et al., 2000). Preferably, the gene comprises the nucleotide sequence set forth as SEQ ID:13 (FIG. 7A-B). BLASTP analysis of the conceptual translation of the rhg1 gene (FIG.

7C), set forth as SEQ ID:14 shows high homology to the T46070 GenBank entry described as hypothetical protein T18N14.120 from *Arabidopsis thaliana* (FIG. 7E-F), high homology to the rice Xa21 disease resistance gene encoding a leucine-rich repeat protein, and high homology to the tomato CF-2 gene for resistance to *Cladosporium fulvus* (FIG. 7D).

The rhg1 sequences disclosed herein can also be used to isolate rhg1 cDNAs according to methods well-known in the art. A representative rhg1 partial cDNA is set forth as SEQ ID NO:122. This segment of the rhg1 gene shows homology to the leucine-rich regions of the *Arabidopsis* hypothetical protein T18N14.120 (Gen Bank T46070) and tomato CF-2 resistance genes.

For example, the term "gene" also includes an isolated soybean Rhg4 gene. The gene is capable of conveying *Heterodera glycines*-infestation resistance to a non-resistant soybean germplasm, said gene located within a quantitative trait locus mapping to linkage group A2 and mapped by the AFLP markers of SEQ ID NOs:6-12, said gene located along said quantitative trait locus between said markers. Preferably, the gene comprises a nucleotide sequence set forth as any one of SEQ ID NOs:16-19.

Genes underlying quantitative traits, or genes with related function, such as disease resistance, are often organized in clusters within the genome (e.g., Staskawicz (1995) *Science* 268:661-667). In the case of SCN/SDS resistance, previous studies by the co-inventors of the present invention have suggested that the resistance trait in Forrest may be caused by four genes in a cluster with two pairs in close linkage or by a two-gene cluster with each gene displaying pleitropy (Meksem et al., 1999). Thus, genomic DNA isolated and disclosed herein comprise multiple resistance gene sequences. Additional sequences derived from the SCN/SDS resistance locus are set forth as SEQ ID NOs:20-66. BLASTX analysis of these sequences reveals further homology to known proteins in other organisms, supporting that they comprise new partial gene sequences (Table 1). Of particular interest, BLASTX analysis of the sequences set forth as SEQ ID NOs:67-114 reveals that several of the disclosed sequences have high homology to the T46070 GenBank entry described as hypothetical protein T18N14.120 from *Arabidopsis thaliana*, high homology to the tomato CF-2 disease resistance genes encoding leucine-rich repeat proteins, and to the tomato CF-9 gene for resistance to *Cladosporium fulvus* (Table 1).

The present invention also pertains to resistance genes related to rhg1 and Rhg4. Partial cDNAs of additional putative SCN/SDS resistance genes, set forth as SEQ ID NOs:67-114, were identified based on hybridization to rhg1 and Rhg4 sequences, as further described in Example 5. BLASTX analysis of these sequences reveals further homology to known proteins in other organisms, supporting that they comprise new partial gene sequences (Table 2). Of particular interest, BLASTX analysis of the sequences set forth as SEQ ID NOs:67-114 reveals that several of the disclosed sequences have high homology to the T46070 GenBank entry described as hypothetical protein T18N14.120 from *Arabidopsis thaliana*, high homology to the tomato CF-2 disease resistance genes encoding leucine-rich repeat proteins, and to the tomato CF-9 gene for resistance to *Cladosporium fulvus* (Table 2). Based on their hybridization to rhg1 and Rhg4 sequences, genes comprising any of SEQ ID NOs:67-114 may also confer resistance to race 3 *Heterodera glycines*. It will be apparent to one having ordinary skill in the art that the disclosed sequences, or portion thereof, can be used to identify, confirm and/or screen for SDS, SCN and/or other resistance or for loci that confer SDS, SCN and/or other resistance.

TABLE 1

| SEQ ID NO. | inventor's reference | best BLAST hit (ACCESSION) | Score (bits) | E value | Identities | Positives |
| --- | --- | --- | --- | --- | --- | --- |
| 20 | III-00_F2-3RCF1900-2450 | T47727 | 230 | 9e-60 | 114/170 (67%) | 134/170 (78%) |
| 21 | III-01_21d9A1, 1A1 | no significant similarity | | | | |
| 22 | III-01_21d9A2, 11F11Rlaccase | AC007063 | 97 | 1e-19 | 62/166 (37%) | 92/166 (55%) |
| 23 | III-01_21d9A2, 4A4Mic | no significant similarity | | | | |
| 24 | III-01_CMG, smalF1-1F | T46070 | 67 | 4e-13 | 49/147 (33%) | 62/147 (41%) |
| 25 | III-02_21d9A2, 12A12FNaH+hypoth | T00576 | 67 | 2e-10 | 57/188 (30%) | 87/188 (45%) |
| 26 | III-02_F3-1RCF2000-2500 | T46070 | 170 | 7e-42 | 79/105 (75%) | 93/105 (88%) |
| 27 | III-03_21d9A1, 1E1Flaccase | AC007020 | 61 | 1e-08 | 37/65 (56%) | 43/65 (65%) |
| 28 | III-03_21d9A2, 12A12RNaH+hypothet | AC007063 | 116 | 2e-25 | 61/165 (36%) | 95/165 (56%) |
| 29 | III-03_21d9A2, 4B4ESTM | no significant similarity | | | | |
| 30 | III-03_21d9A2, 8F8CF1a | T47727 | 187 | 53-48 | 95/142 (66%) | 106/142 (73%) |
| 31 | III-03_21d9A2, 8F8CFHomol | T47727 | 177 | 5e-45 | 90/132 (68%) | 100/132 (75%) |
| 32 | III-03_CMG, smalF1-3FCF300-1100 | T46070 | 107 | 4e-27 | 67/189 (35%) | 89/189 (46%) |
| 33 | III-03_F3-2R1800-Cterm | T47727 | 201 | 1e-64 | 97/129 (75%) | 113/129 (87%) |
| 34 | III-04_21d9A1, 1E1R | no significant similarity | | | | |
| 35 | III-04_21d9A2, 1B1 | no significant similarity | | | | |
| 36 | III-04_21d9A2, 6D6mic | no significant similarity | | | | |
| 37 | III-05_21d9A1, 1C1GmxLaccase | AB010692 | 153 | 2e-36 | 80/124 (64%) | 90/124 (72%) |
| 38 | III-05_21d9A2, 4C4CFHomol | T46070 | 125 | 6e-28 | 65/106 (61%) | 72/106 (67%) |
| 39 | III-06_21d9A2, 11A11laccasegene | AC007020 | 67 | 3e-12 | 30/49 (61%) | 35/49 (71%) |
| 40 | III-07_21d9A1, 2A2F | no significant similarity | | | | |
| 41 | III-08_21d9A1, 2A2R | no significant similarity | | | | |
| 42 | III-08_21d9A2, 6F6 | no significant similarity | | | | |
| 43 | III-09_21d9A1, 1E1 | no significant similarity | | | | |
| 44 | III-09_21d9A1, 2D2FNaH+hypothe | AC007063 | 84 | 93-17 | 44/127 (34%) | 74/127 (57%) |
| 45 | III-09_21d9A2, 4E4Laccase | AC007020 | 90 | 1e-32 | 43/53 (81%) | 46/53 (86%) |
| 46 | III-09_21d9A2, 9A9 | no significant similarity | | | | |
| 47 | III-10_21d9A2, 11C11 | T47325 | 53 | 3e-06 | 45/132 (34%) | 65/132 (49%) |
| 48 | III-10_21d9A2, 11C11hypothetical | T47325 | 53 | 3e-06 | 45/132 (34%) | 65/132 (49%) |
| 49 | III-11_21d9A1, 1F1SatAT | no significant similarity | | | | |
| 50 | III-11_21d9A2, 4A4F | no significant similarity | | | | |
| 51 | III-11_21d9A2, 4F4SatTA | no significant similarity | | | | |
| 52 | III-12_21d9A2, 1F1NaHexchangine | AC007063 | 126 | 3e-28 | 72/181 (39%) | 108/181 (58%) |

TABLE 1-continued

| SEQ ID NO. | inventor's reference | best BLAST hit (ACCESSION) | Score (bits) | E value | Identities | Positives |
|---|---|---|---|---|---|---|
| 53 | III-12__21d9A2, 4A4RSatTAGA | no significant similarity | | | | |
| 54 | III-13__21d9A1, 1G1NaHexchanHypothe | T00576 | 50 | 2e−05 | 31/83 (37%) | 44/83 (52%) |
| 55 | III-13__21d9A1, 8D8CF500-1000 | T46070 | 84 | 4e−24 | 48/127 (37%) | 66/127 (51%) |
| 56 | III-13__21d9A2, 4B4FSatGAAAA | no significant similarity | | | | |
| 57 | III-14__21d9A2, 11E11GmxEST | no significant similarity | | | | |
| 58 | III-14__21d9A2, 1G1 | no significant similarity | | | | |
| 59 | III-15__21d9A1, 8E8 | no significant similarity | | | | |
| 60 | III-15__21d9A2, 4C4FCF1600-1000 | T46070 | 158 | 6e−38 | 99/215 (46%) | 113/215 (52%) |
| 61 | III-15__21d9A2, 9D9NaHlonexch | AC007063 | 64 | 1e−09 | 38/118 (32%) | 59/118 (49%) |
| 62 | III-16__21d9A1, 11D11laccase | CAA74104 | 82 | 4e−17 | 35/49 (71%) | 43/49 (87%) |
| 63 | III-16__21d9A2, 11F11MicSatTA | no significant similarity | | | | |
| 64 | III-16__21d9A2, 4C4R300-1000 | T46070 | 110 | 3e−32 | 67/178 (37%) | 86/178 (47%) |
| 65 | III-17__21d9A1, 2A2SatGA | no significant similarity | | | | |
| 66 | III-17__21d9A1, 2A2SatTAA | no significant similarity | | | | |
| 73 | II-01F2-4RCf1900-2400 | T46070 | 187 | 6e−47 | 99/183 (54%) | 123/183 (67%) |

TABLE 2

| SEQ ID NO. | inventor's reference | best BLAST hit (ACCESSION) | Score (bits) | E value | Identities | Positives |
|---|---|---|---|---|---|---|
| 67 | 3A Cf2 homologues to the +2ORF clone ID: 07d9 | T47727 | 189 | 4e−47 | 103/215 (47%) | 127/215 (58%) |
| 68 | 3B Cf2 homologues to the −2ORF clone ID: 05d7 | T46070 | 148 | 8e−35 | 76/157 (48%) | 98/157 (62%) |
| 69 | 3C Cf2 homologues to the +3 ORF clone ID: 17P9 | T47727 | 200 | 2e−50 | 100/136 (73%) | 113/136 (82%) |
| 70 | 3D Cf2 homologues to the −3ORF clone ID: 06d8 | T46070 | 163 | 2e−39 | 86/179 (48%) | 110/179 (61%) |
| 71 | II-00__F2-3RCF1900-2450 | T47727 | 230 | 9e−60 | 114/170 (67%) | 134/170 (78%) |
| 72 | II-01CMGsmalF1-1F300-1000 | T46070 | 76 | 4e−13 | 49/147 (33%) | 62/147 (41%) |
| 73 | II-01F2-4RCf1900-2400 | T46070 | 187 | 6e−47 | 99/183 (54%) | 123/183 (67%) |
| 74 | II-02F3-1RCF2000-2500 | T46070 | 170 | 7e−42 | 79/105 (75%) | 93/105 (88%) |
| 75 | II-03.21dA2, 8F8CF1-500 | T47727 | 187 | 5e−48 | 95/142 (66%) | 106/142 (73%) |
| 76 | II-03CMG, smalF1-3FCF300-1100 | T46070 | 107 | 4e−27 | 67/189 (35%) | 89/189 (46%) |
| 77 | II-03F3-2R1800-Cterm | T47727 | 201 | 1e−64 | 97/129 (75%) | 113/129 (87%) |
| 78 | II-04.21dA1, 1E1R | no significant similarity | | | | |
| 79 | II-05.21dA2, 4C4CFhomol | T46070 | 125 | 6e−28 | 65/106 (61%) | 72/106 (67%) |
| 80 | II-12CFLNO1F-CFNOIF | T46070 | 135 | 2e−33 | 74/165 (44%) | 97/165 (57%) |
| 81 | II-12CFLNO1F-CFLNOIR | T46070 | 273 | 2e−72 | 133/183 (72%) | 156/183 (84%) |
| 82 | II-12CFLNO1F-CFLNNIF | T46070 | 184 | 73-46 | 91/128 (71%) | 100/128 (78%) |
| 83 | II-12CFLNO1F-CFLNN2F | T46070 | 109 | 3e−24 | 69/189 (36%) | 89/189 (46%) |
| 84 | II-13.21dA1, 8D8CF500-1000 | T46070 | 84 | 4e−24 | 48/127 (37%) | 66/127 (51%) |
| 85 | II-15.21dA2, 4C4FCF1600-1000 | T46070 | 158 | 6e−38 | 99/215 (46%) | 113/215 (52%) |
| 86 | II-29.21dA2, 8F8FCF500upstream | T47727 | 102 | 2e−39 | 56/105 (53%) | 67/105 (63%) |
| 87 | II-30.21d9A2, 12E12ESTMedicago | T47731 | 238 | 6e−62 | 119/163 (73%) | 132/163 (80%) |
| 88 | II-30.21d9A2, 8F8RCFpromoter | no significant similarity | | | | |
| 89 | II-30.E2, TetRP1downstreamtoRhg1 | S05434 | 35 | 1.0 | 30/109 (27%) | 49/109 (44%) |
| 90 | II-32.E3, TetRP1CF1115-1249 | no significant similarity | | | | |
| 91 | II-Cf homol-01CMGsmalF1-2F | T46070 | 76 | 4e−13 | 49/147 (33%) | 62/147 (41%) |
| 92 | II-Cf homol-CMGsmalF1-2F | T46070 | 125 | 8e−32 | 74/188 (39%) | 95/188 (50%) |
| 93 | II-Cf homol-03CMGsmalF1-3 | T46070 | 105 | 1e−26 | 66/188 (35%) | 88/188 (46%) |
| 94 | II-Cf homol-06CMGsmalF2-2F | T46070 | 123 | 2e−27 | 80/224 (35%) | 105/224 (46%) |
| 95 | II-Cf homol-07CMGsmalF2-3F | T46070 | 123 | 2e−27 | 80/224 (35%) | 105/224 (46%) |
| 96 | II-Cf homol-08CMGsmalF2-4F03 | T46070 | 118 | 6e−29 | 71/183 (38%) | 90/183 (48%) |
| 97 | II-Cf homol-10CMGsmalF3-2F | T46070 | 184 | 7e−46 | 91/128 (71%) | 100/128 (78%) |
| 98 | II-Cf homol-09CMGsmalF3-1F | T46070 | 184 | 6e−46 | 91/128 (71%) | 100/128 (78%) |
| 99 | II-Cf homol-smalF3-3F | T46070 | 265 | 2e−70 | 128/174 (73%) | 151/174 (86%) |
| 100 | II-Cf homol-12CMGsmalF3-4F | T46070 | 184 | 7e−46 | 89/107 (83%) | 97/107 (90%) |
| 101 | II-Cf homol-13CMGsmalF1-1R | T46070 | 279 | 3e−74 | 136/191 (71%) | 159/191 (83%) |
| 102 | II-Cf homol-14CMGsmalF1-2R | T46070 | 261 | 3e−69 | 127/176 (72%) | 148/176 (83%) |
| 103 | II-Cf homol-15CMGsmalF1-3R | T47727 | 246 | 1e−64 | 120/162 (74%) | 140/162 (86%) |
| 104 | II-Cf homol-16CMGsmalF1-4R | T46070 | 263 | 1e−70 | 128/176 (72%) | 149/176 (83%) |
| 105 | II-Cf homol-17CMGsmalF2-1R | T46070 | 268 | 5e−71 | 131/183 (71%) | 155/183 (84%) |
| 106 | II-Cf homol-18CMGsmalF2-2R | T46070 | 244 | 4e−65 | 118/159 (74%) | 137/159 (85%) |
| 107 | II-Cf homol-05F3-4R | T46070 | 187 | 6e−47 | 90/136 (66%) | 111/136 (81%) |
| 108 | II-Cf homol-00F2-3R | T46070 | 224 | 3e−58 | 108/148 (72%) | 127/148 (84%) |
| 109 | II-Cf homol-01F2-4R | T46070 | 187 | 6e−47 | 99/183 (54%) | 123/183 (67%) |
| 110 | II-Cf homol-02F3-1R | T46070 | 170 | 7e−42 | 79/105 (75%) | 93/105 (88%) |
| 111 | II-Cf homol-03F3-2R | T47727 | 202 | 9e−65 | 97/133 (72%) | 11/133 (84%) |
| 114 | II-Cf homol-04F3-3R | T46070 | 128 | 1e−30 | 65/108 (60%) | 72/108 (66%) |
| 114 | II-Cf homol-05CMGsmalF2-F | T46070 | 184 | 6e−46 | 91/128 (71%) | 100/128 (78%) |
| 114 | II-downstream to Rhg1 | no significant similarity | | | | |

III.D. SCN/SDS Resistance Gene Promoters

The term "promoter region" defines a nucleotide sequence within a gene that is positioned 5' to a coding sequence of a same gene and functions to direct transcription of the coding sequence. The promoter region includes a transcriptional start site and at least one cis-regulatory element. The present invention encompasses nucleic acid sequences that comprise a promoter region of an SCN/SDS resistance gene, or functional portion thereof.

The terms "cis-acting regulatory sequence" or "cis-regulatory motif" or "response element", as used herein, each refer to a nucleotide sequence that enables responsiveness to a regulatory transcription factor. Responsiveness can encompass a decrease or an increase in transcriptional output and is mediated by binding of the transcription factor to the DNA molecule comprising the response element.

The term "transcription factor" generally refers to a protein that modulates gene expression by interaction with the cis-regulatory element and cellular components for transcription, including RNA Polymerase, Transcription Associated Factors (TAFs), chromatin-remodeling proteins, and any other relevant protein that impacts gene transcription.

The term "gene expression" generally refers to the cellular processes by which a biologically active polypeptide is produced from a DNA sequence.

A "functional portion" of a promoter gene fragment is a nucleotide sequence within a promoter region that is required for normal gene transcription. To determine nucleotide sequences that are functional, the expression of a reporter gene is assayed when variably placed under the direction of a promoter region fragment.

Promoter region fragments can be conveniently made by enzymatic digestion of a larger fragment using restriction endonucleases or DNAse I. Preferably, a functional promoter region fragment comprises about 5,000 nucleotides, more preferably 2,000 nucleotides, more preferably about 1,000 nucleotides, more preferably a functional promoter region fragment comprises about 500 nucleotides, even more preferably a functional promoter region fragment comprises about 100 nucleotides, and even more preferably a functional promoter region fragment comprises about 20 nucleotides.

Within a candidate promoter region or response element, the presence of regulatory proteins bound to a nucleic acid sequence can be detected using a variety of methods well known to those skilled in the art (Ausubel et al., 1992). Briefly, in vivo footprinting assays demonstrate protection of DNA sequences from chemical and enzymatic modification within living or permeabilized cells. Similarly, in vitro footprinting assays show protection of DNA sequences from chemical or enzymatic modification using protein extracts. Nitrocellulose filter-binding assays and gel electrophoresis mobility shift assays (EMSAs) track the presence of radiolabeled regulatory DNA elements based on provision of candidate transcription factors.

The terms "reporter gene" or "marker gene" or "selectable marker" each refer to a heterologous gene encoding a product that is readily observed and/or quantitated. A reporter gene is heterologous in that it originates from a source foreign to an intended host cell or, if from the same source, is modified from its original form. Non-limiting examples of detectable reporter genes that can be operably linked to a transcriptional regulatory region can be found in brown and PCT International Publication No. WO 97/47763. Preferred reporter genes for transcriptional analyses include the lacZ gene (See, e.g., Rose & Botstein (1983) *Meth Enzymol* 101:167-180), Green Fluorescent Protein (GFP) (Cubitt et al. (1995) *Trends Biochem Sci* 20:448-455), luciferase, or chloramphenicol acetyl transferase (CAT). Preferred reporter genes for stable transformation include but are not limited to antibiotic resistance genes. Any suitable reporter and detection method can be used, and it will be appreciated by one of skill in the art that no particular choice is essential to or a limitation of the present invention.

An amount of reporter gene can be assayed by any method for qualitatively or preferably, quantitatively determining presence or activity of the reporter gene product. The amount of reporter gene expression directed by each test promoter region fragment is compared to an amount of reporter gene expression to a control construct comprising the reporter gene in the absence of a promoter region fragment. A promoter region fragment is identified as having promoter activity when there is significant increase in an amount of reporter gene expression in a test construct as compared to a control construct. The term "significant increase", as used herein, refers to an quantified change in a measurable quality that is larger than the margin of error inherent in the measurement technique, preferably an increase by about 2-fold or greater relative to a control measurement, more preferably an increase by about 5-fold or greater, and most preferably an increase by about 10-fold or greater.

A representative SCN/SDS resistance gene promoter, the rhg1 promoter, is set forth as SEQ ID NO:15. The rhg1 promoter is useful for directing gene expression of heterologous sequences in vivo or in assays to identify modulators of rhg1 expression, described further herein below.

The present invention further provides an isolated SCN/SDS resistance gene promoter region, or functional portion thereof, comprising an about 90 kb fragment of soybean genomic clone 73P6 between BamHI restriction sites and 21d9 between HinDIII restriction site. The genomic clone is available from the Forrest BAC library described in Meksem et al (2000), *Theor Appl Genet*. 101 5/6: 747-755, available through Southern Illinois University-Carbondale (Carbondale, Ill.), Texas A&M University BAC center (College Station, Tex.), and Research Genetics (Huntsville, Ala.). An isolated SCN/SDS resistance gene promoter region, or functional portion thereof, comprising an about 4.5 kb fragment of soybean genomic clone 21d9A2 8F8 between EcoRI restriction sites is also disclosed.

III.E. Chimeric Genes

The present invention also encompasses chimeric genes comprising the disclosed SCN/SDS resistance gene sequences. The term "chimeric gene", as used herein, refers to an SCN/SDS resistance gene promoter region operably linked to an open reading frame, wherein the nucleotide sequence created is not naturally occurring. In this regard, the open reading frame is also described as a "heterologous sequence". The term "chimeric gene" also encompasses a promoter region operably linked to an SCN/SDS resistance gene coding sequence, a nucleotide sequence producing an antisense RNA molecule, a RNA molecule having tertiary structure, such as a hairpin structure, or a double-stranded RNA molecule.

The term "operably linked", as used herein, refers to a promoter region that is connected to a nucleotide sequence in such a way that the transcription of that nucleotide sequence is controlled and regulated by that promoter region. Techniques for operatively linking a promoter region to a nucleotide sequence are well known in the art.

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native cis-regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

IV. Polypeptide Sequences of SCN/SDS Resistance Proteins

The polypeptides provided by the present invention include the isolated polypeptide of SEQ ID NO:14, fusion proteins comprising SCN/SDS resistance gene amino acid sequences, biologically functional analogs, and polypeptides that cross-react with an antibody that specifically recognizes an SCN/SDS resistance gene polypeptide.

The term "isolated", as used in the context of a polypeptide, indicates that the polypeptide exists apart from its native environment and is not a product of nature. An isolated polypeptide can exist in a purified form or can exist in a non-native environment such as, for example, in a transgenic host cell.

The term "purified", when applied to a polypeptide, denotes that the polypeptide is essentially free of other cellular components with which it is associated in the natural state. Preferably, a polypeptide is a homogeneous solid or aqueous solution. Purity and homogeneity are typically determined using analytical chemistry techniques such as polyacrylamide gel electrophoresis or high performance liquid chromatography. A polypeptide that is the predominant species present in a preparation is substantially purified. The term "purified" denotes that a polypeptide gives rise to essentially one band in an electrophoretic gel. Particularly, it means that the polypeptide is at least about 50% pure, more preferably at least about 85% pure, and most preferably at least about 99% pure.

The term "substantially identical" in the context of two or more polypeptides sequences is measured by (a) polypeptide sequences having about 35%, or 45%, or preferably from 45-55%, or more preferably 55-65%, or most preferably 65% or greater amino acids that are identical or functionally equivalent. Percent "identity" and methods for determining identity are defined herein under the heading Nucleotide and Amino Acid Sequence Comparisons.

Substantially identical polypeptides also encompass two or more polypeptides sharing a conserved three-dimensional structure. Computational methods can be used to compare structural representations, and structural superpositions can be generated and easily tuned to identify similarities around important active sites or ligand binding sites. See Henikoff et al. (2000) *Electrophoresis* 21(9):1700-1706; Huang et al. (2000) *Pac Symp Biocomput* 230-241; Saqi et al., 1999; and Barton (1998) *Acta Crystallogr D Biol Crystallogr* 54:1139-1146.

The term "functionally equivalent" in the context of amino acid sequences is well known in the art and is based on the relative similarity of the amino acid side-chain substituents. See Henikoff and Henikoff (2000) *Adv Protein Chem* 54:73-97. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further herein below, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al. (1982) *J Mol Biol* 157:105). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

The present invention also encompasses SCN/SDS resistance gene polypeptide fragments or functional portions of an SCN/SDS resistance gene polypeptide. Such functional portion need not comprise all or substantially all of the amino acid sequence of a native resistance gene product. The term "functional" includes any biological activity or feature of SCN/SDS resistance gene, including immunogenicity.

The present invention also includes longer sequences comprising an SCN/SDS resistance gene polypeptide, or portion thereof. For example, one or more amino acids can be added to the N-terminal or C-terminal of an SCN/SDS resistance gene polypeptide. Fusion proteins comprising SCN/SDS resistance gene polypeptide sequences are also provided within the scope of the present invention. Methods of preparing such proteins are known in the art.

The present invention also encompasses functional analogs of an SCN/SDS resistance gene polypeptide. Functional analogs share at least one biological function with an SCN/SDS resistance gene polypeptide. An exemplary function is immunogenicity. In the context of amino acid sequence, biologically functional analogs, as used herein, are peptides in which certain, but not most or all, of the amino acids can be substituted. Functional analogs can be created at the level of the corresponding nucleic acid molecule, altering such sequence to encode desired amino acid changes. In one embodiment, changes can be introduced to improve the antigenicity of the protein. In another embodiment, an SCN/SDS resistance gene polypeptide sequence is varied so as to assess the activity of a mutant SCN/SDS resistance gene polypeptide. In still another embodiment, amino acid changes can be made to improve the stability of the polypeptide.

Isolated polypeptides and recombinantly produced polypeptides can be purified and characterized using a variety of standard techniques that are well known to the skilled artisan. See, e.g. Ausubel et al. (1992); Bodanszky et al., 1976; and Zimmer et al. (1993) *Peptides*, pp. 393B394, ESCOM Science Publishers, B. V.

V. Nucleotide and Amino Acid Sequence Comparisons

The terms "identical" or percent "identity" in the context of two or more nucleotide or polypeptide sequences, refer to two or more sequences or subsequences that are the same or have a specified percentage of amino add residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain at least some of biological activity of the natural gene, gene product, or sequence. Such sequences include. "mutant" sequences, or sequences wherein the biological activity is altered to some degree but retains at least some of the original biological activity. The term "naturally occurring", as used herein, is used to describe a composition that can be found in nature as distinct from being artificially produced by man. For example, a protein or nucleotide sequence present in an organism, which can be isolated from a source in nature and which has not been intentionally modified by man in the laboratory, is naturally occurring.

For sequence comparison, typically one sequence is regarded as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman (1981) *Adv Appl Math* 2:482, by the homology alignment algorithm of Needleman &Wunsch (1970) *J Mol Biol* 48:443, by the search for similarity method of Pearson & Lipman (1988) *Proc Natl Acad Sci USA* 85:2444, by computerized implementations of these algorithms (GAP, BESTFIT, FASTA, and TFASTA in the Wisconsin Genetics Software Package, Genetics Computer Group, Madison, Wis.), or by visual inspection. See generally, Ausubel et al. (1992).

A preferred algorithm for determining percent sequence identity and sequence similarity is the BLAST algorithm, which is described in Altschul et al. (1990) *J Mol Biol* 215: 403-410. Software for performing BLAST analyses is publicly available through the National Center for Biotechnology Information (http://www.ncbi.nim.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff and Henikoff (1989) *Proc Natl Acad Sci USA* 89:10915.

In addition to calculating percent sequence identity, the BLAST algorithm also performs a statistical analysis of the similarity between two sequences. See, e.g., Karlin and Altschul (1993) *Proc Natl Acad Sci USA* 90:5873-5887. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

VI. Method for Detecting a Nucleic Acid Molecule Associated with SCN/SDS Resistance In another aspect of the invention, a method is provided for detecting a nucleic acid molecule that encodes an SCN/SDS resistance polypeptide. Such methods can be used to detect SCN/SDS resistance gene variants and related resistance gene sequences. The disclosed methods facilitate genotyping, cloning, gene mapping, and gene expression studies.

VI.A. Genetic Variants

In one embodiment, genetic assays based on nucleic acid molecules of the present invention can be used to screen for genetic variants by a number of PCR-based techniques, including single-strand conformation polymorphism (SSCP) analysis (Orita et al. (1989) *Proc Natl Acad Sci USA* 86(8): 2766-2770), SSCP/heteroduplex analysis, enzyme mismatch cleavage, direct sequence analysis of amplified exons (Kestila et al. (1998) *Mol Cell* 1(4):575-582; Yuan et al. (1999) *Hum Mutat* 14(5):440-446), allele-specific hybridization (Stoneking et al. (1991) *Am J Hum Genet*. 48(2):370-82), and restriction analysis of amplified genomic DNA containing the specific mutation. Automated methods can also be applied to large-scale characterization of single nucleotide polymorphisms (Brookes (1999) *Gene* 234(2):177-186; Wang et al. (1998) *Science* 280(5366):1077-82). Preferred detection methods are non-electrophoretic, including, for example, the TAQMAN™ allelic discrimination assay, PCR-OLA, molecular beacons, padlock probes, and well fluorescence. See Landegren et al. (1998) *Genome Res* 8:769-776.

In a preferred embodiment, genetic markers for SCN/SDS resistance disclosed herein are used in a PCR-based genotyping assay, preferably, a TAQMAN™ assay as disclosed in Example 6. The TAQMAN™ allelic discrimination assay is based on the 5' nuclease activity of Taq polymerase and detection of a fluorescent reporter during or after PCR reactions (Livak et al. (1995) *PCR Meth and Applic* 4:357-362; Livak et al. (1995) *Nat Genet.* 9:341-342). Each TAQMAN™ probe consists of a 25-35 base oligonucleotide complementary to one of two alleles with a 3' quencher dye attached (6-carboxy-N,N,N'5N' tetrachlorofluorescein; TAMRA). The oligomer complimentary to allele 1 is linked covalently to a 5' reporter dye (6-carboxy-4,7,2',7', tetrachlorofluorescenin; TET) while allele 2 is linked to a dye that fluoresces at a distinct wavelength (6-carboxyfluorescein; FAM). PCR directed by flanking oligomers of 18-20 bases causes degradation during the extension phase of the oligomer that hybridizes most efficiently to the polymorphic site(s) in the sample. Adaptations can make the assay chemistry suitable for multiplexing (Nasarabadi et al. (1999) *Bio Techniques* 27:1116-1117) and miniaturization (Kalinina et al. (1997) *Nucl Acids Res* 25:1999-2004) to reduce cost and increase throughput.

Figure 4:
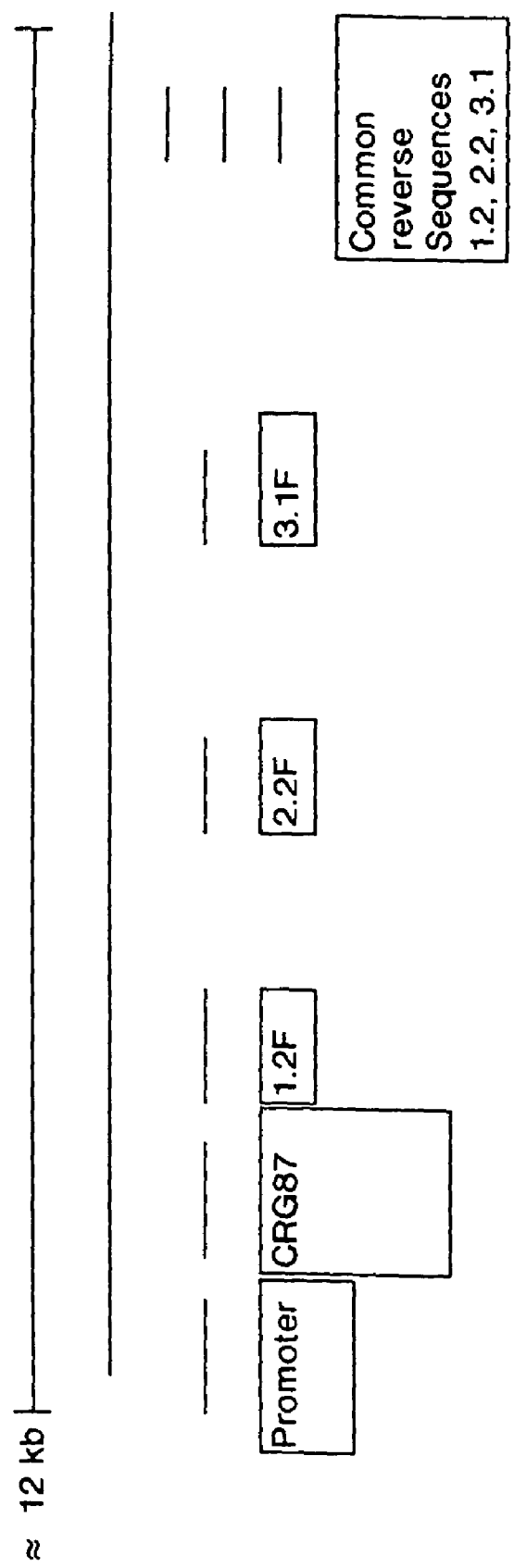

The present invention discloses sequences suitable for use with the TAQMAN™ method for genotyping SCN/SDS resistance, further disclosed in Example 6. As one example, the TAQMAN™ assay was used to distinguish between two insertion polymorphisms in alleles of an AFLP marker that is located about 50 kbp from the Rhg4 gene (FIG. 4). Genomic DNA samples were analyzed using the TAQMAN™ PCR protocol (Livak et al., 1995a, 1995b). Using the raw fluorescence signals of the reporter dyes FAM and TET from the "dye component" field of the sequence detection software, two grouping methods were performed. Each method detected four distinct populations (FIG. 5). The four populations could be assigned according to the FAM:TET ratio based on where the heterogeneous class cut-off was placed.

For the TAQMAN™ selection, two grouping methods were arbitrarily selected to attempt to accurately separate heterogeneous lines from homogeneous lines at each allele. For grouping method 1 (TAQMAN™ 1) a stringent cut-off was used to reduce the number called as potentially heterogeneous. Fluorophore ratios were as follows; no amplification (FAM and TET both less than 6 units); allele 1 homozygous (FAM less than 7, TET greater than 7); allele 2 homozygous (FAM greater than 10, TET less than 5); and heterogeneous for allele 1 and allele 2 (FAM greater than 7, TET 5-8). For TAQMAN™ selection grouping method 2 (TAQMAN™ 2), a lower stringency cut-off value was used to increase the number called as potentially heterogeneous. Ratios were: no amplification (FAM and TET both less than 6 units); allele 1 homozygous (FAM less than 5, TET greater than 7); allele 2 homozygous (FAM greater than 10, TET less than 5); and heterogeneous for allele 1 and allele 2 (FAM greater than 5, TET 5-9).

Based on the FI of the ExF RIL population, the 86 selected individuals were classified into 3 classes: 15 resistant, 60 susceptible and 11 segregating lines. TAQMAN™ analysis of 86 individuals from the RILs by method 1 (high stringency) shows a strong agreement between allele 1 and susceptibility to SCN (56 from the 60 susceptible lines were allele 1 type). However, there was lesser agreement between allele 2 and resistance to SCN (only 15 lines from the 23 lines showing the presence of allele 2 were resistant by phenotype) due to the segregation of rhg1, the second gene necessary for resistance to SCN in Forrest. Of the 11 lines known to be heterogeneous for the resistance to SCN phenotype, five should segregate at Rhg4. TAQMAN™ method 1 identified one among the five classified as heterogenous (the 5 include 4 miss-classified lines, see below). TAQMAN™ method 2 identified all five among the 11 classified as heterogenous, however the 11 include 6 miss-classified lines.

To validate the specificity of TAQMAN™ genotyping, samples of each of the RILs classified by the TAQMAN™ method (FIG. 5) were re-scored by PCR and gel electrophoresis (FIG. 6) according to methods described in Example 7. The classifications produced by the two methods agreed with TAQMAN™ assay 1 most closely but with eight exceptions. The miss-scores were as follows (annotated as RIL#, FI phenotype; allele with TAQMAN™ grouping method 2; allele with TAQMAN™ grouping method 1; allele by gel marker score): 4;S;H;H;S: 21;R;H;H;R: 32;R;H;H;R: 44;S;S;S;H: 51;S;S;S;H: 59;R;H;H;R: 63;S;S;S;R: 78;R;H;H;R.

The majority of disagreements resulted from resistant lines that were scored as heterogeneous by TAQMAN™ but not gel electrophoresis or phenotype (4 of 8) and phenotypically susceptible lines that were scored incorrectly by gel electrophoresis (3 of 8). One genotype (RIL84) was miss-scored relative to phenotype (84SRRR) by all the allele genotyping methods and may represent a recombination event between A2D8 and Rhg4.

The genoytpe and phenotype were generally in close agreement among the eighty six genomic DNA samples analyzed using the TAQMAN™ PCR protocol. The lesser agreement between Allele 2 and resistance to SCN (15 of 23) was shown to be due to the segregation of rhg1, by scoring of the BARC-Satt 309 marker (Meksem et al., 1999). The bias toward a higher frequency of allele 1 is caused by sampling error (Chang et al., 1997). The accuracy of genotyping was high by the TAQMAN™ assay and was better than one pass gel electrophoresis (Prabhu et al., 1999). Even compared to a highly optimized gel electrophoresis assay reported herein the assays were not significantly different in accuracy for detecting the genotypes within the F5 derived RILs in a single pass assay. Exactly 78 of the 86 tested with both, TAQMAN™ and gel electrophoresis results agreed. There were 5 errors with TAQMAN™ (94% accurate) and 3 errors with gel electrophoresis (96% accurate) judged by replicated genotyping (not shown) and the phenotype. Low frequencies of error are important to the accurate selection of resistance (Cregan et al., 1999a; Prabhu et al., 1999) and in the generation of accurate genetic maps (Cregan et al., 1999b).

VI.B. Cloning of SCN/SDS Resistance Genes and Related Genes

The nucleic acids of the present invention can be used to clone genes
and genomic DNA comprising the sequences. Alternatively, the nucleic acids of the present invention can be used to clone genes and genomic DNA of related sequences. For this purpose, representative probes, hybridization conditions, and PCR primers are described in the section entitled Nucleotide Sequences of SCN/SDS Resistance Genes and Associated Markers herein above and in Examples 4 and 5. Preferably, the nucleic acids used for this method comprise sequences set forth as anyone of SEQ ID NOs:13, 15-114, more preferably SEQ ID NOs: 13 and 16-19.

In another embodiment, the present invention provides a method of positional cloning of genes and other sequences located adjacent or near the disclosed sequences within the soybean genome. The method comprises: (a) identifying a first nucleic acid genetically linked to a SCN/SDS resistance locus; and (b) cloning the first nucleic acid. Optionally, the first nucleic acid can comprise the rhg1 and SDS locus or the Rhg4 locus. Preferably, the SCN/SDS resistance locus corresponds to a nucleic acid selected from any one of SEQ ID NOs:13 and 16-19.

Positional cloning first involves creating a physical map of a contig (contiguous overlapping of cloned DNA inserts), in the genomic region encompassing one or more marker loci and the target gene. The target gene is then identified and isolated within one or more clones residing in the contig. The cloned gene can be used according to any suitable method known in the art, including, for example, genetic studies, transformation, and the development of novel phenotypes.

Mapped SCN, SDS, or SCN and sbs markers, especially those most closely linked to SCN/SDS resistance can be used to identify homologous clones from soybean genomic libraries, including, for example, soybean genomic libraries made in bacterial artificial chromosomes (BAC), yeast artificial chromosomes (YAC), or P1 bacteriophage. These types of vectors are preferred for positional cloning because they have the capacity to carry larger DNA inserts than possible with other vector technologies. These larger DNA inserts allow the researcher to move physically farther along the chromosome by identifying overlapping clones. Exemplary libraries available for positional cloning efforts in soybean include those described by Meksem et al., 2000; Kanazin et al. (1996) *Proc Natl Acad Sci USA* 93(21):11746-11750; Zhu et al. (1996) *Mol Gen Genet.* 252:483-488. Exemplary hybridization methods are disclosed in Examples 4 and 5.

Mapped SCN, SDS, or SCN and SDS markers can be used as DNA probes to hybridize and select homologous genomic clones from such libraries. Alternatively, the DNA of mapped marker clones are sequenced to design PCR primers that amplify and therefore identify homologous genomic clones from such libraries. Either method is used to identify large-insert soybean clones that is then used to start or finish a contig constructed in chromosome walking to clone an SCN, SDS, or SCN and SDS resistance QTL.

As examples, the positional cloning strategy was successfully used to clone the cystic fibrosis gene in humans (Rommens et al. (1989) *Science* 245:1059-1065), an omega-3 desaturase gene in *Arabidopsis* Arondel et al. (1992) *Science* 258:1353-1355), a protein kinase gene (Pto) conferring fungal resistance in tomato (Martin et al. (1993) *Science* 262: 1432-1436), a YAC clone containing the Pointless gene that suppresses abscission of flowers and fruit in tomato (Zhang et al. (1994) *Mol Gen Genet.* 244:613-621), and sequences comprising the rhg1 and Rhg4 genes, disclosed herein.

VI.C. Mapping Methods

The isolated and purified polynucleotide sequences disclosed herein can also be used in a variety of applications pertaining to mapping SCN and SDS resistance. For example, the isolated polynucleotides disclosed herein are useful in studies of genome organization; in gene structure and organization experiments; in BAC-FISH experiments; in chromosome painting techniques; and in chromosome manipulation.

Thus, in accordance with the present invention, the nucleic acid sequences which encode SCN/SDS resistance polypeptides can also be used to generate hybridization probes which are useful for mapping naturally occurring genomic sequences and/or resistance loci. The sequences can be mapped to a particular chromosome or to a specific region of the chromosome using well-known techniques. Such techniques include FISH, FACS, or artificial chromosome constructions, such as yeast artificial chromosomes, bacterial artificial chromosomes, bacterial P1 constructions or single chromosome cDNA libraries as reviewed in Price (1993) *Blood Rev* 7:127-134, and Trask (1991) *Trends Genet.* 7:149-154.

FISH (as described in Verma et al. (1988) *Human Chromosomes: A Manual of Basic Techniques*, Pergamon Press, New York, N.Y.) can be correlated with other physical chromosome mapping techniques and genetic map data. Examples of genetic map data can be found in the 1994 Genome Issue of *Science* (265:1981f). Correlation between the location of the gene encoding SCN, SDS, or both SCN and SDS resistance on a physical chromosomal map and another resistance characteristic, or lack thereof, can help delimit the region of DNA associated with that genetic characteristic. The nucleotide sequences of the subject invention can be used to detect differences in gene sequences between normal, carrier, or susceptible individuals.

In situ hybridization of chromosomal preparations and physical mapping techniques such as linkage analysis and chromosomal painting using established chromosomal markers can be used for extending genetic maps. Often the placement of a gene on the chromosome of another plant species, such as tomato species or other soybean species, reveals associated markers also found in other plants such as soybeans even if the number or arm of a particular chromosome is not known. New sequences can be assigned to chromosomal arms, or parts thereof, by physical mapping. This provides valuable information to investigators searching for resistance or other genes using positional cloning or other gene discovery techniques. Once the resistance or other gene has been crudely localized by genetic linkage to a particular genomic region, any sequences mapping to that area can represent associated or regulatory genes for further investigation. The nucleotide sequences of the present invention can thus also be used to detect differences in the chromosomal location due to translocation, inversion, etc. among normal, carrier, or susceptible individuals, and to detect gene regulatory sequences (e.g. promoters).

Hybridization of the subject DNAs to reference chromosomes can also be performed to give information on relative copy numbers of sequences. Normalization is required to obtain absolute copy number information. One convenient method to do this is to hybridize a probe, for example a cosmid specific to some single locus in the normal haploid genome, to the interphase nuclei of the subject cell or cell population(s) (or those of an equivalent cell or representative cells therefrom, respectively). Quantiation of the hybridization signals in a representative population of such nuclei gives the absolute sequence copy number at that location. Given that information at one locus, the intensity (ratio) information from the hybridization of the subject DNA(s) to the reference condensed chromosomes gives the absolute copy number over the rest of the genome. In practice, use of more than one reference locus can be desirable. In this case, the best fit of the intensity (ratio) data through the reference loci can give a more accurate determination of absolute sequence copy number over the rest of the genome.

Thus, the methods of the present invention can provide information on the absolute copy numbers of substantially all RNA or DNA sequences in subject cell(s) or cell population(s) as a function of the location of those sequences in a reference genome. Additionally, chromosome painting probes can be prepared using the markers and sequence data herein disclosed. Hybridization with one or more of such probes indicates the absolute copy numbers of the sequences to which the probes bind.

Further, when the subject nucleic acid sequences are DNA, the reference copy numbers can be determined by Southern analysis. When the subject nucleic acid sequences are RNA, the reference copy numbers can be determined by Northern analysis.

VI.D. Assays Kits

In another aspect, the present invention provides assay kits for detecting the presence, in biological samples, of a polynucleotide that encodes a polypeptide of the present invention or of a chromosome bearing a gene or locus of the present invention, the kits comprising a first container that contains a second polynucleotide identical or complementary to a segment of at least 10 contiguous nucleotide bases of, as a preferred example, any of SEQ ID NOs:13 and 16-19.

VII. Recombinant Expression B Expression Cassettes

The term "expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest can be chimeric. The expression cassette can also be one which is naturally occurring but has been obtained in a recombinant form useful for heterologous expression. The expression cassettes can also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments.

VII.A. Promoters

The expression of the nucleotide sequence in the expression cassette can be under the control of a constitutive promoter or an inducible promoter which initiates transcription only when the host cell is exposed to some particular external stimulus. For bacterial production of a SCN/SDS resistance polypeptide, exemplary promoters include Simian virus 40 early promoter, a long terminal repeat promoter from retrovirus, an actin promoter, a heat shock promoter, and a metallothionein protein. For in vivo production of a SCN/SDS resistance polypeptide in plants, exemplary constituitve promoters are derived from the CaMV 35S, rice actin, and maize ubiquitin genes, each described herein below. Exemplary inducible promoters for this purpose include the chemically inducible PR-1a promoter and a wound-inducible promoter, also described herein below.

Selected promoters can direct expression in specific cell types (such as leaf epidermal cells, mesophyll cells, root cortex cells) or in specific tissues or organs (roots, leaves or flowers, for example). Exemplary tissue-specific promoters include well-characterized root-, pith-, and leaf-specific promoters, each described herein below.

Depending upon the host cell system utilized, any one of a number of suitable promoters can be used. Promoter selection can be based on expression profile and expression level. The following are non-limiting examples of promoters that can be used in the expression cassettes.

VII.A.1. Constituitive Expression

35S Promoter. The CaMV 35S promoter can be used to drive constituitive gene expression. Construction of the plasmid pCGN1761 is described in the published patent application EP 0 392 225, which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or gene sequences (including microbial ORF sequences) within its polylinker for the purpose of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter.

Actin Promoter. Several isoforms of actin are known to be expressed in most cell types and consequently the actin promoter is a good choice for a constitutive promoter. In particular, the promoter from the rice ActI gene has been cloned and characterized (McElroy et al. (1990) *Plant Cell* 2:163-171). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. (1991) *Mol Gen Genet.* 231:150-160). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (1991) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. (1993) *Plant Cell Rep* 12:506-509).

Ubiquitin Promoter. Ubiquitin is another gene product known to accumulate in many cell types and its promoter has been cloned from several species for use in transgenic plants (e.g. sunflower—Binet et al. (1991) *Plant Science* 79: 87-94 and maize—Christensen et al. (1989) *Plant Molec Biol* 12:619-632). The maize ubiquitin promoter has been developed in transgenic monocot systems and its sequence and vectors constructed for monocot transformation are disclosed in the patent publication EP 0 342 926 which is herein incorporated by reference. Taylor et al. (1993) *Plant Cell Rep* 12:491-495 describe a vector (pAHC25) that comprises the maize ubiquitin promoter and first intron and its high activity in cell suspensions of numerous monocotyledons when introduced via microprojectile bombardment. The ubiquitin promoter is suitable for gene expression in transgenic plants, especially monocotyledons. Suitable vectors are derivatives of pAHC25 or any of the transformation vectors described in this application, modified by the introduction of the appropriate ubiquitin promoter and/or intron sequences.

VII.A.2. Inducible Expression

Chemically Inducible PR-1a Promoter. The double 35S promoter in pCGN1761ENX can be replaced with any other promoter of choice which will result in suitably high expression levels. By way of example, one of the chemically regulatable promoters described in U.S. Pat. No. 5,614,395 can replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemical/pathogen regulated tobacco PR-1a promoter is cleaved from plasmid pCIB1004 (for construction, see EP 0 332 104, which is hereby incorporated by reference) and transferred to plasmid pCGN 1761 ENX (Uknes et al. (1992) *The Plant Cell* 4:645-656).

pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761 ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described below. Various chemical regulators can be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395, herein incorporated by reference.

Wound-inducible Promoters. Wound-inducible promoters can also be suitable for gene expression. Numerous such promoters have been described (e.g. Xu et al. (1993) *Plant Molec Biol* 22:573-588; Logemann et al. (1989) *Plant Cell* 1:151-158; Rohrmeier & Lehle (1993) *Plant Molec Biol* 22:783-792; Firek et al. (1993) *Plant Molec Biol* 22:129-142; Warner et al. (1993) *Plant J* 3:191-201) and all are suitable for use with the instant invention. Logemann et al. (1989) describe the 5' upstream sequences of the dicotyledonous potato wunI gene. Xu et al. (1993) show that a wound-inducible promoter from the dicotyledon potato (pin2) is active in the monocotyledon rice. Further, Rohrmeier & Lehle (1993) describe the cloning of the maize WipI cDNA which is wound induced and which can be used to isolate the cognate promoter using standard techniques. Similarly, Firek et al. (1993) and Warner et al. (1993) have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

VII.A.3. Tissue-Specific Expression

Root Promoter. Another pattern of gene expression is root expression. A suitable root promoter is described by de Framond (1991) *FEBS* 290:103-106 and also in the published patent application EP 0 452 269, which is herein incorporated by reference. This promoter is transferred to a suitable vector such as pCGN1761ENX for the insertion of a selected gene and subsequent transfer of the entire promoter-gene-terminator cassette to a transformation vector of interest.

Pith Promoter. International Publication No. WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

Leaf Promoter. A maize gene encoding phosphoenol carboxylase (PEPC) has been described by Hudspeth & Grula (1989) *Plant Molec Biol* 12:579-589. Using standard molecular biological techniques the promoter for this gene can be used to drive the expression of any gene in a leaf-specific manner in transgenic plants.

VII.B. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons.

VII.C. Sequences for the Enhancement or Regulation of Expression

Numerous sequences have been found to enhance gene expression from within the transcriptional unit and these sequences can be used in conjunction with the genes of this invention to increase their expression in transgenic plants.

If desired, modifications around the cloning sites can be made by the introduction of sequences that can enhance translation. This is particularly useful when overexpression is desired. For example, pCGN1761ENX can be modified by optimization of the translational initiation site as disclosed in U.S. Pat. No. 5,639,949, incorporated herein by reference.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al. (1987) *Genes Develop* 1:1183-1200). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. (1987) *Nucl Acids Res* 15:8693-8711; Skuzeski et al. (1990) *Plant Molec Biol* 15:65-79).

VII.D. Targeting of the Gene Product within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. (1988) *J Biol Chem* 263:15104-15109). These signal sequences can be fused to heterologous gene products to effect the import of heterologous products into the chloroplast (van den Broeck et al. (1985) *Nature* 313:358-363). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, U.S. Pat. No. 5,639,949, herein incorporated by reference.

Other gene products are localized to other organelles such as the mitochondrion and the peroxisome (e.g. Unger et al. (1989) *Plant Molec Biol* 13:411-418). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (1989) *Proc Natl Acad Sci USA* 82:6512-6516).

In addition, sequences have been characterized which cause the targeting of gene products to other cell compartments. Amino terminal sequences are responsible for targeting to the ER, the apoplast, and extracellular secretion from aleurone cells (Koehler & Ho (1990) *Plant Cell* 2:769-783). Additionally, amino terminal sequences in conjunction with carboxy terminal sequences are responsible for vacuolar targeting of gene products (Shinshi et al. (1990) *Plant Molec Biol* 14:357-368).

By the fusion of the appropriate targeting sequences described above to transgene sequences of interest, it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement can be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. (1982) in *Methods in Chloroplast Molecular Biology*, Edelmann et al. (Eds.), pp 1081-1091, Elsevier and Wasmann et al. (1986) *Mol Gen Genet*. 205:446-453.

These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

VIII. Recombinant Expression B Vectors

Suitable expression vectors which can be used include, but are not limited to, the following vectors or their derivatives: human or animal viruses such as vaccinia virus or adenovirus, yeast vectors, bacteriophage vectors (e.g., lambda phage), and plasmid and cosmid DNA vectors.

Numerous vectors available for plant transformation are known to those of ordinary skill in the plant transformation arts, and the genes pertinent to this invention can be used with any such vectors. Exemplary vectors include pCIB200, pCIB2001, pCIB10, pCIB3064, pSOG19, and pSOG35, each described herein below. The selection of vector will depend upon the preferred transformation technique and the target species for transformation.

VIII.A. *Agrobacterium* Transformation Vectors.

Many vectors are available for transformation using *Agrobacterium tumefaciens*. These typically carry at least one T-DNA border sequence and include vectors such as pBIN19 (Bevan (1984) *Nucl Acids Res* 12:8711-8721) and pXYZ. Below, the construction of two typical vectors suitable for *Agrobacterium* transformation is described.

pCIB200 and PCIB2001. The binary vectors pclB200 and pCIB2001 are used for the construction of recombinant vectors for use with *Agrobacterium* and are constructed in the following manner. pTJS75kan is created by NarI digestion of pTJS75 (Schmidhauser & Helinski (1985) *J Bacteriol* 164:446-455) allowing excision of the tetracycline-resistance gene, followed by insertion of an AccI fragment from pUC4K carrying an NPTII (Messing & Vierra (1982) *Gene* 19:259-268; Bevan et al. (1983) *Nature* 304:184-187; McBride et al. (1990) *Plant Molecular Biology* 14:266-276). XhoI linkers are ligated to the EcoRV fragment of PCIB7 which contains the left and right T-DNA borders, a plant selectable nos/nptII chimeric gene and the pUC polylinker (Rothstein et al. (1987) *Gene* 53:153-161), and the XhoI-digested fragment are cloned into SalI-digested pTJS75kan to create pCIB200 (see also EP 0 332 104, herein incorporated by reference).

pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, Ssfl, KpnI, BglII, XbaI, SalI, MluI, BclI, AvrII, ApaI, HpaI, and StuI. pCIB2001,in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

PCIB10 and Hygromycin Selection Derivatives thereof. The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (1987). Various derivatives of pCIB10 are constructed which incorporate the gene for hygromycin B phosphotransferase described by Gritz et al. (1983) *Gene* 25:179-188. These derivatives enable selection of transgenic plant cells on hygromycin only (pCIB743), or hygromycin and kanamycin (pCIB715, pCIB717).

VIII.B. Other Plant Transformation Vectors

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

pCIB3064. pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the Internation Publication No. WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025.

The GUS gene is then excised from pCIB3025 by digestion with SaiI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. (1987) *EMBO J.* 6:2519-2523). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

pSOG19 and pSOG35. pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize AdhI gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech, Palo Alto, Calif.) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

VIII.C. Selectable Markers

For certain target species, different antibiotic or herbicide selection markers can be preferred. Selection markers used routinely in transformation include the nptII gene, which confers resistance to kanamycin and related antibiotics (Messing & Vierra (1982) *Gene* 19:259-268; Bevan et al., 1983), the bar gene, which confers resistance to the herbicide phosphinothricin (White et al. (1990) *Nucl Acids Res* 18:1062; Spencer et al. (1990) *Theor Appl Genet.* 79:625-631), the hph gene, which confers resistance to the antibiotic hygromycin (Blochlinger & Diggelmann (1984) *Mol Cell Biol* 4:2929-2931), the dhfr gene, which confers resistance to methatrexate (Bourouis et al., (1983) *EMBO J.* 2(7):1099-1104), and the EPSPS gene, which confers resistance to glyphosate (U.S. Pat. Nos. 4,940,935 and 5,188,642).

IX. Recombinant Expression B Host Cells

The term "host cell", as used herein, refers to a cell into which a heterologous nucleic acid molecule has been introduced. Transformed cells, tissues, or organisms are understood to encompass not only the end product of a transformation process, but also transgenic progeny thereof. A host cell strain can be chosen which modulates the expression of the inserted sequences, or modifies and processes the gene product in the specific fashion desired. For example, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. Expression in a bacterial system can be used to produce a non-glycosylated core protein product. Expression in yeast will produce a glycosylated product. Expression in plant cells can be used to ensure "native" glycosylation of a heterologous protein.

The present invention provides methods for recombinant expression of SCN/SDS resistance genes in plants by the construction of transgenic plants. The phrase "a plant, or parts thereof" as used herein shall mean an entire plant; and shall mean the individual parts thereof, including but not limited to seeds, leaves, stems, and roots, as well as plant tissue cultures. Transgenic plants of the present invention are understood to encompass not only the end product of a transformation method, but also transgenic progeny thereof. The term "converted plant" as used herein shall mean any plant (1) having resistance to SDS or resistance to SCN and (2) and was derived by genetic selection employing RFLP, RADP, AFLP, or microsatellite (SSR) data for at least one of the loci herein defined.

Preferably, the plant is a soybean plant. However, disease resistance can be conferred to a wide variety of plant cells, including those of gymnosperms, monocots, and dicots. Although the gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, tobacco, tomato, sorghum and sugarcane.

X. Recombinant Expression B Transfection and Transformation Methods

Expression constructs are transfected into a host cell by a standard method suitable for the selected host, including electroporation, calcium phosphate precipitation, DEAE-Dextran transfection, liposome-mediated transfection, infection using a retrovirus, transposon-mediated transfer, and particle bombardment techniques. The SCN/SDS resistance gene-encoding nucleotide sequence carried in the expression construct can be stably integrated into the genome of the host or it can be present as an extrachromosomal molecule. Below are descriptions of representative techniques for transforming both dicotyledonous and monocotyledonous plants.

X.A. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al. (1984) *EMBO J.* 3:2717-2722; Potrykus et al. (1985) *Mol Gen Genet.* 199:169-177; Reich et al. (1986) *Biotechnology* 4:1001-1004; and Klein et al. (1987) *Nature* 327:70-73. In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain, which can depend of the complement of vir genes carried by the host *Agrobacterium* strain either on a co-resident Ti plasmid or chromosomally (e.g. strain CIB542 for pCIB200 and pCIB2001 (Uknes et al. (1993) *Plant Cell* 5:159-169). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer (1988) *Nucl Acids Res* 16:9877).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

X.B. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation can have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. (1986) *Biotechnology* 4:1093-1096).

patent Application Nos. EP 0 292 435, EP 0 392 225, and International Publication No. WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (1990) *Plant Cell* 2:603-618 and Fromm et al. (1990) *Biotechnology* 8:833-839 have published techniques for transformation of A188-derived maize line using particle bombardment. Furthermore, International Publication No. WO 93/07278 and Koziel et al. (1993) *Biotechnology* 11: 194-200 describe techniques for the transformation of elite inbred lines of maize by particle bombardment. This technique utilizes immature maize embryos of 1.5-2.5 mm length excised from a maize ear 14-15 days after pollination and a PDS-100He BIOLISTICS® device for bombardment.

Transformation of rice can also be undertaken by direct gene transfer techniques utilizing protoplasts or particle bombardment. Protoplast-mediated transformation has been described for Japonica-types and Indica-types (Zhang et al. (1988) *Plant Cell Rep* 7:379-384; Shimamoto et al. (1989) *Nature* 338:274-277; Datta et al. (1990) *Biotechnology* 8:736-740). Both types are also routinely transformable using particle bombardment (Christou et al. (1991) *Biotechnology* 9:957-962). Furthermore, Internation Publication Number WO 93/21335 describes techniques for the transformation of rice via electroporation. Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (1992) *Biotechnology* 10:667-674 using particle bombardment into cells of type C long-term regenerable callus, and also by Vasil et al. (1993) *Biotechnology* 11:1553-1558 and Weeks et al. (1993) *Plant Physiol* 102:1077-1084 using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog (1962) *Physiologia Plantarum* 15:473-497) and 3 mg/l 2,4-D for induction of somatic embryos, which is allowed to proceed in the dark. On the chosen day for bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical.

An appropriate gene-carrying plasmid (such as pCIB3064 or pSG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hours, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

More recently, transformation of monocotyledons using *Agrobacterium* has been described. See WO 94/00977 and U.S. Pat. No. 5,591,616, both of which are incorporated herein by reference.

XI. Antibodies

The present invention also provides an antibody immunoreactive with an SCN/SDS resistance polypeptide. The term "antibody" indicates an immunoglobulin protein, or functional portion thereof, including a polyclonal antibody, a monoclonal antibody, a chimeric antibody, a single chain antibody, Fab fragments, and an Fab expression library. "Functional portion" refers to the part of the protein that binds a molecule of interest. In a preferred embodiment, an antibody of the invention is a monoclonal antibody. Techniques for preparing and characterizing antibodies are well known in the art (See, e.g., Harlow and Lane (1988). A monoclonal antibody of the present invention can be readily prepared through use of well-known techniques such as the hybridoma techniques exemplified in U.S. Pat. No. 4,196,265 and the phage-displayed techniques disclosed in U.S. Pat. No. 5,260, 203.

The phrase "specifically (or selectively) binds to an antibody", or "specifically (or selectively) immunoreactive with", when referring to a protein or peptide, refers to a binding reaction which is determinative of the presence of the protein in a heterogeneous population of proteins and other biological materials. Thus, under designated immunoassay conditions, the specified antibodies bind to a particular protein and do not show significant binding to other proteins present in the sample. Specific binding to an antibody under such conditions can require an antibody that is selected for its specificity for a particular protein. For example, antibodies raised to a protein with an amino acid sequence encoded by the nucleic acid sequence of SEQ ID No:13 can be selected to obtain antibodies specifically immunoreactive with that protein and not with unrelated proteins.

The use of a molecular cloning approach to generate antibodies, particularly monoclonal antibodies, and more particularly single chain monoclonal antibodies, are also provided. The production of single chain antibodies has been described in the art. See, e.g., U.S. Pat. No. 5,260,203. For this approach, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by heavy (H) and light (L) chain combinations in a single chain, which further increases the chance of finding appropriate antibodies. Thus, an antibody of the present invention, or a "derivative" of an antibody of the present invention, pertains to a single polypeptide chain binding molecule which has binding specificity and affinity substantially similar to the binding specificity and affinity of the light and heavy chain aggregate variable region of an antibody described herein.

The term "immunochemical reaction", as used herein, refers to any of a variety of immunoassay formats used to detect antibodies specifically bound to a particular protein, including but not limited to, competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, and immunoelectrophoresis assays, etc. See Harlow and Lane (1988) for a description of immunoassay formats and conditions.

XII. Method for Detecting a SCN/SDS Resistance Polypeptide

In another aspect of the invention, a method is provided for detecting a level of SCN/SDS resistance polypeptide using an antibody that specifically recognizes a SCN/SDS resistance polypeptide, or portion thereof. In a preferred embodiment, biological samples from an experimental plant and a control plant are obtained, and SCN/SDS resistance polypeptide is detected in each sample by immunochemical reaction with the SCN/SDS resistance polypeptide antibody. More preferably, the antibody recognizes amino acids of SEQ ID NO:14 and is prepared according to a method of the present invention for producing such an antibody.

In one embodiment, a SCN/SDS resistance polypeptide antibody is used to screen a biological sample for the presence of a SCN/SDS resistance polypeptide. A biological sample to be screened can be a biological fluid such as extracellular or intracellular fluid, or a cell or tissue extract or homogenate. A biological sample can also be an isolated cell (e.g., in culture) or a collection of cells such as in a tissue sample. A tissue sample can be suspended in a liquid medium or fixed onto a solid support such as a microscope slide. In accordance with a screening assay method, a biological sample is exposed to an antibody immunoreactive with an SCN/SDS resistance polypeptide whose presence is being assayed, and the formation of antibody-polypeptide complexes is detected. Techniques for detecting such antibody-antigen conjugates or complexes are well known in the art and include but are not limited to centrifugation, affinity chromatography and the like, and binding of a labeled secondary antibody to the antibody-candidate receptor complex.

XIII. Identification of Modulators of SCN/SDS Resistance

The present invention further discloses a method for identifying a compound that modulates SCN/SDS resistance. As used herein, the terms "candidate substance" and "candidate compound" are used interchangeably and refer to a substance that is believed to interact with another moiety, wherein a biological activity is modulated. For example, a representative candidate compound is believed to interact with a complete, or a fragment of, a SCN/SDS resistance polypeptide, and which can be subsequently evaluated for such an interaction. Exemplary candidate compounds that can be investigated using the methods of the present invention include, but are not restricted to, compounds that confer SCN/SDS resistance, viral epitopes, peptides, enzymes, enzyme substrates, co-factors, lectins, sugars, oligonucleotides or nucleic acids, oligosaccharides, proteins, chemical compounds small molecules, and monoclonal antibodies. A candidate compound to be tested by these methods can be a purified molecule, a homogenous sample, or a mixture of molecules or compounds.

As used herein, the term "modulate" means an increase, decrease, or other alteration of any or all chemical and biological activities or properties of a wild-type SCN/SDS resistance polypeptide, preferably a SCN/SDS resistance polypeptide of SEQ ID NO:14. Preferably, a SCN/SDS resistance modulator is an agonist of SCN/SDS resistance protein activity. As used herein, the term "agonist" means a substance that supplements or potentiates the biological activity of a functional SCN/SDS resistance protein.

In accordance with the present invention there is also provided a rapid and high throughput screening method that relies on the methods described above. This screening method comprises separately contacting each compound with a plurality of substantially identical samples. In such a screening method the plurality of samples preferably comprises more than about $10^4$ samples, or more preferably comprises more than about $5\times10^4$ samples. In an alternative high-throughput strategy, each sample can be contacted with a plurality of candidate compounds.

XIII.A. Methods for Identifying Modulators of SCN/SDS Resistance Gene Expression The nucleic acid sequences of the present invention can be used to identify regulators of SCN/SDS resistance polypeptide gene expression. Several molecular cloning strategies can be used to identify substances that specifically bind SCN/SDS resistance polypeptide cis-regulatory elements. A preferred promoter region to be used in such assays is an SCN/SDS resistance polypeptide promoter region from soybean, more preferably the promoter region includes some or all amino acids of SEQ ID NO:14.

In one embodiment, a cDNA library in an expression vector, such as the lambda-gt11 vector, can be screened for cDNA clones that encode an SCN/SDS resistance polypeptide regulatory element DNA-binding activity by probing the library with a labeled SCN/SDS resistance polypeptide DNA fragment, or synthetic oligonucleotide (Singh et al. (1989) *Biotechniques* 7:252-261). Preferably the nucleotide sequence selected as a probe has already been demonstrated as a protein binding site using a protein-DNA binding assay described above.

In another embodiment, transcriptional regulatory proteins are identified using the yeast one-hybrid system (Luo et al. (1996) *Biotechniques* 20(4):564-568; Vidal et al. (1996) *Proc Natl Acad Sci USA* 93(19):10315-10320; Li and Herskowitz (1993) *Science* 262:1870-1874). In this case, a cis-regulatory element of a SCN/SDS resistance gene is operably fused as an upstream activating sequence (UAS) to one, or typically more, yeast reporter genes such as the lacZ gene, the URA3 gene, the LEU2 gene, the HIS3 gene, or the LYS2 gene, and the reporter gene fusion construct(s) is inserted into an appropriate yeast host strain. It is expected that the reporter genes are not transcriptionally active in the engineered yeast host strain, for lack of a transcriptional activator protein to bind the UAS derived from the SCN/SDS resistance gene promoter region. The engineered yeast host strain is transformed with a library of cDNAs inserted in a yeast activation domain fusion protein expression vector, e.g. pGAD, where the coding regions of the cDNA inserts are fused to a functional yeast activation domain coding segment, such as those derived from the GAL4 or VP16 activators. Transformed yeast cells that acquire a cDNA encoding a protein that binds a cis-regulatory element of a SCN/SDS resistance gene can be identified based on the concerted activation the reporter genes, either by genetic selection for prototrophy (e.g. LEU2, HIS3, or LYS2 reporters) or by screening with chromogenic substrates (lacZ reporter) by methods known in the art.

The present invention also provides an in vivo assay for discovery of modulators of SCN/SDS resistance gene expression. In this case, a transgenic plant is made such that a transgene comprising a SCN/SDS resistance gene promoter and a reporter gene is expressed and a level of reporter gene expression is assayable. Such transgenic animals can be used for the identification of compounds that are effective in modulating SCN/SDS resistance gene expression.

In vitro or in vivo screening approaches may survey more than one modulatable transcriptional regulatory sequence simultaneously.

XIII.B. Methods for Identifying Modulators of SCN/SDS Resistance Polypeptides

According to the method, a SCN/SDS resistance polypeptide is exposed to a plurality of candidate substances, and binding of a candidate substance to the SCN/SDS resistance polypeptide is assayed. A compound is selected that demonstrates specific binding to the SCN/SDS resistance polypeptide. Preferably, the SCN/SDS resistance polypeptide used in the binding assay of the method includes some or all amino acids of SEQ ID NO:14.

The term "binding" refers to an affinity between two molecules, for example, a ligand and a receptor, means a preferential binding of one molecule for another in a mixture of molecules. The binding of the molecules can be considered specific if the binding affinity is about $1\times10^4\ M^{-1}$ to about $1\times10^6\ M^{-1}$ or greater. Binding of two molecules also encompasses a quality or state of mutual action such that an activity of one protein or compound on another protein is inhibitory (in the case of an antagonist) or enhancing (in the case of an agonist).

Several techniques can be used to detect interactions between a protein and a chemical ligand without employing an in vivo ligand. Representative methods include, but are not limited to, fluorescence correlation spectroscopy, surface-enhanced laser desorption/ionization, and biacore technology, each described herein below. These methods are amenable to automated, high-throughput screening.

Fluorescence Correlation Spectroscopy (FCS). FCS measures the average diffusion rate of a fluorescent molecule within a small sample volume (Madge et al. (1972) *Phys Re Lett* 29:705-708, Maiti et al. (1997) *Proc Natl Acad Sci USA,* 94:11753-11757). The sample size can be as low as $10^3$ fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding. In a typical experiment, the target to be analyzed is expressed as a recombinant protein with a sequence tag, such as a poly-histidine sequence, inserted at the N-terminus or C-terminus. The target protein is expressed in *E. coli*, yeast, or plant cells. The protein is purified by chromatography. For example, the poly-histidine tag can be used to bind the expressed protein to a metal chelate column such as $Ni^{2+}$ chelated on iminodiacetic acid agarose. The protein is then labeled with a fluorescent tag such as carboxytetramethylrhodamine or BODIPY™ (Molecular Probes, Eugene, Oreg.). The protein is then exposed in solution to a candidate compound, and its diffusion rate is determined by FCS, using for example, instrumentation available from Carl Zeiss, Inc. (Thornwood, N.Y.). Ligand binding is determined by changes in the diffusion rate of the protein.

Surface-Enhanced Laser Desorption/Ionization (SELDI). SELDI can be used in combination with a time-of-flight mass spectrometer (TOF) to provide a means to rapidly analyze molecules retained on a chip (Hutchens and Yip (1993) *Rapid Commun Mass Spectrom* 7:576-580). It can be applied to ligand-protein interaction analysis by covalently binding the target protein on the chip and using mass spectroscopy to analyze the small molecules that bind to the target protein (Worrall et al. (1998) *Anal Biochem* 70:750-756). In a typical experiment, the target to be analyzed is recombinantly expressed, optionally with a tag, such as poly-histidine, to facilitate purification and handling. The purified protein is bound to the SELDI chip either by utilizing the poly-histidine tag or by other interaction such as ion exchange or hydrophobic interaction. The chip thus prepared is then exposed to a candidate compound via, for example, a delivery system able to pipet the ligands in a sequential manner (autosampler). The chip is then washed in buffers of increasing stringency, for example a series of buffer solutions containing incrementally increasing ionic strength. After each wash, the bound material is analyzed by SELDI-TOF. Compounds that specifically bind the target are identified by elution in high stringency washes.

Biacore. Biacore technology utilizes changes in the refractive index at the surface layer upon binding of a ligand to a protein immobilized on the layer. In this system, a collection of small ligands is injected sequentially in a 2-5 microliter cell, wherein the protein is immobilized within the cell. Binding is detected by surface plasmon resonance (SPR) of laser light refracting from the surface. In general, the refractive index change for a given change of mass concentration at the surface layer is practically the same for all proteins and peptides, allowing a single method to be applicable for any protein (Liedberg et al. (1983) *Sensors Actuators* 4:299-304; Malmquist (1993) *Nature* 361:186-187). In a typical experiment, the target protein to be analyzed is recombinantly expressed an purified according to standard methods. It is bound to the Biacore chip either by utilizing a poly-histidine tag or by other interaction such as ion exchange or hydrophobic interaction. The chip thus prepared is then exposed to a candidate compound via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics on rate and off rate allows the discrimination between non-specific and specific interaction.

Rational Drug Design. Similarly, the knowledge of the structure a native SCN/SDS resistance polypeptide provides an approach for rational drug design. The structure of an SCN/SDS resistance polypeptide can be determined by X-ray crystallography or by computational algorithms that generate three-dimensional representations. See Huang et al. (2000) and Saqi et al. (1999) Computer models can further predict binding of a protein structure to various substrate molecules, that can be synthesized and tested. Additional drug design techniques are described in U.S. Pat. Nos. 5,834,228 and 5,872,011.

XIV. Modulation of SCN/SDS Resistance in a Plant

In accordance with the present invention a method of modulating SCN/SDS resistance in a plant is also provided. The method comprises the step of administering to the plant an effective amount of a substance that modulates expression of an SCN/SDS resistance activity-encoding nucleic acid molecule in the plant to thereby modulate SCN/SDS resistance in the plant. Preferably, the substance that modulates expression of an SCN/SDS resistance activity-encoding nucleic acid molecule comprises a ligand for a modulatable transcriptional regulatory sequence of an SCN/SDS resistance activity-encoding nucleic acid molecule identified in accordance with the methods described above. More preferably, the plant is a soybean plant.

Particularly, provided chemical entities (e.g. small molecule mimetics) do not naturally occur in any cell of a lower eucaryotic organism such as yeast. More particularly, provided chemical entities do not naturally occur in any cell, whether of a multicellular or a unicellular organism. Even more particularly, the provided chemical entity is not a naturally occurring molecule, e.g. it is a chemically synthesized entity. Provided chemical entities can be hydrophobic, polycyclic, or both, molecules, and are typically about 500-1,000 daltons in molecular weight.

XV. Method for Providing SCN/SDS Resistance B Transgenic Plants

A "transgenic plant" is a plant that has been genetically modified to contain and express heterologous DNA sequences, either as regulatory RNA molecules or as proteins. As specifically exemplified herein, a transgenic plant is genetically modified to contain and express at least one heterologous DNA sequence operably linked to and under the regulatory control of transcriptional control sequences which function in plant cells or tissue or in whole plants. As used herein, a transgenic plant also refers to progeny of the initial transgenic plant where those progeny contain and are capable of expressing the heterologous coding sequence under the regulatory control of the plant-expressible transcription control sequences described herein. Seeds containing transgenic embryos are encompassed within this definition as are cuttings and other plant materials for vegetative propagation of a transgenic plant.

When plant expression of a heterologous gene or coding sequence of interest is desired, that coding sequence is operably linked in the sense orientation to a suitable promoter and advantageously under the regulatory control of DNA sequences which quantitatively regulate transcription of a downstream sequence in plant cells or tissue or in planta, in the same orientation as the promoter, so that a sense (i.e., functional for translational expression) mRNA is produced. A transcription termination signal, for example, as polyadenylation signal, functional in a plant cell is advantageously placed downstream of the SCN/SDS resistance coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing.

In the present invention, the SCN/SDS resistance coding sequence can optionally serve as a selectable marker for transformation of plant cells or tissue. Where constitutive gene expression is desired, suitable plant-expressible promoters include a native promoter (e.g. SEQ ID NO:15) of the SCN/SDS coding sequences set forth herein as the native promoter is activated in the presence of SCN; the 35S or 19S promoters of Cauliflower Mosaic Virus; the nos, ocs or mas promoters of *Agrobacterium tumefaciens* Ti plasmids; and others known to the art.

Indeed, a native promoter (e.g. SEQ ID NO:15) of the SCN/SDS coding sequences set forth herein is activated in the presence of SCN and thus can be used to produce transgenic plants in accordance with the techniques disclosed herein. Particularly, the native promoter can be linked to a nucleic acid encoding a polypeptide of interest in a construct, and the construct can be used to a prepare a transgenic plant in accordance with techniques described herein. Other techniques are disclosed in U.S. Pat. Nos. 5,994,526 and 5,994,527, herein incorporated by reference in their entirety. The polypeptide of interest is then expressed in the plant when the promoter is activated, such as in the presence of SCN or other environmental stimulus.

Where tissue-specific expression of the SCN/SDS resistance coding sequence is desired, the skilled artisan will choose from a number of well-known sequences to mediate that form of gene expression as disclosed herein. Environmentally regulated promoters are also well known in the art, and the skilled artisan can choose from well known transcription regulatory sequences to achieve the desired result.

A method for providing a resistance characteristic to a plant is therefore disclosed. The method comprises introducing to said plant a construct comprising a nucleic acid sequence encoding an SCN/SDS resistance gene product operatively linked to a promoter, wherein production of the SCN/SDS resistance gene product in the plant provides a resistance characteristic to the plant. The construct can further comprises a vector selected from the group consisting of a plasmid vector or a viral vector. The SCN/SDS resistance gene product comprises a protein having an amino acid sequence as set forth as SEQ ID NO:14. The nucleic acid sequence can be a nucleic acid sequence set forth as SEQ ID NO:13, or a nucleic acid that is substantially similar to SEQ ID NO:13, and which encodes an SCN/SDS resistance polypeptide.

The resistance characteristic is preferably nematode resistance, fungal resistance or combinations thereof. More preferably, the nematode resistance is *H. glycines* resistance or root knot nematode resistance.

In an alternative embodiment, the construct further comprises another nucleic acid molecule encoding a polypeptide that provides an additional desired characteristic to the plant. Other desired characteristics include yield, drought resistance, chemical resistance (e.g. herbicide or pesticide resistance), spoilage resistance or any or other desired characteristic as would be apparent to one of ordinary skill in the art after review of the disclosure of the present invention. Representative nucleic acids sequences are described in the following U.S. patents (incorporated herein by reference in their entirety): U.S. Pat. No. 5,948,953 to Webb (brown rot fungus resistance); U.S. Pat. No. RE36,449 to Lebrun et al. (herbicide resistance); U.S. Pat. No. 5,952,546 to Bedbrook et al. (delayed ripening tomato plants); and U.S. Pat. No. 5,986,173 to Smeekens et al. (transgenic plants showing a modified fructan pattern).

Optionally, the method further comprises monitoring an insertion point for the construct in the plant genome; and providing for insertion of the construct into the plant genome at a location not associated with the resistance characteristic, the desired characteristic, or both the resistance or the desired characteristic.

XVI. Method for Providing SCN/SDS Resistance B Marker-Assisted Selection and Development of a Breeding Program The present invention relates to a novel and useful method for introgressing, in a reliable and predictable manner, SCN/SDS resistance into non-resistant soybean germplasm. The method involves the genetic mapping of loci associated with SCN/SDS resistance, definition of genetic markers that are linked with SCN/SDS resistance, and a high-throughput PCR-based assay for detecting such a genetic marker. Markers useful in a preferred embodiment of the invention include the following: a locus mapping to linkage group G and mapped by one or more of the markers set forth SEQ ID NOs:1-6, a locus mapping to linkage group A2 and mapped by one or more of the markers set forth as SEQ ID NOs:7-12; or combinations thereof. Also preferably, a genetic marker used for marker-assisted selection comprises a sequence, or portion thereof, of any one of SEQ ID NOs:13 and 16-19, or combinations thereof.

From the sequence data found in SEQ ID NOs:1-13 and 16-19, and from the other markers identified herein, primer pairs, as for example, PCR primer pairs, capable of distinguishing differences among these genotypes are developed. Simple assays for the markers and genes use a label, such as, but not limited to, a covalently attached chromophores, that do not need electrophoresis are developed to increase the capacity of marker assisted selection to help plant breeders. A preferred assay is the TAQMAN™ assay disclosed in Example 6. Non-destructive sampling of dried seed for DNA preparations are developed to allow selection prior to planting, for example, using the methods set forth in Example 9. This enables the testing of the effectiveness of marker assisted selection in predicting field resistance to SON and SDS.

A preferred manner for providing SCN/SDS resistance to a plant involves providing one or more plants from a parental soybean plant line which comprises in its genome one or more molecular markers comprising a sequence, or portion thereof, set forth as any one of SEQ ID NOs:1-13 and 16-19. Preferably, the parental plant is purebreeding for one or more of the molecular markers, more preferably the parent plant is purebreeding for molecular markers comprising a sequence, or portion thereof, set forth as any one of SEQ ID NOs:1-13 and 16-19. In one preferred embodiment, the parental line is "Forrest" or a line derived therefrom.

The SCN/SDS resistance trait can be introgressed into a recipient soybean plant line which is non-resistant or less resistant to SCN/SDS by performing marker-assisted selection based on the molecular markers of the present invention as set forth as SEQ ID NOs:1-13 and 16-19.

Introgressing can be accomplished by any method known in the art, including but not limited to single seed descent, pedigree method, or backcrossing, each described herein below. Additional methods for introgressing are disclosed in U.S. Pat. Nos. 5,948,953 and 6,162,967. Any suitable method can be used, the critical feature being marker-assisted selection of a marker of the present invention using a nucleotide sequence assay.

Single Seed Descent. According to this method, "Forrest" can be crossed to "Essex", and the seed planted in a field. The resulting seed (F2) is planted in the greenhouse and the resulting seeds (F3) are harvested while keeping separate the seeds from each plant. A random F3 seed from each of approximately 200 plants is planted and the resulting F4 seed is harvested. The seeds from each individual plant are again kept separate. A random F4 seed from each of the approximately 200 plants is planted and the resulting F5 seed is harvested. This selection process is repeated until F7 seed is harvested and identified as an inbred line. At each generation beginning with the F3 generation, plants are screened with soybean cyst nematodes, and plants were selected for advancement based upon the presence of SCN resistance and other phenotypic characteristics. Alternatively, plants are screened for the presence of one or more of the molecular markers listed herein using a TAQMAN™ genotyping assay and selected for advancement based upon the presence of one or more of the markers.

Pedigree Method. Using a SCN resistant recombinant inbred line, produced for example by single seed descent, as a donor source, the SCN resistant trait can be introgressed into other germ plasm sources. To develop new germplasm, the SCN resistant recombinant inbred line is used as one of the parents. The resulting progenies are evaluated and selected at various locations for a variety of traits, including SCN resistance. SCN resistance is determined by phenotypic screening or by genotyping based upon the presence of the molecular markers listed herein.

Backcrossing. Using a SCN resistant recombinant inbred line, produced for example by single seed descent, as a donor source, the SCN resistant trait is introgressed into other soybean plant lines. The SCN resistant recombinant inbred line is crossed to a line that demonstrates little or non SCN resistance (the recipient). The resulting plants are crossed back to the recipient soybean plant line that is being converted to SCN resistance. This crossing back to the parental line that is being converted may be repeated several times. After each round of backcrossing, plants are selected for SCN resistance, which can be determined by either phenotypic screening or by the selection of molecular markers linked to SCN resistance loci. Besides selecting for SCN resistance, the plants are also selected that most closely resemble the original plant line being converted to SCN resistance. This selection for the original plant line is done phenotypically or with molecular markers.

In one specific preferred method, $BC_NF1$ plants are genotypically screened for the presence of one or more markers linked to SCN resistance genomic loci. As used herein, the term "$BC_NF1$ plant" is intended to refer to a plant in the first generation after a specific backcross event, the specific backcross event being designated by the term "N", irrespective of the number of previous backcross events employed to produce the plant. Plants having the one or more markers present may preferably be backcrossed with plants of the parental line or, alternatively, be selfed, the plants resulting from either of these events also being genotypically screened for the presence of one or more markers linked to SCN resistance genomic loci. This procedure can be repeated several times.

In another specific preferred method, $BC_NF1$ plants are selfed to produce $BC_NF2$ seeds. $BC_NF2$ plants are then screened either genotypically using, for example a TAQMAN™ assay as disclosed in Example 6, or by phenotypic assessment of SCN resistance. Those plants having present one or more molecular markers linked to SCN resistance, or those plants displaying resistance, depending upon the screening method used, are backcrossed with plants of the parental line to produce $BC_NF3$ seeds and plants. This procedure can be repeated several times. In a soybean breeding program, the methods of the present invention can be used for marker-assisted selection of the molecular markers described herein. Genetic markers closely linked to SCN/SDS resistance genes can be used to indirectly select for favorable alleles more efficiently than phenotypic selection. Genetic markers comprising SCN/SDS resistance genes, as disclosed herein, can be used to select for SCN/SDS resistance genes with optimal efficiency and accuracy.

Marker-assisted selection can be employed to select one or more loci at a wide variety of population development stages in a two-parent population, multiple parent population, or a backcross population. Such populations are described in Fehr (1987) *Breeding Methods for Cultivar Development* J. R. Wilcox (ed.) and *Soybeans: Improvement, Production, and Uses,* 2nd ed.

Marker-assisted selection according to art-recognized methods can be made, for example, step-wise, whereby the different SCN resistance loci are selected in more than one generation; or, as an alternative example, simultaneously, whereby all loci are selected in the same generation. Marker-assisted selection for SCN resistance can be done before, in conjunction with, or after testing and selection for other traits such as seed yield, plant height, seed type, etc. The DNA from target populations, isolated for use in accordance with genetic marker detection, can be obtained from any plant part, and each DNA sample can represent the genotype of single or multiple plant individuals, including seed.

Marker-assisted selection can also be used to confirm previous selection for SCN resistance or susceptibility made by challenging plants with SCNs in the field or greenhouse and scoring the resulting phenotypes. Alternatively, plants can be analyzed by TAQMAN™ genotyping to determine the presence of the above-described molecular markers, thus confirming the presence of a genomic locus associated with SCN resistance. As such, also provided by the present invention are methods for determining the presence or absence of SCN resistance in a soybean plant, or alternatively in a soybean seed. These methods comprise analyzing genomic DNA from a plant or a seed for the presence of one or more of the molecular markers set forth as SEQ ID NOs:1-13 and 16-19. According to this method, the analyzing comprises performing a TAQMAN™ assay as disclosed in Example 6, or any other suitable method known in the art.

The ability to distinguish heterozygotes and their derived heterogeneous lines is important to early generation selection (before the $F_5$) in soybean breeding programs when within population variability is high (Bernard et al. (1988) USDA Tech Bull 1796; Brown et al., 1987). The lower stringency TAQMAN™ 2 assay disclosed herein was most effective for identifying most of the heterogeneous lines in this population. However, the cutoff values of FAM and TET for the efficient identification of heterogeneous lines (or heterozygous F2 lines) is likely to vary across assays and should be set arbitrarily according to expectations of the number of lines that are expected to contain both alleles. The assay was used for analyzing 2,000 lines derived from specific cultivar crosses over 3 days. A single researcher can process 768 sample per day (8×96 samples) since the reading time of the machine is 15 minutes for one 96 well plate and the thermal cycler stage takes about 2 hours.

Table 3 shows that with genomic DNA from 94 cultivars the standard TAQMAN™ allelic discrimination assays and PCR assays provided allele scores that were in good agreement with the cultivar phenotypes (Concibidio, 1997; Bernard et al., 1988). Cultivars, plant introductions (PI), breeding lines and germplasm releases listed in Table 3 were parents in the SCN molecular breeding program at Southern Illinois University-Carbondale (SIUC) from 1997-1999. The prevalence of allele 1 was in good agreement with allele frequencies for markers that are closely linked to Rhg4 (Cregan et al. 1999; Mathews et al. (1998) *Theor Appl Genet.* 97:1047-1052; Mahalingam et al., 1995). Those resistant cultivars sharing allele 1 with the susceptible lines may not require the presence of Rhg4 for resistance to SCN or have derived their resistance to SCN at the Rhg4 locus from alleles derived from cultivars other than Forrest. In addition, some soybean breeders may have been effective in separating even the most closely linked marker from resistance genes using phenotypic selection. However, this is probably infrequent since selection to generate the resistance allele 2 in susceptible cultivars has not occurred frequently. Only three cultivars with allele 2 were susceptible.

TABLE 3

| | Resistant | Susceptible |
|---|---|---|
| Allele 2 | Forrest, Hartwig, Fayette, Pharaoh, Picket, Accomac, Bedford, Delsoy4710, Peking, PI88788, PI209332, PI90763, PI437654, LS92-1088, LS92-4173, LS94-3207, LS95-0259, LS95-0709, LS95-1454, LS96-1631, LS90-1920, LS94-3545, S92-1679, S92-2711A, S94-2086, LN94-10527, A5560K1390, K1425 | MD93-5298 Pace Holladay |
| Allele 1 | Manokin, Mustang, Dwight, Pana, Ina, PI 398680, IA2036, IA3005, LS92-3660, LS93-0292, LS93-0375, LS94-2435, LS96-0735, LS96-3813, LS96-5009, LN92-10725, GX93-1573, SS94-7546, SS94-4337, S95-1908, A4138, A95-483010, M92-1645, M92-1708, M90-184111, K1423, K1424 | Essex, Bragg, Dunfield, Hill, CNS, Lee, Noir1, Ogden, Calhoun, Chesapeake, Choska, Stressland, Macon, Misuzudaiza, Nakasennari, PI 520733, PI567445B, PI567583C, PI567650B, PI 567374, PI 567650B, IA3010, IA1006, TN96-58, N96-180, LN93-11632, LN93-11945, LN95-5417, A94-674017, A94-774021, A96-494018, C1963, HC93-2690, HS93-4118, K1410 |

Summarily, the sequences and methods disclosed herein enable automated, high throughput, rapid genotyping of DNA polymorphisms for selection of SCN/SDS resistance in breeding programs.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Plant Material

A mapping population consisted of approximately 100 recombinant inbred lines derived at the F5 generation from a cross of 'Essex' (Smith & Camper (1973) Crop Sci 13:459) by 'Forrest' (Hartwig & Epps (1973) Crop Sci 13:287). The recombinant inbred line (RILs) population was advanced to the F5:13 generation from 300 plants per RIL per generation (Hnetkovsky et al., 1996). Forrest is resistant to the soybean cyst nematode (SCN) populations classified as race 3 and Essex is susceptible to all populations of SCN (Chang et al., 1997; Meksem et al. 1999).

Example 2

SCN Female Index (FI) Determination

The number of white female cysts was compared on each genotype to the number of white female cysts on a susceptible control, such as Essex, to determine the female index (FI) for each population (Meksem et al., 1999). Seedlings were inoculated with 2000+/−25 eggs from a homogenous isolate of *H. glycines*. All experiments used five single-plant replications per line. The mean number of white female cysts on each genotype and the susceptible control were determined and FI was calculated as the ratio of the mean number of cysts on each genotype to the mean number of cysts on the susceptible check.

Example 3

Characterization of New Markers for SCN/SDS Resistance

Soybean genomic DNA used for AFLP analysis was extracted and purified using the Qiagen (Hilden, Germany) Plant Easy DNA Extraction Kit. Primary template DNA was prepared using the restriction enzymes EcoRI and MseI.

AFLP analysis was performed as described by Vos et al. (1995) *Nuc Acids Res* 23:4407-4414 except that the streptavidin bead selection step was omitted. PCR reactions were performed with using primer pairs derived from each of two sets of primers. Primers within EcoRI set all included the core sequence E: 5'-GAC TGC GTA CCA ATT C (SEQ ID NO: 115) with 1 or 3 base pair extensions. Primers of the MseI set have the sequence M: 5'-GAT GAG TCC TGA GTA A (SEQ ID NO:116) with 1 or 3 base pair extensions. The primer combinations (EA and MC) and (EC and MA) were used for pre-amplification of primary template. Three selective nucleotides per primer were used to generate AFLP fragments from the secondary templates. AFLP bands were labeled with $^{33}$P by primer phosphorylation, separated by electrophoresis on 4% (w/v) PAGE and visualized by exposing X-ray film to the dried gel.

Target AFLP bands on the autoradiograph were matched to the corresponding area in the gel and the appropriate AFLP fragment was excised from the dried gel. The band was eluted from the gel by incubation in 100 ml of water at 4° C. for 1 hour. Sequence isolation in bacterial clones was performed as described by Meksem et al. (1995) *Mol Gen Genet.* 249:74-81 with the modification that the pGEM-T vector (Promega, Madison, Wis.) was ligated to PCR amplified, gel eluted DNA. DNA sequencing of clones allowed PCR primers to be designed for each unique DNA sequence using Oligo 5.0 software (PE Biosystems, Foster City, Calif.). The PCR product was analyzed on 4% (w/v) Metaphor7 (FMC, Rockland, Me.) agarose gel.

AFLP markers that were dominant or co-dominant, in repulsion and in coupling phases were used. For dominant AFLP markers, the band of the dominant allele was cloned and sequenced. The corresponding marker for the recessive allele was isolated by PCR using primers designed from the dominant band sequence. For apparently co-dominant AFLP markers, both, the coupling and repulsion phase bands were cloned simultaneously from the acrylamide gel.

The general strategy employed to identify the specific sequence underlying AFLP band polymorphisms was as follows. If the polymorphism was dominant (e.g. $E_{ATG}M_{CGA}87$) a primer pair was designed to flank each of the unique sequences derived from the AFLP band. Each primer pair was used to amplify genomic DNA from both Essex and Forrest. Any primer set that revealed polymorphism (dominant or co-dominant) between the two parents was used to amplify members of the RIL mapping population. The primer pair that generated a marker on the map corresponding to the map position of the original AFLP band was inferred to be the specific marker STS.

For some AFLP bands the above strategy was ineffective, presumably because polymorphism was within or close to the restriction site used for AFLP linker ligation (e.g. $E_{CGG}M_{AGA}116$). In such cases genomic DNA from the parents and mapping population was used in a modified AFLP protocol as follows. The pre-amplification step was omitted and the six selective nucleotide step was replaced by an extended highly selective MseI primer to which we added the first 7 bases of the sequenced band, combined with a non selective EcoRI primer E (e.g. MseI primer M AGAGACT and EcoRI primer E). The MseI primer was end-labeled by phosphorylating the 5' end with 5 ml [g-$^{33}$P] ATP (3000 Ci/mmol) for 30 min at 37° C. with 10 units of T4 Kinase (Pharmacia, Piscataway, N.J.). Any primer set that revealed polymorphism (dominant or co-dominant) between the two parents was used to amplify members of the RIL mapping population. The primer pair that generated a marker on the map corresponding to the map position of the original AFLP band was inferred to be the specific marker STS.

Example 4

Cloning of SCN/SDS Resistance Genes in Linkage Groups G and A2

The cloned AFLP bands of Example 3 were used to screen the soybean Forrest BamHI or HindIII BAC libraries by PCR as described by Meksem et al. (2000).

Both plasmid and BAC DNA was prepared using the appropriate kit (Qiagen, Hilden, Germany). Sequence determinations were performed by the di-deoxy chain-termination method using Advanced Biosystems (ABI, Foster city, Calif.) "big dye" cycle sequencing separated on ABI 377 automated DNA sequencer.

Plasmids containing clones derived from AFLP bands were sequenced using M13 universal forward and reverse primers. Direct BAC insert sequencing was performed as above with the following modifications: BAC DNA was heated for 30 min at 70° C., and sheared by pippeting into a narrow gauge tip for 2 min. Two primers designed from the target AFLP band sequence were used for sequencing. For the $E_{ATG}M_{CGA}87$ positive BAC insert DNA, the forward primer, named ATG4BACF (SEQ ID NO:117), was 5' gggtttcagataaccgtggtcg 3', the reverse primer was the complementary strand sequences of the ATG4BACF primer. The PCR conditions used was 95° C. for 10 min, then 45 cycles of 95° C. for 30 sec, 55° C. for 20 sec and 60° C. for 4 min.

Example 5

TAQMAN™ Genotyping Assay

PCR primers and TAQMAN™ probes were designed with the primer express program (Perkin-Elmer/Applied Biosystems, Foster City, Calif.) and were custom synthesized by Perkin-Elmer. Two TAQMAN™ probes were designed to encompass the A2D8 (FIG. 1) insertion polymorphisms (underlined). The A2D8 SCAR was derived from the codominant AFLP bands $Ecc_G$-$M_{AA}c417$ (Essex, allele 1, GenBank Accession No. AF286701) and $E_{CCG}$-$M_{AAC}409$ (Forrest, allele 2, GenBank Accession No. AF286700) that contain a homolog (P=2e-05) of one component (Tic22; GenBank Accession No. AAC64606.1) of the protein import apparatus of the chloroplast inner envelope membrane. Allele 1: 5'-TET-TTG CAG ATA TTT TAG TTG ATT GGC C-TAMRA (SEQ ID NO:118). Allele 2: 5'-6FAM-AGT TGA TTG GCT CAA ACC ATG GCC-TAMRA (SEQ ID NO:119). Reverse Primer: 5' d TTG CGT GTG ATC GGT ATT AC 3' (SEQ ID NO:120). Forward primer: 5' d T ACC TGA GTT CTC TCA AGT C 3' (SEQ ID NO:121).

TAQMAN™ reactions were performed essentially as the Perkin-Elmer TAQMAN™ PCR Reagent Kit protocol describes except the PCR reaction was performed in 384 well plates to reduce assay volume and cost. Briefly, each reaction contained long of the extracted DNA, 0.025 units/ml of AMPLITAQ GOLD™ (Perkin-Elmer/Applied Biosystems, Foster City, Calif.), 400 nM of the forward and reverse primers (Research Genetics, Huntsville, Ala.), 50 nM of FAM fluorescent probe and 150 nM of TET fluorescent probe (Perkin-Elmer/Applied Biosystems, Foster City, Calif.) in 1×universal master mix (Perkin-Elmer/Applied Biosystems, Foster City, Calif.). The above ratio of primers and probes was optimized using a series of primer/probe combinations to reach a maximal signal and the balance of the two probes by reading in an ABI 7200 sequence detector. The TAQMAN™ universal PCR master mix is a premix of all the components, except primer and probes, necessary to perform a 5' nuclease assay. The final optimized conditions represented a two step PCR protocol, with two holds followed by cycling, on a 384 well thermal cycler (GeneAmp PCR System 9700, Perkin-Elmer/Applied Biosystems, Foster City, Calif.). The two hold cycles were 50° C. for 2 min and 95° C. for 10 min. The 35 cycles were at 95° C. for 15 sec, 60° C. for 1 min. After amplification the plates were cooled to room temperature and samples were transferred from a 384 well plate to a 96 well MicroAmpJ optical tray and fluorescence was detected on an ABI PrismJ 7200 Sequence Detector (Perkin-Elmer/Applied Biosystems, Foster City, Calif.).

The results were analyzed by allelic discrimination of the sequence detection software (Perkin-Elmer/Applied Biosystems, Foster City, Calif.). Two grouping methods were used to attempt to accurately separate heterogeneous lines from homogeneous lines at each allele. In grouping method 1 (TAQMAN™ 1) a stringent cut-off for FAM (>7) was used for allele 1 compared to heterogenous scores. This served to reduce the number called as potentially heterogeneous to about the percentage expected from the breeding method used for RIL development (6%). Fluorophore ratios were as follows; no amplification (FAM and TET both less than 6 units); allele 1 homozygous (FAM less than 7, TET greater than 7); allele 2 homozygous (FAM greater than 10, TET less than 5); and heterogeneous for allele 1 and allele 2 (FAM greater than 7, TET 5-8). For TAQMAN™ selection grouping method 2 ratios were; no amplification (FAM and TET both less than 6 units); allele 1 homozygous (FAM less than 5, TET greater than 7); allele 2 homozygous (FAM greater than 10, TET less than 5); and heterogeneous for allele 1 and allele 2 (FAM greater than 5, TET 5-9). The FAM and TET signals were stable in the dark for 2 days after PCR. The results were analyzed by allelic discrimination of the sequence detection software (Perkin-Elmer/Applied Biosystems, Foster City, Calif.). Two grouping methods were used to attempt to accurately separate heterogeneous lines from homogeneous lines at each allele. In grouping method 1 (TAQMAN™ 1) a stringent cut-off for FAM (>7) was used for allele 1 compared to heterogenous scores. This served to reduce the number called as potentially heterogeneous to about the percentage expected from the breeding method used for RIL development (6%). Fluorophore ratios were as follows; no amplification (FAM and TET both less than 6 units); allele 1 homozygous (FAM less than 7, TET greater than 7); allele 2 homozygous (FAM greater than 10, TET less than 5); and heterogeneous for allele 1 and allele 2 (FAM greater than 7, TET 5-8). For TAQMAN™ selection grouping method 2 ratios were; no amplification (FAM and TET both less than 6 units); allele 1 homozygous (FAM less than 5, TET greater than 7); allele 2 homozygous (FAM greater than 10, TET less than 5); and heterogeneous for allele 1 and allele 2 (FAM greater than 5, TET 5-9). The FAM and TET signals were stable in the dark for 2 days after PCR.

Example 6

Genotyping Assay Using Gel Electrophoresis Markers

PCR reactions were performed with DNA from the recombinant inbred lines. The 114 and 120 base pair PCR products were generated using the forward and reverse primers (SEQ ID NOs:120-121). The final optimized conditions were 94° C. for 10 min, then 35 cycles of 94° C. for 25 sec, 56° C. for 30 sec and 72° C. for 60 sec. After the PCR reactions were completed, the plates were cooled to room temperature and the PCR products separated by electrophoresis on a 4% (w/v) agarose gel.

Example 7

Allele Distribution in Soybean Germplasm

Genotypes at A2D8 were determined from the genomic DNA of 94 cultivars that represented the parents of populations in the SIUC soybean breeding program from 1997-1999 (Table 3). There were 38 cultivars susceptible to SCN and 56 cultivars resistant to SCN race 3. Allele 2 (R) was found in 32 of 94 cultivars tested. There were very few susceptible genotypes with allele 2 (3 of 32) and the majority of genotypes with allele 2 (29 of 32) were resistant to SCN. In contrast, allele 1 (S) was found in 62 cultivars but frequently in both resistant cultivars (27 of 56) and susceptible cultivars (35 of 38).

Example 8

Selection of SCN/SDS Resistant Seeds

G. max L. seeds used to start cultures should be less than six months old and have been stored in darkness at 4° C. Then, the seeds are cultured as follows:
1. Surface disinfect with 70% (v/v) ethanol for 2 min then 20% (v/v) bleach for 20 min. Rinse three times in sterile MS media.
2. Germinate the seed on MS media containing 10 g/l agar, 30 g/l sucrose but no PGRs for 3 days at 27° C.
3. Axenically remove the testa, remove the cotyledonary notes, cut the cotyledons transversely in half and use the distal cotyledonary halves to establish callus cultures.

To initiate callus growth, cotyledonary halves are placed on MS medium with 30 g/l sucrose, 5 mM kinetin, 100 mg/l myoinositol, 0.5 mg/mL thiamine-HCl pH 5.7 at 27° C. unless noted below. The medium contains 5 mM indolebutyric acid as auxin. Place cotyledonary halves in tubes containing 10 mL solidified media. Incubate for 28 days.

To assay callus growth, pieces of callus each approximately 25 mg should be added to sterile tubes containing 10 mL media with varying concentrations of *H. glycines, F. solani* or extracts thereof. After 28 days at 28° C. the explants are evaluated for growth and growing sectors subcultured.

Cell suspensions are derived by placing 2 g of a macerated callus in 40 mL of MS medium. The flask, a 125 mL Erlenmeyer flask, should be capped with a foam plug. Subcultures should be made every 14 days into fresh media by allowing the cells to settle, removing the old media by aspiration, adding twice the volume of fresh media and splitting into two flasks.

Soybean tissue capable of regeneration to whole plants are grown in the presence of *H. glycines, F. solani* or extracts thereof. Cell lines representing mutants capable of continued growth are regenerated and the heritability of SCN or SDS resistance determined in these plants or their seed or tissue derived progeny.

REFERENCES

The publications and other materials listed below and/or set forth in the text above to illuminate the background of the invention, and in particular cases, to provide additional details respecting the practice, are incorporated in their entirety herein by reference. Materials used herein include but are not limited to the following listed references.

Adelman et al. (1983) *DNA* 2:183-193.
Alam and Cook (1990) *Anal Biochem* 188:245-254.
Altschul et al. (1990) *J Mol Biol* 215:403-410.
Arondel et al. (1992) *Science* 258:1353-1355.
Ausubel et al. (1992) *Current Protocols in Molecular Biology*, John Wylie and Sons, Inc., New York.
Bartlett et al. (1982) in *Methods in Chloroplast Molecular Biology*, Edelmann et al. (Eds.), pp 1081-1091, Elsevier.
Barton (1998) *Acta Crystallogr D Biol Crystallogr* 54:1139-1146.
Batzer et al. (1991) *Nucleic Acid Res* 19:3619-3623.
Bell-Johnson et al. (1998) *Soybean Genet Newslett* 25:115-118.
Bernard et al. (1988) *USDA Tech Bull* 1796.
Bevan (1984) *Nucl Acids Res* 12:8711-8721.
Bevan et al. (1983) *Nature* 304:184-187.
Binet et al. (1991) *Plant Science* 79: 87-94.
Blochlinger & Diggelmann (1984) *Mol Cell Biol* 4:2929-2931.
Bourouis et al., (1983) *EMBO J.* 2(7):1099-1104.
Bodanszky, et al. (1976) *Peptide Synthesis*, John Wiley and Sons, Second Edition, New York
Brookes (1999) *Gene* 234(2):177-186.
Brown et al. (1987) *Principles and Practice of Nematode Control in Crops*, pp 179-232, Academic Press, Orlando Fla.
Callis et al. (1987) *Genes Develop* 1:1183-1200.
Chang et al. (1996) *Crop Sci* 36:965-971.
Chang et al. (1997) *Crop Science* 37(3):965-971.
Chase et al. (1997) *Theor Appl Genet.* 94:724-730.
Chibbar et al. (1993) *Plant Cell Rep* 12:506-509.
Christou et al. (1991) *Biotechnology* 9:957-962.
Comai et al. (1988) *J Biol Chem* 263:15104-15109.
Concibido (1996) *Theor Appl Genet.* 93:234-241.

Concibido et al. (1997) *Crop Sci* 37:258-264.
Conner et al. (1983) *Proc Natl Acad Sci USA* 80:278-282.
Cregan et al. (1999a) *Crop Sci* 39:1464-1490.
Cregan et al. (1999b) *Theor Appl Genet.* 99:811-818.
Cregan et al. (1999c) *Theor Appl Genet.* 99:918-928.
Cubitt et al. (1995) *Trends Biochem Sci* 20:448-455.
Datta et al. (1990) *Biotechnology* 8:736-740.
EP 0 292 435
EP 0 332 104
EP 0 332 581
EP 0 342 296
EP 0 392 225
EP 0 452 269
Fehr (1987) in *Soybeans: Improvement Production and Uses* 2nd Ed., J. R. Wilcox (ed.), American Society of Agronomy, Madison, Wis.
Firek et al. (1993) *Plant Molec Biol* 22:129-142.
Fromm et al. (1990) *Biotechnology* 8:833-839.
Gallie et al. (1987) *Nucl Acids Res* 15:8693-8711.
Glover, ed. (1985) *DNA Cloning: A Practical Approach*, MRL Press, Ltd., Oxford, United Kingdom.
Gomez A. K. and A. A. Gomez (1984) *Statistical Procedures For Agricultural Research.* 2nd ed. John Wiley & Sons New York
Gordon-Kamm et al. (1990) *Plant Cell* 2:603-618.
Gritz et al. (1983) *Gene* 25:179-188.
Harlow and Lane (1988) *Antibodies: A Laboratory Manual*, Cold Spring Harbor Laboratory Press, Cold Spring Harbor, N.Y.
Hartwig and Epps (1973) *Crop Science* 13:287.
Henikoff et al. (2000) *Electrophoresis* 21 (9):1700-1706.
Henikoff and Henikoff (1989) *Proc Natl Acad Sci USA* 89:10915.
Henikoff and Henikoff (2000) *Adv Protein Chem* 54:73-97.
Hnetkovsky et al. (1996) *Crop Science* 36(2):393-400.
Hofgen & Willmitzer (1988) *Nucl Acids Res* 16:9877.
Huang et al. (2000) *Pac Symp Biocomput* 230-241.
Hudspeth & Grula (1989) *Plant Molec Biol* 12:579-589.
Hutchens and Yip (1993) *Rapid Commun Mass Spectrom* 7: 576-580.
Kalinina et al. (1997) *Nucl Acids Res* 25:1999-2004.
Kanazin et al. (1996) *Proc Natl Acad Sci USA* 93(21):11746-11750.
Karlin and Altschul (1993) *Proc Natl Acad Sci USA* 90:5873-87.
Keim et al. (1997) *Crop Science* 37:537-543.
Kestila et al. (1998) *Mol Cell* 1 (4):575-582.
Klein et al. (1987) *Nature* 327:70-73.
Koduri and Poola (2001) *Steroids* 66(1):17-23.
Koziel et al. (1993) *Biotechnology* 11:194-200.
Kyte et al. (1982) *J Mol Biol* 157:105.
Landers & Botstein (1989) *Genetics* 121:185-199.
Landgren et al. (1988) *Science* 241:1007.
Landgren et al. (1988) *Science* 242:229-237.
Landegren et al. (1998) *Genome Res* 8:769-776.
Lark et al. (1993) *Theor Appl Genet.* 86:901-906.
Li and Herskowitz (1993) *Science* 262:1870-1874.
Liedberg et al. (1983) *Sensors Actuators* 4:299-304.
Livak et al. (1995) *PCR Meth and Applic* 4:357-362.
Livak et al. (1995) *Nat Genet.* 9:341-342.
Logemann et al. (1989) *Plant Cell* 1:151-158.
Luo et al. (1999) *Plant Disease* 83:1155-1159.
Madge et al. (1972) *Phys Rev Lett* 29:705-708.
Mahalingam et al. (1995) *Breed Sci* 45:435-445.
Mahalingham et al. (1996) *Genome* 39:986-998
Maiti et al. (1997) *Proc Natl Acad Sci USA*, 94:11753-11757.
Malmquist (1993) *Nature* 361:186-187.
Martin et al. (1993) *Science* 262:1432-1436.
Mathews et al. (1998) *Theor Appl Genet.* 97:1047-1052.
Matthews et al. (1991) *Soybean Genetics Newsletter.*
McBride et al. (1990) *Plant Molecular Biology* 14:266-276.
McElroy et al. (1990) *Plant Cell* 2:163-171.
McElroy et al. (1991) *Mol Gen Genet.* 231:150-160.
Meksem et al. (1995) *Mol Gen Genet.* 249:74-81.
Meksem et al. (1999) *Theor Appl Genet.* 99:1131-1142.
Meksem et al. (2000) *Theor Appl Genet.* 101:747-755.
Messing & Vierra (1982) *Gene* 19:259-268.
Myers & Anand (1991), *Euphytica* 55:197-201.
Nasarabadi et al. (1999) *BioTechniques* 27:1116-1117.
Needleman & Wunsch (1970) *J Mol Biol* 48:443-453.
Njiti et al. (1996) *Crop Science* 36:1165-1170.
Ochman et al. (1990) in *PCR protocols: a Guide to Methods and Applications*, Innis et al. (eds.), pp. 219-227, Academic Press, San Diego, Calif.
Ohtsuka et al. (1985) *J Biol Chem* 260:2605-2608.
Orita et al. (1989) *Proc Natl Acad Sci USA* 86(8):2766-2770.
Paszkowski et al. (1984) *EMBO J.* 3:2717-2722.
Paterson et al. (1990) *Genetics* 124:735-742.
Pearson & Lipman (1988) *Proc Natl Acad Sci USA* 85:24442448.
Potrykus et al. (1985) *Mol Gen Genet.* 199:169-177.
Prabhu et al. (1999) *Crop Science* 39(4):982-987.
Price (1993) *Blood Rev* 7:127-134.
Rao-Arrelli et al. (1988) *Crop Science* 28:650-652.
Rao-Arrelli et al. (1992) *Crop Science* 32:862-864.
Regan et al. (2000) *Anal Biochem* 286(2):265-276.
Reich et al. (1986) *Biotechnology* 4:1001-1004.
Riggs and Schmidt (1988) *J Nematol* 20:392-395.
Rogers et al. (1989) *Proc Natl Acad Sci USA* 82:6512-6516.
Rohrmeier & Lehle (1993) *Plant Molec Biol* 22:783-792.
Rommens et al. (1989) *Science* 245:1059-1065.
Rose & Botstein (1983) *Meth Enzymol* 101:167-180.
Rossolini et al. (1994) *Mol Cell Probes* 8:91-98.
Rothstein et al. (1987) *Gene* 53:153-161.
Saiki et al. (1985) *Bio/Technology* 3:1008-1012.
Sambrook et al. eds. (1989) *Molecular Cloning: A Laboratory Manual*, Cold Spring Harbor Laboratory Press, Cold Spring Harbor, N.Y., N.Y.
Saqi et al. (1999) *Bioinformatics* 15:521-522.
Sauer (1998) *Methods* 14(4):381-392.
Schmidhauser & Helinski (1985) *J Bacteriol* 164:446-455.
Schocher et al. (1986) *Biotechnology* 4:1093-1096.
Shimamoto et al. (1989) *Nature* 338:274-277.
Shinshi et al. (1990) *Plant Molec Biol* 14:357-368.
Shoemaker et al. (1995) *Crop Science* 35:436-446.
Silhavy et al. (1984) *Experiments with Gene Fusions*, Cold Spring Harbor Laboratory, Cold Spring Harbor, N.Y., N.Y.
Singh et al. (1989) *Biotechniques* 7:252-261.
Skuzeski et al. (1990) *Plant Molec Biol* 15:65-79.
Smith & Waterman (1981) *Adv Appl Math* 2:482.
Smith & Camper (1973) *Crop Science* 13:459.
Spencer et al. (1990) *Theor Appl Genet.* 79:625-631.
Staskawicz (1995) *Science* 268:661-667.
Stoneking et al. (1991) *Am J Hum Genet.* 48(2):370-82.
Thompson et al. (1987) *EMBO J.* 6:2519-2523.
Tijssen (1993) in *Laboratory Techniques in Biochemistry and Molecular Biology-Hybridization with Nucleic Acid Probes*, part 1 chapter 2, Elsevier, New York, N.Y.
Trask (1991) *Trends Genet.* 7:149-154.
Uknes et al. (1992) *The Plant Cell* 4:645-656.
Uknes et al. (1993) *The Plant Cell* 5:159-169.
Unger et al. (1.989) *Plant Molec Biol* 13:411-418.
U.S. Pat. No. 4,196,265
U.S. Pat. No. 4,554,101

U.S. Pat. No. 4,940,935
U.S. Pat. No. 4,945,050
U.S. Pat. No. 5,036,006
U.S. Pat. No. 5,100,792
U.S. Pat. No. 5,188,642
U.S. Pat. No. 5,260,203
U.S. Pat. No. 5,523,311
U.S. Pat. No. 5,591,616
U.S. Pat. No. 5,614,395
U.S. Pat. No. 5,629,158
U.S. Pat. No. 5,639,949
U.S. Pat. No. 5,834,228
U.S. Pat. No. 5,872,011
U.S. Pat. No. 5,948,953
U.S. Pat. No. 5,952,546
U.S. Pat. No. 5,958,624
U.S. Pat. No. 5,986,173
U.S. Pat. No. 5,994,526
U.S. Pat. No. 5,994,527
U.S. Pat. No. 6,096,555
U.S. Pat. No. 6,162,967
U.S. Pat. No. RE36,449
van den Broeck et al. (1985) *Nature* 313:358-363.
Vasil et al. (1992) *Biotechnology* 10:667-674.
Vasil et al. (1993) *Biotechnology* 11:1553-1558.
Vidal et al. (1996) *Proc Natl Acad Sci USA* 93(19):10315-10320.
Vos et al. (1995) *Nucleic Acids Research* 23:4407-4414.
Wang et al. (1998) *Science* 280(5366):1077-82.
Warner et al. (1993) *Plant J* 3:191-201.
Webb et al. (1995) *Theor Appl Genet.* 91:574-581.
Weeks et al. (1993) *Plant Physiol* 102:1077-1084.
Weiseman et al. (1992) *Theor Appl Genet.* 85:136-138
White et al. (1990) *Nucl Acids Res* 18:1062.
WO 93/07278
WO 93/21335
WO 94/00977
WO 97/47763
Worrall et al. (1998) *Anal Biochem* 70:750-756.
Wrather et al. (1995) *Plant Disease* 79:1076-1079.
Xu et al. (1993) *Plant Molec Biol* 22:573-588.
Yuan et al. (1999) *Hum Mutat* 14(5):440-446.
Zhang et al. (1988) *Plant Cell Rep* 7:379-384.
Zhang et al. (1994) *Mol Gen Genet.* 244:613-621.
Zhu et al. (1996) *Mol Gen Genet.* 252:483-488.
Zimmer et al. (1993) *Peptides* pp. 393B394, ESCOM Science Publishers, B. V.
Zobrist et al. (2000) *Soybean Genet Newslett* 27:10-15.

It will be understood that various details of the invention can be changed without departing from the scope of the invention. Furthermore, the foregoing description is for the purpose of illustration only, and not for the purpose of limitation—the invention being defined by the claims.

---

What is claimed is:

1. An isolated and purified biologically active Soybean Cyst Nematode or Soybean Sudden Death Syndrome (SCN/SDS) resistance polypeptide having at least 95% sequence identity to SEQ ID NO 14, said polypeptide encoded by gene located within a quantitative trait locus mapping to linkage group G and mapped by genetic markers of SEQ ID NOs:1-6, said gene located along said quantitative trait locus between said markers.

2. An isolated and purified biologically active SCN/SDS resistance polypeptide, said polypeptide encoded by gene located within a quantitative trait locus mapping to linkage group G and mapped by genetic markers of SEQ ID NOs:1-6, said gene located along said quantitative trait locus between said markers, wherein the polypeptide comprises:
   (a) a polypeptide encoded by the nucleic acid sequence of SEQ ID NO:13; or
   (b) a polypeptide having the amino acid sequence of SEQ ID NO:14.

3. The isolated and purified biologically active SCN/SDS resistance polypeptide of claim 1, modified to be in detectably labeled form.

4. An isolated and purified soybean disease resistance polypeptide, wherein the disease is one of *Heterodera glycines* infestation and *Fusarium solani* infection, said polypeptide encoded by gene located within a quantitative trait locus mapping to linkage group G and mapped by genetic markers of SEQ ID NOs:1-6, said gene located along said quantitative trait locus between said markers, wherein the isolated and purified polypeptide is selected from the group consisting of:
   (a) an isolated and purified polypeptide having the amino acid sequence of amino acids 1-610 of SEQ ID NO:14; and
   (b) an isolated and purified polypeptide encoded by the nucleotide sequence set forth as nucleotides 1-1830 of SEQ ID NO:13.

* * * * *